United States Patent
Loughhead et al.

(10) Patent No.: US 7,053,103 B2
(45) Date of Patent: May 30, 2006

(54) RING FUSED PYRAZOLE DERIVATIVES AS CRF ANTAGONISTS

(75) Inventors: David Garrett Loughhead, Belmont, CA (US); Counde O'Yang, Sunnyvale, CA (US)

(73) Assignee: Syntex (U.S.A.) LLC, Palo Alato, CA (US)

( * ) Notice: Subject to any disclaimer, the term of this patent is extended or adjusted under 35 U.S.C. 154(b) by 41 days.

(21) Appl. No.: 10/914,368

(22) Filed: Aug. 9, 2004

(65) Prior Publication Data

US 2005/0014781 A1    Jan. 20, 2005

Related U.S. Application Data

(62) Division of application No. 10/308,386, filed on Dec. 3, 2002, now Pat. No. 6,821,984.

(60) Provisional application No. 60/408,613, filed on Sep. 6, 2002, provisional application No. 60/336,751, filed on Dec. 4, 2001.

(51) Int. Cl.
*A61K 31/44* (2006.01)
*C07D 471/04* (2006.01)

(52) U.S. Cl. .................. 514/303; 546/119
(58) Field of Classification Search ............ 546/119; 514/303

See application file for complete search history.

(56) References Cited

U.S. PATENT DOCUMENTS

| | | | |
|---|---|---|---|
| 5,668,145 | A | 9/1997 | Bright |
| 5,705,646 | A | 1/1998 | Bright et al. |
| 5,712,303 | A | 1/1998 | Faraci et al. |
| 5,760,225 | A | 6/1998 | Yuan |
| 6,200,979 | B1 | 3/2001 | Bright et al. |

OTHER PUBLICATIONS

Hehemann, et al., "Addition of Diamines to Methylthiopyridones," *J. Heterocyclic Chem.*, (1994), pp. 393-396, vol. 31 (2).

Mohareb, et al., "Reactions with 4-Phenyl-3-thiosemicarbazide: A New Approach for the Synthesis of Pyrazole, Thiazole, Pyridine and Pyrazolo[3,4-*b*]- Pyridine Derivatives," *Sulfur Letters*, (1991), pp. 101-113, vol. 13 (3).

Chemstar Ltd, Moscow, Russia, Database Chemcats 'online! Chemical Abstracts Service, Columbus, Ohio, US; retrieved from STN XP-002233223, Order Nos.: CHS 0390519; CHS 0053761, dated May 16, 2001.

Asinex, Moscow, Russia, Database Chemcats 'online! Chemical Abstracts Service, Columbus, Ohio, US; retrieved from STN XP-002233224, Order No.: BAS 0138479, dated May 10, 2001.

Specs and Biospecs B.V., Rijswijk, NL, Database Chemcats 'online! Chemical Abstracts Service, Columbus, Ohio, US; retrieved from STN XP-002233225, Order No.: AG-667/12449002 & "Compounds for Screening", dated Jul. 1, 2001.

Ambinter, Paris, France, Database Chemcats 'online! Chemical Abstracts Service, Columbus, Ohio, US; retrieved from STN XP-002233226, Order Nos.:132-45219; 132-45159; 132-45157; 132-45155; Stock1S-39093, Stock1S-34168; dated Jan. 21, 2002.

*Primary Examiner*—Rita Desai
(74) *Attorney, Agent, or Firm*—Brian L. Buckwalter

(57) ABSTRACT

This invention relates to compounds which are generally CRF-1 receptor antagonists and which are represented by Formula I or Formula II:

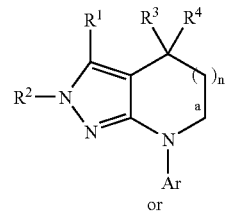

Formula I or

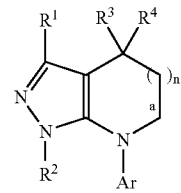

Formula II wherein Ar is optionally substituted aryl or heteroaryl, $R^1$–$R^4$ are as defined in the specification; or individual isomers, racemic or non-racemic mixtures of isomers, or pharmaceutically acceptable salts thereof. The invention further relates to processes for preparing such compounds, to pharmaceutical compositions containing such compounds, and to methods for their use as therapeutic agents.

11 Claims, No Drawings

RING FUSED PYRAZOLE DERIVATIVES AS CRF ANTAGONISTS

CROSS REFERENCE TO PRIOR APPLICATIONS

This application is a divisional application of U.S. Ser. No 10/308,386, filed Dec. 3, 2002, now U.S. Pat. No. 6,821,984, which claims benefit under Title 35 U.S.C. 119(e) of U.S. Provisional Applications Nos. 60/336,751 filed Dec. 4, 2001; and 60/408,613 filed Sep. 6, 2002, all applications are hereby incorporated by reference in its entirety.

FIELD OF THE INVENTION

This invention relates to ring fused pyrazole derivatives with CRF activity, and associated pharmaceutical compositions, and methods for use as therapeutic agents.

BACKGROUND OF THE INVENTION

Corticotropin releasing factor (CRF) or hormone (CRH) is one of several neurohormones synthesized by specific hypothalamic nuclei in the brain where it activates the transcription of the pro-opiomelanocortin (POMC) gene resulting in release of adrenocorticotropic hormone (ACTH) and beta-endorphin from anterior pituitary cells (Vale et al, Science 213, 1394–1397 (1981)). The fundamental role of CRF is to prepare the organism for an appropriate response to various stressors such as physical trauma, insults of the immune system and social interactions. CRF also has CNS effects by acting at higher centers in the brain, particularly cortical regions where there is a widespread distribution of CRF neurons. CRF is believed to be a key intermediary in communication between the immune, central nervous, endocrine and cardiovascular systems (Sapolsky et al, Science 238, 522–524 (1987)). The role played by CRF in integrating the response of the immune system to physiological, psychological and immunological stressors has been described in the art, e.g. J. E. Blalock, Physiological Reviews 69, 1 (1989) and J. E. Morley, Life Sci. 41, 527 (1987).

CRF antagonists are effective in the treatment of a wide range of stress-related illnesses, mood disorders such as depression, major depressive disorder, single episode depression, recurrent depression, child abuse induced depression, postpartum depression, dysthemia, bipolar disorder and cyclothymia; chronic fatigue syndrome; eating disorders such as obesity, anorexia and bulimia nervosa; generalized anxiety disorder; panic disorder; phobias; obsessive-compulsive disorder; post-traumatic stress disorder; pain perception such as fibromyalgia; headache; stress-induced gastrointestinal dysfunction such as irritable bowel syndrome (IBS), colonic hypersensitivity or spastic colon; hemorrhagic stress; ulcers; stress-induced psychotic episodes; inflammatory disorders such as rheumatoid arthritis and osteoarthritis; asthma; psoriasis; allergies; premature birth; hypertension; congestive heart failure; sleep disorders; neurodegenerative diseases such as Alzheimer's disease, senile dementia, Parkinson's disease and Huntington's disease; head or spinal cord trauma; ischemic neuronal damage; excitotoxic neuronal damage; epilepsy; stroke; psychosocial dwarfism; chemical dependencies and addictions; drug and alcohol withdrawal symptoms;,stress-induced immune dysfunctions; immune suppression and stress-induced infections; cardiovascular or heart related diseases; fertility problems; and/or human immunodeficiency virus infections. Accordingly clinical data suggests that CRF receptor antagonists may represent novel antidepressants and/or anxiolytic drugs that may be useful in the treatment of the neuropsychiatric disorders manifesting hypersecretion of CRF.

In view of the above, efficacious and specific antagonists of CRF are desired as potentially valuable therapeutic agents for the treatment of psychiatric disorders and neurological diseases. It is thus desirable to discover new CRF antagonists.

All publications, patents, and patent applications cited herein, whether supra or infra, are each hereby incorporated by reference in its entirety.

SUMMARY OF THE INVENTION

This invention relates to compounds comprising Formula I or Formula II:

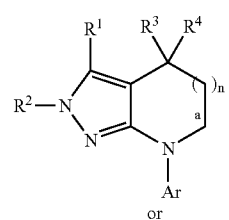

Formula I or

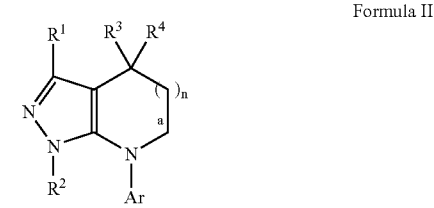

Formula II wherein:

$R^1$ is —$OR^a$, —$NR^aR^b$, —$CR^cR^dR^e$, $CO_2R^a$, or —$C(O)NR^aR^b$; or $R^1$ is hydrogen, halogen, cycloalkenyl, aryl, or heteroaryl, where each aryl or heteroaryl is optionally substituted with one or more substituents independently selected from $C_{1-6}$alkyl, $C_{1-6}$alkoxy, $C_{1-6}$alkylthio, $C_{1-6}$alkylsulfonyl, halogen, haloalkyl, cyano, nitro, —$C(O)NR^{a'}R^{b'}$, and —$NR^{a'}R^{b'}$, where $R^{a'}$ and $R^{b'}$ are each independently selected from the group consisting of hydrogen, $C_{1-9}$alkyl, and $C_{1-9}$alkylcarbonyl;

$R^2$ is hydrogen, $C_{1-6}$alkyl, $C_{3-6}$cycloalkyl, $C_{3-6}$cycloalkylalkyl, $C_{1-6}$alkylcarbonyl, $C_{1-6}$alkylsulfonyl, aryl, or arylalkyl, wherein said aryl or arylalkyl is optionally substituted with one or more substituents independently selected from $C_{1-6}$alkyl, haloalkyl, $C_{1-6}$alkoxy, and halogen;

$R^3$ and $R^4$ are each independently selected from hydrogen and $C_{1-6}$alkyl, or $R^3$ and $R^4$ are taken together with the carbon, to which they are attached to form a $C_{3-6}$cycloalkyl ring;

Ar is aryl or heteroaryl, each optionally substituted with one or more substituents independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl;

$R^a$ and $R^b$ are each independently selected from the group consisting of hydrogen, $C_{1-9}$alkyl, hydroxyalkyl, $C_{1-6}$alkoxyalkyl, $C_{1-6}$alkylthioalkyl, carboxyalkyl, $C_{1-6}$alkoxycarbonyl, $C_{1-6}$-alkoxy-$C_{1-3}$alkylcarbonyl, acyl, $C_{3-6}$cycloalkyl, $C_{3-6}$cycloalkylalkyl, di-$C_{3-6}$cycloalkyl$C_{1-3}$alkyl, $C_{1-6}$heteroalkyl, aminoalkyl, aminocarbonylalkyl, cyanoalkyl, $C_{5-8}$heterocyclyl, heterocyclylalkyl, aryl, arylalkyl, heteroaryl, heteroarylalkyl, phenylalkyl, diphenylalkyl, phenylsulfonyl optionally substituted as described for phenyl below, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, haloalkyl, $C_{1-6}$alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

$R^c$ is hydrogen, hydroxy, $C_{1-6}$alkoxy, or $-NR^{a'''}R^{b'''}$;

$R^d$ and $R^e$ are each independently selected from the group consisting of hydrogen, $C_{1-9}$alkyl, hydroxyalkyl, $C_{1-6}$alkoxyalkyl, $C_{1-6}$alkylthioalkyl, heteroalkyl, heterocyclyl, heterocyclylalkyl, $C_{3-6}$cycloalkyl, $C_{3-6}$cycloalkylalkyl, di-$C_{3-6}$cycloalkyl-$C_{1-3}$alkyl, aryl, arylalkyl, heteroaryl, heteroarylalkyl, phenylalkyl, diphenyl-$C_{1-3}$alkyl, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, and halogen; or $R^c$ and $R^d$ are taken together to form a divalent group selected from $C_{1-6}$alkylidenyl, $C_{1-6}$heteroalkylidenyl, $C_{3-6}$cycloalkylidenyl, $C_{3-6}$cycloalkyl-alkylidenyl, $C_{3-6}$Cycloalkylalkyl-alkylidenyl, $C_{3-6}$heterocyclylidenyl, $C_{3-6}$heterocyclyl-$C_{1-3}$alkylidenyl, $C_{3-6}$heterocyclylalkyl-$C_{1-3}$alkylidenyl, aryl-$C_{1-3}$alkylidenyl, aryl-$C_{1-3}$alkyl-alkylidenyl, heteroaryl-$C_{1-3}$alkylidenyl, and heteroarylalkyl-$C_{1-3}$alkylidenyl, wherein each of said cycloalkyl, aryl, or heteroaryl groups is optionally substituted with one or more substituents independently selected from $C_{1-6}$alkyl, haloalkyl, $C_{1-6}$alkoxy, amino, alkylamino, dialkylamino, and halogen; or $R^d$ and $R^e$ are taken together with the carbon to which they are attached to form a cycloalkyl or heterocyclyl ring;

$R^{a'''}$ and $R^{b'''}$ are each independently selected from the group consisting of hydrogen, $C_{1-9}$alkyl, hydroxyalkyl, $C_{1-6}$alkoxyalkyl, $C_{1-6}$alkylthioalkyl, carboxyalkyl, $C_{1-6}$alkoxycarbonyl, $C_{1-6}$-alkoxy-$C_{1-3}$alkylcarbonyl, acyl, $C_{3-6}$cycloalkyl, $C_{3-6}$cycloalkylalkyl, di-$C_{3-6}$cycloalkyl-$C_{1-3}$alkyl, $C_{1-6}$heteroalkyl, aminoalkyl, aminocarbonylalkyl, cyanoalkyl, $C_{5-8}$heterocyclyl, heterocyclylalkyl, aryl, arylalkyl, heteroaryl, heteroarylalkyl, phenylalkyl, diphenyl-$C_{1-3}$alkyl, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^{a'''}$ and $R^{b'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, haloalkyl, $C_{1-6}$alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

n is an integer selected from 0, 1 and 2;

a is a single or double bond;

providing that when n is 0, $R^1$ is not hydrogen; when n is 0 and a is a double bond, $R^4$ is absent; and when n is 1 or 2, a is a single bond;

or individual isomers, racemic or non-racemic mixtures of isomers, or pharmaceutically acceptable salts or solvates thereof.

In one embodiment, a compound of Formula I is described:

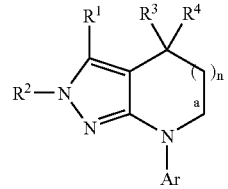

Formula I wherein $R^1$, $R^2$, $R^3$, $R^4$, Ar, a, and n are as defined above.

In another embodiment, compounds of Formula III are described:

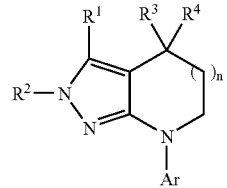

Formula III wherein the integer n is 1 or 2, and $R^1$, $R^2$, $R^3$, $R^4$, and Ar are as defined above.

In another embodiment, compounds of Formula III are described, wherein Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, C$_{1-9}$alkyl, and C$_{1-9}$alkylcarbonyl, the integer n is 1 or 2, and R$^1$, R$^2$, R$^3$, and R$^4$ are as defined above.

In one aspect, such compounds are described wherein R$^3$ and R$^4$ are each independently selected from hydrogen and methyl.

In another aspect, such compounds are described wherein Ar is a 2,4-disubstituted or 2,4,6-trisubstituted phenyl, and the substituents are each independently selected from the group consisting of C$_{1-6}$alkyl, C$_{1-6}$alkoxy, C$_{1-6}$alkylthio, C$_{1-6}$alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, C$_{1-9}$alkyl, and C$_{1-9}$alkylcarbonyl.

In another aspect, such compounds are described wherein Ar is a 2,4-disubstituted or 2,4,6-trisubstituted phenyl, and the substituents are each independently selected from the group consisting of C$_{1-6}$alkyl, C$_{1-6}$alkoxy, C$_{1-6}$alkylthio, halogen, haloalkyl, cyano, alkylamino, dialkylamino, and nitro.

In another aspect, such compounds are described wherein R$^2$ is hydrogen, C$_{1-6}$alkyl, or C$_{1-6}$alkylcarbonyl.

In another embodiment, compounds of Formula IV are described:

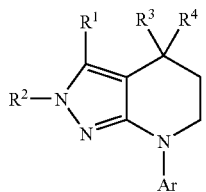

Formula IV wherein Ar is a 2,4-disubstituted or 2,4,6-trisubstituted phenyl, and the substituents are each independently selected from the group consisting of C$_{1-6}$alkyl, C$_{1-6}$alkoxy, C$_{1-6}$alkylthio, halogen, haloalkyl, cyano, alkylamino, dialkylamino, and nitro, R$^2$ is hydrogen, C$_{1-6}$alkyl, or C$_{1-6}$alkylcarbonyl, R$^3$ and R$^4$ are each independently selected from hydrogen and methyl; and R$^1$ is as defined above.

In another embodiment, compounds of Formula III are described, wherein R$^3$ and R$^4$ are each independently selected from hydrogen and methyl, Ar is a di- or tri-substituted phenyl, and the substituents are each independently selected from the group consisting of C$_{1-6}$alkyl, C$_{1-6}$alkoxy, C$_{1-6}$alkylthio, C$_{1-6}$alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, C$_{1-9}$alkyl, and C$_{1-9}$alkylcarbonyl, the integer n is 1 or 2, R$^2$ is as defined above; and R$^1$ is —CR$^c$R$^d$R$^e$; R$^c$ is hydroxy; and R$^d$ and R$^e$ are as defined above.

In one aspect, such compounds are described wherein R$^d$ and R$^e$ are each independently selected from the group consisting of hydrogen, C$_{1-9}$alkyl, C$_{1-6}$alkoxyalkyl, C$_{3-6}$cycloalkyl, C$_{3-6}$cycloalkylalkyl, aryl, arylalkyl, heteroaryl, and heteroarylalkyl, where each of said aryl or heteroaryl groups is optionally substituted with one or more substituents independently selected from the group consisting of C$_{1-6}$alkyl, haloalkyl, C$_{1-6}$alkoxy, and halogen.

In one alternative, such compounds are described wherein R$^d$ and R$^e$ are each independently selected from the group consisting of C$_{1-9}$alkyl, C$_{1-6}$alkoxyalkyl, aryl, and heteroaryl, where each of said aryl or heteroaryl groups is optionally substituted with one or more substituents independently selected from the group consisting of C$_{1-6}$alkyl, haloalkyl, C$_{1-6}$alkoxy, and halogen.

In another aspect, such compounds are described wherein R$^2$ is C$_{1-6}$alkyl; R$^3$ and R$^4$ are hydrogen; and Ar is a 2,4-disubstituted or 2,4,6-trisubstituted phenyl, and the substituents are each independently selected from the group consisting of C$_{1-6}$alkyl, C$_{1-6}$alkoxy, halogen, haloalkyl, cyano, and —NR$^{a''}$R$^{b''}$, where R$^{a''}$ and R$^{b''}$ are each independently selected from the group consisting of hydrogen and C$_{1-9}$alkyl.

In another alternative, such compounds are described wherein R$^d$ and R$^e$ are taken together to form a cycloalkyl or heterocyclyl group.

In another embodiment, compounds of Formula III are described, wherein R$^3$ and R$^4$ are each independently selected from hydrogen and methyl, Ar is a di- or tri-substituted phenyl, and the substituents are each independently selected from the group consisting of C$_{1-6}$alkyl, C$_{1-6}$alkoxy, C$_{1-6}$alkylthio, C$_{1-6}$alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, C$_{1-9}$alkyl, and C$_{1-9}$alkylcarbonyl, the integer n is 1 or 2, R$^2$ is as defined above; and R$^1$ is —CR$^c$R$^d$R$^e$; R$^e$ is selected from the group consisting of C$_{1-9}$alkyl, C$_{1-6}$alkoxyalkyl, C$_{3-6}$cycloalkyl, C$_{3-6}$cycloalkylalkyl, aryl, arylalkyl, heteroaryl, and heteroarylalkyl, where each of said aryl or heteroaryl groups is optionally substituted with one or more substituents independently selected from the group consisting of C$_{1-6}$alkyl, haloalkyl, C$_{1-6}$alkoxy, and halogen; and R$^c$ and R$^d$ are taken together to form a divalent group selected from C$_{1-6}$alkylidenyl, C$_{1-6}$heteroalkylidenyl, C$_{3-6}$cycloalkylidenyl, C$_{3-6}$cycloalkyl-alkylidenyl, C$_{3-6}$cycloalkylalkyl-alkylidenyl, C$_{3-6}$heterocyclylidenyl, C$_{3-6}$heterocyclyl-C$_{1-3}$alkylidenyl, C$_{3-6}$heterocyclylalkyl-C$_{1-3}$alkylidenyl, aryl-C$_{1-3}$alkylidenyl, aryl-C$_{1-3}$alkyl-alkylidenyl, heteroaryl-C$_{1-3}$alkylidenyl, and heteroarylalkyl-C$_{1-3}$alkylidenyl, wherein each of said cycloalkyl, aryl, or heteroaryl groups is optionally substituted with one or more substituents independently selected from C$_{1-6}$alkyl, haloalkyl, C$_{1-6}$alkoxy, amino, alkylamino, dialkylamino, and halogen.

In one alternative, such compounds are described wherein R$^c$ and R$^d$ are taken together to form a divalent group selected from C$_{1-6}$alkylidenyl, C$_{3-6}$cycloalkyl-alkylidenyl, aryl-C$_{1-3}$alkylidenyl, and heteroaryl-C$_{1-3}$alkylidenyl, wherein each of said aryl or heteroaryl groups is optionally substituted with one or more substituents independently selected from C$_{1-6}$alkyl, haloalkyl, C$_{1-6}$alkoxy, amino, alkylamino, dialkylamino, and halogen.

In another embodiment, compounds of Formula III are described, wherein R$^3$ and R$^4$ are each independently selected from hydrogen and methyl, Ar is a di- or tri-substituted phenyl, and the substituents are each independently selected from the group consisting of C$_{1-6}$alkyl, C$_{1-6}$alkoxy, C$_{1-6}$alkylthio, C$_{1-6}$alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, C$_{1-9}$alkyl, and C$_{1-9}$alkylcarbonyl, the integer n is 1 or 2, R$^2$ is as defined above; and $R^1$ is —$CR^cR^dR^e$; $R^e$ is selected from the group consisting of $C_{1-9}$alkyl, $C_{1-6}$alkoxyalkyl, and heteroaryl, where the heteroaryl is optionally substituted with one or more substituents independently selected from the group consisting of $C_{1-6}$alkyl, haloalkyl, $C_{1-6}$alkoxy, and halogen; and $R^c$ and $R^d$ are taken together to form a divalent group selected from $C_{1-6}$alkylidenyl, $C_{3-6}$cycloalkyl-alkylidenyl, $C_{3-6}$heterocyclyl-$C_{1-3}$alkylidenyl, aryl-$C_{1-3}$alkylidenyl and heteroaryl-$C_{1-3}$alkylidenyl, wherein each of said aryl, or heteroaryl groups is optionally substituted with one or more substituents independently selected from $C_{1-6}$alkyl, $C_{1-6}$alkoxy, amino, alkylamino, and dialkylamino.

In another embodiment, compounds of Formula III are described, wherein $R^3$ and $R^4$ are each independently selected from hydrogen and methyl, Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is —$CR^cR^dR^e$; $R^c$ is hydrogen; and $R^d$ and $R^e$ are as defined above.

In one aspect, such compounds are described wherein $R^d$ and $R^e$ are each independently selected from the group consisting of $C_{1-9}$alkyl, $C_{1-6}$alkoxyalkyl, $C_{3-6}$cycloalkyl, $C_{3-6}$cycloalkylalkyl, aryl, arylalkyl, heteroaryl, and heteroarylalkyl, where each of said aryl or heteroaryl groups is optionally substituted with one or more substituents independently selected from the group consisting of $C_{1-6}$alkyl, haloalkyl, $C_{1-6}$alkoxy, and halogen.

In one alternative, such compounds are described wherein $R^d$ and $R^e$ are each independently selected from the group consisting of $C_{1-9}$alkyl, $C_{1-6}$alkoxyalkyl, aryl, and heteroaryl, where each of said aryl or heteroaryl groups is optionally substituted with one or more substituents independently selected from the group consisting of $C_{1-6}$alkyl, haloalkyl, $C_{1-6}$alkoxy, and halogen; $R^2$ is $C_{1-6}$alkyl; $R^3$ and $R^4$ are hydrogen; and Ar is a 2,4-disubstituted or 2,4,6-trisubstituted phenyl, and the substituents are independently selected from the group consisting of $C_{1-6}$alkyl, $C_{1-6}$alkoxy, halogen, haloalkyl, cyano, and —$NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is —$NR^aR^b$; —$C(O)NR^aR^b$; or —$CR^cR^dR^e$, where $R^c$ is —$NR^{a'''}R^{b'''}$; $R^d$ and $R^e$ are each independently selected from the group consisting of hydrogen and $C_{1-9}$alkyl; and $R^a$, $R^b$, $R^{a'''}$, and $R^{b'''}$ are as defined above.

In one aspect, such compounds are described wherein $R^a$, $R^b$, $R^{a'''}$, and $R^{b'''}$ are each independently selected from the group consisting of hydrogen, $C_{1-9}$alkyl, hydroxyalkyl, $C_{1-6}$alkoxyalkyl, $C_{3-6}$cycloalkylalkyl, heterocyclylalkyl, arylalkyl, and heteroarylalkyl, wherein each of said aryl or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In one alternative, such compounds are described wherein $R^a$ and $R^b$, or $R^{a'''}$ and $R^{b'''}$, are taken together with the nitrogen to which they are attached form an heterocyclyl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, and imidazoline, where each of said rings is optionally substituted with one or more substituents independently selected from the group consisting of hydroxy, oxo, alkyl, aminoalkyl, acyl, acylamino, aminocarbonyl, aminocarbonylalkyl, and aminocarbonylamino, and each of said amino groups is optionally monosubstituted or disubstituted with alkyl, or is contained in a pyrrolidinyl, piperidinyl, morpholinyl, or piperazinyl group.

In another embodiment, compounds of Formula III are described, wherein $R^3$ and $R^4$ are each independently selected from hydrogen and methyl, Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is —$NR^aR^b$; $R^a$ is selected from the group consisting of hydrogen, $C_{1-9}$alkyl, and $C_{1-6}$alkoxyalkyl; and $R^b$ is selected from the group consisting of $C_{1-9}$alkyl, hydroxyalkyl, $C_{1-6}$alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In one aspect, such compounds are described wherein $R^2$ is $C_{1-6}$alkyl; $R^3$ and $R^4$ are hydrogen; and Ar is a 2,4-disubstituted or 2,4,6-trisubstituted phenyl, and the substituents are independently selected from the group consisting of $C_{1-6}$alkyl, $C_{1-6}$alkoxy, halogen, haloalkyl, cyano, and —$NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is —$CR^cR^dR^e$; $R^c$ is —$NR^{a'''}R^{b'''}$; $R^d$ and $R^e$ are each independently selected from the group consisting of hydrogen and $C_{1-9}$alkyl; $R^{a'''}$ is selected from the group consisting of hydrogen, $C_{1-9}$alkyl, and $C_{1-6}$alkoxyalkyl; and $R^{b'''}$ is selected from the group consisting of $C_{1-9}$alkyl, hydroxyalkyl, $C_{1-6}$alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In one aspect, such compounds are described wherein $R^2$ is $C_{1-6}$alkyl; $R^3$ and $R^4$ are hydrogen; and Ar is a 2,4-disubstituted or 2,4,6-trisubstituted phenyl, and the substituents are independently selected from the group consisting of $C_{1-6}$alkyl, $C_{1-6}$alkoxy, halogen, haloalkyl, cyano, and —$NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is —$OR^a$, and $R^a$ is as defined above.

In one aspect, such compounds are described wherein $R^a$ is selected from the group consisting of $C_{1-9}$alkyl, $C_{1-6}$alkoxyalkyl, $C_{3-6}$cycloalkylalkyl, arylalkyl, and heteroarylalkyl, wherein each of said cycloalkyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In another aspect, such compounds are described wherein $R^2$ is $C_{1-6}$alkyl; $R^3$ and $R^4$ are hydrogen; and Ar is a 2,4-disubstituted or 2,4,6-trisubstituted phenyl, and the substituents are independently selected from the group consisting of $C_{1-6}$alkyl, $C_{1-6}$alkoxy, halogen, haloalkyl, cyano, and —$NR^{a''}R^{b''}$, where $R^{a''}$ and $R^{b''}$ are each independently selected from the group consisting of hydrogen and $C_{1-9}$alkyl.

In another embodiment, compounds of Formula III are described wherein $R^3$ and $R^4$ are each independently selected from hydrogen and methyl, Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is aryl or heteroaryl, where said aryl or heteroaryl is optionally substituted with one or more substituents independently selected from $C_{1-6}$alkyl, $C_{1-6}$alkoxy, $C_{1-6}$alkylthio, $C_{1-6}$alkylsulfonyl, halogen, haloalkyl, cyano, nitro, and —$NR^{a'}R^{b'}$, where $R^{a'}$ and $R^{b'}$ are each independently selected from the group consisting of hydrogen, $C_{1-9}$alkyl, and $C_{1-9}$alkylcarbonyl.

In one alternative, such compounds are described wherein the aryl or heteroaryl is optionally substituted with one or more substituents independently selected from $C_{1-6}$alkyl, $C_{1-6}$alkoxy, halogen, haloalkyl, cyano, and —$NR^{a'}R^{b'}$, where $R^{a'}$ and $R^{b'}$ are each independently selected from the group consisting of hydrogen, $C_{1-9}$alkyl, and $C_{1-9}$alkylcarbonyl.

In another embodiment, compounds of Formula III are described, wherein Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, and $R^1$, $R^2$, $R^3$, and $R^4$ are as defined above.

In one aspect, such compounds are described wherein $R^3$ and $R^4$ are each independently selected from hydrogen and methyl.

In another aspect, such compounds are described wherein Ar is a 2,4-disubstituted, 2,6-disubstituted, or 2,4,6-trisubstituted pyridin-3-yl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl.

In another aspect, such compounds are described wherein Ar is a 2,4-disubstituted, 2,6-disubstituted, or 2,4,6-trisubstituted pyridin-3-yl, and the substituents are each independently selected from the group consisting of $C_{1-6}$alkyl, $C_{1-6}$alkoxy, halogen, haloalkyl, alkylamino, and dialkylamino.

In another aspect, such compounds are described wherein $R^2$ is hydrogen, $C_{1-6}$alkyl, or $C_{1-6}$alkylcarbonyl.

In another embodiment, compounds of Formula IV are described wherein Ar is a 2,4-disubstituted, 2,6-disubstituted, or 2,4,6-trisubstituted pyridin-3-yl, and the substituents are each independently selected from the group consisting of $C_{1-6}$alkyl, $C_{1-6}$alkoxy, halogen, haloalkyl, alkylamino, and dialkylamino, $R^2$ is hydrogen, $C_{1-6}$alkyl, or $C_{1-6}$alkylcarbonyl, $R^3$ and $R^4$ are each independently selected from hydrogen and methyl; and $R^1$ is as defined above.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is —$CR^cR^dR^e$; $R^c$ is hydroxy; and $R^d$ and $R^e$ are as defined above.

In one aspect, such compounds are described wherein $R^d$ and $R^e$ are each independently selected from the group consisting of hydrogen, $C_{1-9}$alkyl, $C_{1-6}$alkoxyalkyl, $C_{3-6}$cycloalkyl, $C_{3-6}$cycloalkylalkyl, aryl, arylalkyl, heteroaryl, and heteroarylalkyl, where each of said aryl or heteroaryl groups is optionally substituted with one or more substituents independently selected from the group consisting of $C_{1-6}$alkyl, haloalkyl, $C_{1-6}$alkoxy, and halogen.

In one alternative, such compounds are described wherein $R^d$ and $R^e$ are each independently selected from the group consisting of $C_{1-9}$alkyl, $C_{1-6}$alkoxyalkyl, aryl, and heteroaryl, where each of said aryl or heteroaryl groups is optionally substituted with one or more substituents independently selected from the group consisting of $C_{1-6}$alkyl, haloalkyl, $C_{1-6}$alkoxy, and halogen.

In another aspect, such compounds are described wherein $R^2$ is $C_{1-6}$alkyl; $R^3$ and $R^4$ are hydrogen; and Ar is a 2,4-disubstituted, 2,6-disubstituted, or 2,4,6-trisubstituted pyridin-3-yl, and the substituents are each independently selected from the group consisting of $C_{1-6}$alkyl, $C_{1-6}$alkoxy, halogen, haloalkyl, and $-NR^{a''}R^{b''}$, where $R^{a''}$ and $R^{b''}$ are each independently selected from the group consisting of hydrogen and $C_{1-9}$alkyl.

In another alternative, such compounds are described wherein $R^d$ and $R^e$ are taken together to form a cycloalkyl or heterocyclyl group.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-CR^cR^dR^e$; $R^e$ is selected from the group consisting of $C_{1-9}$alkyl, $C_{1-6}$alkoxyalkyl, $C_{3-6}$cycloalkyl, $C_{3-6}$cycloalkylalkyl, aryl, arylalkyl, heteroaryl, and heteroarylalkyl, where each of said aryl or heteroaryl groups is optionally substituted with one or more substituents independently selected from the group consisting of $C_{1-6}$alkyl, haloalkyl, $C_{1-6}$alkoxy, and halogen; and $R^c$ and $R^d$ are taken together to form a divalent group selected from $C_{1-6}$alkylidenyl, $C_{1-6}$heteroalkylidenyl, $C_{3-6}$cycloalkylidenyl, $C_{3-6}$cycloalkyl-alkylidenyl, $C_{3-6}$cycloalkylalkyl-alkylidenyl, $C_{3-6}$heterocyclylidenyl, $C_{3-6}$heterocyclyl-$C_{1-3}$alkylidenyl, $C_{3-6}$heterocyclylalkyl-$C_{1-3}$alkylidenyl, aryl-$C_{1-3}$alkylidenyl, aryl-$C_{1-3}$alkyl-alkylidenyl, heteroaryl-$C_{1-3}$alkylidenyl, and heteroarylalkyl-$C_{1-3}$alkylidenyl, wherein each of said cycloalkyl, aryl, or heteroaryl groups is optionally substituted with one or more substituents independently selected from $C_{1-6}$alkyl, haloalkyl, $C_{1-6}$alkoxy, amino, alkylamino, dialkylamino, and halogen.

In one alternative, such compounds are described wherein $R^c$ and $R^d$ are taken together to form a divalent group selected from $C_{1-6}$alkylidenyl, $C_{3-6}$cycloalkyl-alkylidenyl, aryl-$C_{1-3}$alkylidenyl, and heteroaryl-$C_{1-3}$alkylidenyl, wherein each of said aryl or heteroaryl groups is optionally substituted with one or more substituents independently selected from $C_{1-6}$alkyl, haloalkyl, $C_{1-6}$alkoxy, amino, alkylamino, dialkylamino, and halogen.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-CR^cR^dR^e$; $R^e$ is selected from the group consisting of $C_{1-9}$alkyl, $C_{1-6}$alkoxyalkyl, and heteroaryl, where the heteroaryl is optionally substituted with one or more substituents independently selected from the group consisting of $C_{1-6}$alkyl, haloalkyl, $C_{1-6}$alkoxy, and halogen; and $R^c$ and $R^d$ are taken together to form a divalent group selected from $C_{1-6}$alkylidenyl, $C_{3-6}$cycloalkyl-alkylidenyl, $C_{3-6}$heterocyclyl-$C_{1-3}$alkylidenyl, aryl-$C_{1-3}$alkylidenyl and heteroaryl-$C_{1-3}$alkylidenyl, wherein each of said aryl, or heteroaryl groups is optionally substituted with one or more substituents independently selected from $C_{1-6}$alkyl, $C_{1-6}$alkoxy, amino, alkylamino, and dialkylamino.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-CR^cR^dR^e$; $R^c$ is hydrogen; and $R^d$ and $R^e$ are as defined above.

In one aspect, such compounds are described wherein $R^d$ and $R^e$ are each independently selected from the group consisting of $C_{1-9}$alkyl, $C_{1-6}$alkoxyalkyl, $C_{3-6}$cycloalkyl, $C_{3-6}$cycloalkylalkyl, aryl, arylalkyl, heteroaryl, and heteroarylalkyl, where each of said aryl or heteroaryl groups is optionally substituted with one or more substituents independently selected from the group consisting of $C_{1-6}$alkyl, haloalkyl, $C_{1-6}$alkoxy, and halogen.

In one alternative, such compounds are described wherein $R^d$ and $R^e$ are each independently selected from the group consisting of $C_{1-9}$alkyl, $C_{1-6}$alkoxyalkyl, aryl, and heteroaryl, where each of said aryl or heteroaryl groups is optionally substituted with one or more substituents independently selected from the group consisting of $C_{1-6}$alkyl, haloalkyl, $C_{1-6}$alkoxy, and halogen; $R^2$ is $C_{1-6}$alkyl; $R^3$ and $R^4$ are hydrogen; and Ar is a 2,4-disubstituted, 2,6-disubstituted, or 2,4,6-trisubstituted pyridin-3-yl, and the substituents are independently selected from the group consisting of $C_{1-6}$alkyl, $C_{1-6}$alkoxy, halogen, haloalkyl, and $-NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-NR^aR^b$; $-C(O)NR^aR^b$; or $-CR^cR^dR^e$, where $R^c$ is $-NR^{a''}R^{b'''}$; $R^d$ and $R^e$ are each independently selected from the group consisting of hydrogen and $C_{1-9}$alkyl; and $R^a$, $R^b$, $R^{a'''}$, and $R^{b'''}$ are as defined above.

In one alternative, such compounds are described wherein $R^a$, $R^b$, $R^{a'''}$, and $R^{b'''}$ are each independently selected from the group consisting of hydrogen, $C_{1-9}$alkyl, hydroxyalkyl, $C_{1-6}$alkoxyalkyl, $C_{3-6}$cycloalkylalkyl, heterocyclylalkyl, arylalkyl, and heteroarylalkyl, wherein each of said aryl or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In another alternative, such compounds are described wherein $R^a$ and $R^b$, or $R^{a'''}$ and $R^{b'''}$, are taken together with the nitrogen to which they are attached form an heterocyclyl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, and imidazoline, where each of said rings is optionally substituted with one or more substituents independently selected from the group consisting of hydroxy, oxo, alkyl, aminoalkyl, acyl, acylamino, aminocarbonyl, aminocarbonylalkyl, and aminocarbonylamino, and each of said amino groups is optionally monosubstituted or disubstituted with alkyl, or is contained in a pyrrolidinyl, piperidinyl, morpholinyl, or piperazinyl group.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-NR^aR^b$; $R^a$ is selected from the group consisting of hydrogen, $C_{1-9}$alkyl, and $C_{1-6}$alkoxyalkyl; and $R^b$ is selected from the group consisting of $C_{1-9}$alkyl, hydroxyalkyl, $C_{1-6}$alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In one alternative, such compounds are described, wherein $R^2$ is $C_{1-6}$alkyl; $R^3$ and $R^4$ are hydrogen; and Ar is a 2,4-disubstituted, 2,6-disubstituted, or 2,4,6-trisubstituted pyridin-3-yl, and the substituents are independently selected from the group consisting of $C_{1-6}$alkyl, $C_{1-6}$alkoxy, halogen, haloalkyl, and $-NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-CR^cR^dR^e$; $R^c$ is $-NR^{a'''}R^{b'''}$; $R^d$ and $R^e$ are each independently selected from the group consisting of hydrogen and $C_{1-9}$alkyl; $R^{a'''}$ is selected from the group consisting of hydrogen, $C_{1-9}$alkyl, and $C_{1-6}$alkoxyalkyl; and $R^{b'''}$ is selected from the group consisting of $C_{1-9}$alkyl, hydroxyalkyl, $C_{1-6}$alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In one alternative, such compounds are described wherein $R^2$ is $C_{1-6}$alkyl; $R^3$ and $R^4$ are hydrogen; and Ar is a 2,4-disubstituted, 2,6-disubstituted, or 2,4,6-trisubstituted pyridin-3-yl, and the substituents are independently selected from the group consisting of $C_{1-6}$alkyl, $C_{1-6}$alkoxy, halogen, haloalkyl, and $-NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is $-OR^a$, and $R^a$ is as defined above.

In one alternative, such compounds are described wherein $R^a$ is selected from the group consisting of $C_{1-9}$alkyl, $C_{1-6}$alkoxyalkyl, $C_{3-6}$cycloalkylalkyl, arylalkyl, and heteroarylalkyl, wherein each of said cycloalkyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl.

In another alternative, such compounds are described wherein $R^2$ is $C_{1-6}$alkyl; $R^3$ and $R^4$ are hydrogen; and Ar is a 2,4-disubstituted, 2,6-disubstituted, or 2,4,6-trisubstituted pyridin-3-yl, and the substituents are independently selected from the group consisting of $C_{1-6}$alkyl, $C_{1-6}$alkoxy, halogen, haloalkyl, and $-NR^{a''}R^{b''}$, where $R^{a''}$ and $R^{b''}$ are each independently selected from the group consisting of hydrogen and $C_{1-9}$alkyl.

In another embodiment, compounds of Formula III are described, wherein $R^3$ and $R^4$ are each independently selected from hydrogen and methyl, Ar is a di- or tri-substituted pyridinyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$alkyl, and $C_{1-9}$alkylcarbonyl, the integer n is 1 or 2, $R^2$ is as defined above; and $R^1$ is aryl or heteroaryl, where said aryl or heteroaryl is optionally substituted with one or more substituents independently selected from $C_{1-6}$alkyl, $C_{1-6}$alkoxy, $C_{1-6}$alkylthio, $C_{1-6}$alkylsulfonyl, halogen, haloalkyl, cyano, nitro, and $-NR^{a'}R^{b'}$, where $R^{a'}$ and $R^{b'}$ are each independently selected from the group consisting of hydrogen, $C_{1-9}$alkyl, and $C_{1-9}$alkylcarbonyl.

In one alternative, such compounds are described wherein the aryl or heteroaryl is optionally substituted with one or more substituents independently selected from $C_{1-6}$alkyl, $C_{1-6}$alkoxy, halogen, haloalkyl, cyano, and —NR$^{a'}$R$^{b'}$, where R$^{a'}$ and R$^{b'}$ are each independently selected from the group consisting of hydrogen, $C_{1-9}$alkyl, and $C_{1-9}$alkylcarbonyl.

The invention further relates to pharmaceutical compositions containing a therapeutically effective amount of at least one compound of Formula I or Formula II, or individual isomers, racemic or non-racemic mixtures of isomers, or pharmaceutically acceptable salts or solvates thereof, in admixture with at least one suitable carrier.

The invention further relates to a method of treating a subject that has a disease state that is alleviated by treatment with a CRF receptor antagonist, wherein said method comprises administering to said subject a therapeutically effective amount of the compound of Formula I or Formula II.

In one embodiment, a method of treating a subject that has a disease state comprising disorders of the CNS is described herein. In another embodiment, a method of treating a subject with a disease state comprising phobias, stress related illnesses, mood disorders, eating disorders, generalized anxiety disorders, stress induced gastrointestinal dysfunctions, neurodegenerative diseases, or neuropsychiatric disorders is described herein.

The invention further relates to a process for preparing a compound of Formula I, where a is a single bond, comprising:

(a) treating a compound of formula:

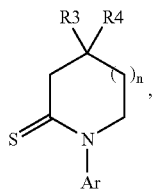

where R$^3$, R$^4$, and Ar are as defined in claim 1, with a compound of formula:

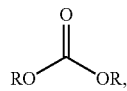

where R is alkyl, to form a first intermediate of formula:

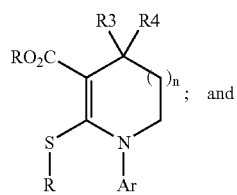

(b) treating the first intermediate with a compound of formula:

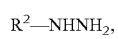

R$^2$—NHNH$_2$, where R$^2$ is as defined in claim 1, to form a second intermediate of formula:

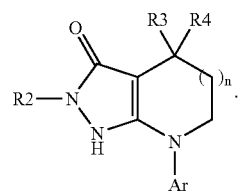

In one embodiment, the process further comprises (c) treating the second intermediate with a compound of formula:

R$^a$—OH, where R$^a$ is as defined in claim 1, to form a compound of Formula I, wherein R$^1$ is —OR$^a$.

In one alternative, the process further comprises (c) treating the second intermediate with a brominating reagent to form a third intermediate of formula:

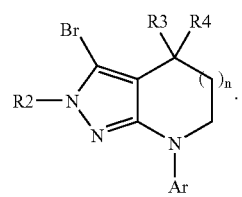

In another embodiment, the process further comprises (d) converting the third intermediate into an anion of formula:

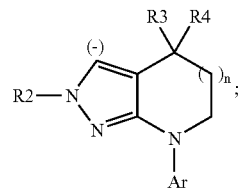

and (e) treating the anion with a compound of formula:

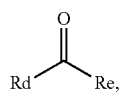

where Rd and Re are as defined in claim 1, to form a compound of Formula I, wherein R$^1$ is —CR$^c$R$^d$R$^e$, and R$^c$ is hydroxy.

In one alternative, the process, further comprises (e) treating the anion with a compound of formula:

C(O)$_2$, to form a compound of Formula I, wherein R$^1$ is —CO$_2$R$^a$.

In another embodiment, the process further comprises (d) treating the third intermediate with a compound of formula:

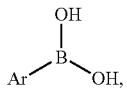

where Ar' is aryl or heteroaryl, where each aryl or heteroaryl is optionally substituted with one or more substituents independently selected from $C_{1-6}$alkyl, $C_{1-6}$alkoxyl $C_{1-6}$alkylthio, $C_{1-6}$alkylsulfonyl, halogen, haloalkyl, cyano, nitro, and $-NR^{a'}R^{b'}$, where $R^{a'}$ and $R^{b'}$ are each independently selected from the group consisting of hydrogen, $C_{1-9}$alkyl, and $C_{1-9}$alkylcarbonyl, to form a compound of Formula I, wherein $R^1$ is aryl or heteroaryl, where each aryl or heteroaryl is optionally substituted with one or more substituents independently selected from $C_{1-6}$alkyl, $C_{1-6}$alkoxy, $C_{1-6}$alkylthio, $C_{1-6}$alkylsulfonyl, halogen, haloalkyl, cyano, nitro, and $-NR^{a'}R^{b'}$, where $R^{a'}$ and $R^{b'}$ are each independently selected from the group consisting of hydrogen, $C_{1-9}$alkyl, and $C_{1-9}$alkylcarbonyl.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" or "lower alkyl" means a monovalent linear or branched saturated hydrocarbon radical, consisting solely of carbon and hydrogen atoms, having from one to six carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, and the like.

"Alkylene" means a divalent linear or branched saturated hydrocarbon radical consisting solely of carbon and hydrogen atoms, having from one to six carbon atoms inclusive, unless otherwise indicated. Examples of alkylene radicals include, but are not limited to, methylene, ethylene, propylene, 2-methylethylene, 3-methylpropylene, 2-ethylethylene, pentylene, hexylene, and the like "Alkoxy" means a radical —OR, wherein R is a lower alkyl radical as defined herein. Examples of alkoxy radicals include, but are not limited to, methoxy, ethoxy, isopropoxy, and the like.

"Alkoxyalkyl" denotes one or more alkoxy group(s) as defined above which is (are) bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl,1,4-dimethoxypropyl, including their isomers. $C_{1-6}$ alkoxyalkyl denotes a group wherein the alkyl portion is comprised of 1–6 carbon atoms exclusive of carbon atoms in the alkoxy portion of the group.

"Cycloalkyl" means a monovalent saturated carbocyclic radical consisting of one or more rings, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino, unless otherwise indicated. Examples of cycloalkyl radicals include, but are not limited to, cyclopropyl, cyclobutyl, 3-ethylcyclobutyl, cyclopentyl, cycloheptyl, and the like.

"Cycloalkylalkyl" means a radical —R'R", wherein R' is an alkylene radical, and R" is a cycloalkyl radical as defined herein. Examples of cycloalkylalkyl radicals include, but are not limited to, cyclopropylmethyl, cyclohexylmethyl, cyclopentylethyl, and the like.

"Cycloalkenyl" means a monovalent unsaturated carbocyclic radical consisting of one or more rings, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino, unless otherwise indicated. Examples of cycloalkenyl radicals include, but are not limited to, cyclobuten-1-yl, 3-ethylcyclobuten-1-yl, cyclopenten-1-yl, 3-fluorocyclohepten-1-yl, and the like.

"Halogen" or "halo" means the radical fluoro, bromo, chloro, or iodo, and combinations thereof.

"Haloalkyl" means a lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Aryl" means a monocyclic or bicyclic radical of 6 to 12 ring carbon atoms having at least one aromatic ring, with the understanding that the attachment point of the aryl radical will be on an aromatic ring. The aryl radical is optionally substituted independently with one or more substituents, preferably one to three substituents, selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —SO2NR'R" (where R' and R" are independently hydrogen or alkyl), alkoxy, haloalkoxy, alkoxycarbonyl, carbamoyl, hydroxy, halo, nitro, cyano, thio, methylenedioxy or ethylenedioxy. More specifically the term aryl includes, but is not limited to, phenyl, naphthyl, tetrahydronaphthyl, 3,4-methylenedioxyphenyl, 1,2,3,4-tetrahydroquinolin-7-yl, 1,2,3,4-tetrahydroisoquinoline-7-yl, and the like.

"Heteroaryl" means a monocyclic or bicyclic radical of 5 to 12 ring atoms having at least one aromatic ring containing one, two, or three ring heteroatoms selected from nitrogen, oxygen, and sulfur, the remaining ring atoms being carbon, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —SO$_2$NR'R" (where R' and R" are independently hydrogen or alkyl), alkoxy, haloalkoxy, alkoxycarbonyl, carbamoyl, hydroxy, halo, nitro, cyano, thio, methylenedioxy or ethylenedioxy. More specifically the term heteroaryl refers to monocyclic aromatic moieties having 5 to 6 ring atoms, including 1 to 2 heteroatoms, and includes, but is not limited to, pyridinyl, furanyl, thienyl, thiazolyl, isothiazolyl, triazolyl, imidazolyl, isoxazolyl, pyrrolyl, pyrazolyl, and pyrimidinyl, and derivatives thereof. In addition, the term heteroaryl refers to bicyclic aromatic moieties having 9 to 10 ring atoms, including 1 to 3 heteroatoms, and includes, but is not limited to, benzofuranyl, tetrahydrobenzofuranyl, isobenzofuranyl, benzothiazolyl, benzoisothiazolyl, benzotriazolyl, indolyl, isoindolyl, benzoxazolyl, quinolinyl, 5,6,7,8-tetrahydroquinolinyl, isoquinolinyl, 5,6,7,8-tetrahydroisoquinolinyl, benzimidazolyl, benzisoxazolyl, and benzothienyl, and derivatives thereof.

"Heteroalkyl" means an alkyl radical as defined herein wherein one, two, or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; and R$^b$ and R$^c$ are independently selected from the group consisting of hydrogen, acyl, alkyl, cycloalkyl, or cycloalkylalkyl; and when n is 0, R$^d$ is hydrogen, alkyl, cycloalkyl, and cycloalkylalkyl. When n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-methoxyethyl, 2-ethoxyethyl, 3-methoxypropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heterocyclyl" means a saturated or unsaturated nonaromatic monocyclic or bicylic radical of 3 to 10 ring atoms in which one or two ring atoms are heteroatom containing groups selected from NR', O, or S(O)$_n$ (where R' is alkyl, heteroalkyl, or hydrogen, and n is an integer from 0 to 2), the remaining ring atoms being carbon. The heterocyclyl radical is optionally substituted with one or more substituents selected from the group consisting of hydroxy, oxo, alkyl, haloalkyl, hydroxyalkyl, heteroalkyl, and acyl. The term heterocyclyl includes, but is not limited to, tetrahydropyranyl, piperidino, tetrahydropyrimidin-5-yl, tetrahydropyrimidin-1-yl, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, tetrahydroquinolin-1-yl and tetrahydroisoquinolin-2-yl, and the like.

"Arylalkyl" means a radical —R'R'' where R' is an alkylene radical and R'' is an aryl radical as defined herein. Examples of arylalkyl radicals include, but are not limited to, 4-fluorophenylmethyl, 3,4-dichlorophenylethyl, and the like.

"Heteroarylalkyl" means a radical —R'R'' where R' is an alkylene radical and R'' is an heteroaryl radical as defined herein. Examples of heteroarylalkyl radicals include, but are not limited to, such as 3-pyridinylmethyl, 4-chloropyrimidin-2-ylmethyl, 2-thiophen-2-ylethyl, and the like.

"Heterocyclylalkyl" means a radical —R'R'' where R' is an alkylene radical and R'' is an heterocyclyl radical as defined herein. Examples of heterocyclylalkyl radicals include, but are not limited to, tetrahydropyran-2-ylmethyl, 2-piperidinylmethyl, 3-piperidinylmethyl, morpholin-1-yl-propyl, and the like.

"Alkylamino" means a radical —NR'R'', wherein R' is hydrogen or alkyl, and R'' is an alkyl radical as defined herein. Examples of alkylamino radicals include, but are not limited to, methylamino, ethylamino, cyclopropylmethylamino, dicyclopropylmethylamino, dimethylamino, methylethylamino, diethylamino, di(1-methylethyl)amino, and the like.

"Acyl" means a formyl radical of the formula —C(O)H, or a carbonyl radical of the formula —C(O)R', where R' is selected from the group consisting of $C_{1-18}$alkyl, alkoxyalkyl, cycloalkyl, cycloalkylalkyl, haloalkyl, heteroalkyl, heterocyclyl, heterocyclylalklyl, aryl, arylalkyl, heteroaryl, heteroarylalkyl, alkoxy, or amino, as defined herein, where said amino is optionally monosubstituted or disubstituted with alkyl, or said amino is contained in a pyrrolidinyl, piperidinyl, morpholinyl, or piperazinyl group.

"Alkylidenyl" means a bivalent radical =CRR', wherein R and R' are independently an alkyl radical or hydrogen, as defined herein. Examples of alkylidenyl radicals include, but are not limited to, ethylidenyl, propylidenyl, butylidenyl, and the like.

"Cycloalkylidenyl" means a bivalent radical =CRR', wherein R and R' are taken together with the carbon to which they are attached to form a bivalent cycloalkyl radical, as defined herein. Examples of cycloalkylidenyl radicals include, but are not limited to, cyclopentylidenyl, 3-fluoro-cyclohexylidenyl, and the like.

"Cycloalkyl-alkylidenyl" means a bivalent radical =CRR', wherein R is an alkyl radical or hydrogen, and R' is a cycloalkyl radical, as defined herein. Examples of cycloalkyl-alkylidenyl radicals include, but are not limited to, cyclopropylmethylidenyl, cyclohexylmethylidenyl, 1-cyclopentylethylidenyl, and the like.

"Cycloalkylalkyl-alkylidenyl" means a bivalent radical =CRR', wherein R is an alkyl radical or hydrogen, and R' is a cycloalkylalkyl radical, as defined herein. Examples of cycloalkylalkyl-alkylidenyl radicals include, but are not limited to, 2-cyclopentylethylidenyl, 1-cyclohexylpropyl-liden-2-yl, and the like.

"Heteroalkylidenyl" means a bivalent radical =CRR', wherein R is an heteroalkyl radical, an haloalkyl radical, an alkyl radical, or hydrogen, and R' is an heteroalkyl radical or an haloalkyl radical, as defined herein. Examples of heteroalkylidenyl radicals include, but are not limited to, 3,3,3-trifluoropropylidenyl, 2-hydroxybutylidenyl, 3-aminopropylidenyl, and the like.

"Heterocyclylidenyl" means a bivalent radical =CRR', wherein R and R' are taken together with the carbon to which they are attached to form a bivalent heterocyclyl radical, as defined herein. Examples of heterocyclylidenyl radicals include, but are not limited to, pyrrolidinyliden-2-yl, tetrahydropyranyliden-4-yl, piperidinyliden-4-yl, and the like.

"Heterocyclyl-alkylidenyl" means a bivalent radical =CRR', wherein R is an alkyl radical or hydrogen, and R' is an heterocyclyl radical, as defined herein. Examples of heterocyclyl-alkylidenyl radicals include, but are not limited to, 4-piperidinylmethylidenyl, 4-methyl-1-piperazinylmethylidene, and the like.

"Heterocyclylalkyl-alkylidenyl" means a bivalent radical =CRR', wherein R is an alkyl radical or hydrogen, and R' is an heterocyclylalkyl radical, as defined herein. Examples of heterocyclylalkyl-alkylidenyl radicals include, but are not limited to, 2-(tetrahydropyran-4-yl)ethylidenyl, 1-(piperidin-3-yl)propyliden-2-yl, and the like.

"Arylalkylidenyl" means a bivalent radical =CRR', wherein R is an aryl radical, an alkyl radical, or hydrogen, and R' is an aryl radical, as defined herein. Examples of arylalkylidenyl radicals include, but are not limited to, 4-chlorophenylmethylidenyl, 6,7-dimethoxynaphth-2-ylmethylidenyl, and the like.

"Arylalkyl-alkylidenyl" means a bivalent radical =CRR', wherein R is an alkyl radical or hydrogen, and R' is an arylalkyl radical, as defined herein. Examples of arylalkyl-alkylidenyl radicals include, but are not limited to, 2-(4-trifluoromethylphenyl)ethylidenyl, 1-(3,4-dichlorophenyl)propyliden-2-yl, and the like.

"Heteroarylalkylidenyl" means a bivalent radical =CRR', wherein R is an alkyl radical or hydrogen, and R' is an heteroaryl radical, as defined herein. Examples of heteroarylalkylidenyl radicals include, but are not limited to, 3-pyridinylmethylidenyl, 4-chloro-2-pyrimidinylmethylidenyl, and the like.

"Heteroarylalkyl-alkylidenyl" means a bivalent radical =CRR', wherein R is an alkyl radical or hydrogen, and R' is an heteroarylalkyl radical, as defined herein. Examples of heteroarylalkyl-alkylidenyl radicals include, but are not limited to, 2-(4-trifluoromethylpyrimidinyl)ethylidenyl, 1-(thiophen-2-yl)propyliden-2-yl, and the like.

"Phenylsulfonyl" means a monovalent radical $C_6H_5SO_2$—. A phenyl group can be unsubstituted or substituted with one or more suitable substituents.

"Alkoxycarbonyl" means a monovalent radical —C(O)—OR, wherein R is a lower alkyl radical as defined herein. Examples of alkoxycarbonyl radicals include, but are not limited to, methoxycarbonyl, ethoxycarbonyl, butoxycarbonyl, and the like.

"Alkoxyalkylcarbonyl" means a monovalent radical —C(O)—R—OR', wherein R is an alkylene radical as defined herein and R' is a lower alkyl radical as defined herein. Examples of alkoxyalkylcarbonyl radicals include, but are not limited to, methoxymethylcarbonyl, ethoxymethylcarbohyl, and the like.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively include hydroxyl groups protected as acetates, haloalkyl carbonates, benzyl ethers, alkylsilyl ethers, heterocyclyl ethers, methyl or alkyl ethers, and the like. Protective or blocking groups for carboxyl groups are similar to those described for hydroxyl groups, and are preferably tert-butyl, benzyl or methyl esters.

"Amino-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by exposure to mild acids in the case of BOC, e.g., trifluoroacetic acid or hydrochloric acid in ethyl acetate as a solvent; or by catalytic hydrogenation in the case of CBZ.

"Hydroxy-protecting group" means the protecting group that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring. Other suitable hydroxy-protecting groups include alkyl ether groups, the tetrahydropyranyl, silyl, trialkylsilyl ether groups, and the allyl group.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956,12, 81; Cahn, *J. Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

"Substantially pure" means at least about 90 mole percent, more preferably at least about 95 mole percent, and most preferably at least about 98 mole percent of the desired enantiomer or stereoisomer is present compared to other possible configurations.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I or Formula II are prepared by modifying one or more functional group(s) present in the compound of Formula I or Formula II in such a way that the modification(s) may be cleaved in vivo to release the parent compound. Prodrugs include compounds of Formula I or Formula II wherein a hydroxy, amino, sulfhydryl, carboxy or carbonyl group in a compound of Formula I or Formula II is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), .esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I or Formula II, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp. 352–401; *Design of Prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Disease state" means any disease, condition, symptom, or indication.

"Treating" or "treatment" of a disease state includes:
(1) preventing the disease state, i.e. causing the clinical symptoms of the disease state not to develop in a subject that may be exposed to or predisposed to the disease state, but does not yet experience or display symptoms of the disease state;
(2) inhibiting the disease state, i.e., arresting the development of the disease state or its clinical symptoms, or
(3) relieving the disease state, i.e., causing temporary or permanent regression of the disease state or its clinical symptoms.

"Mood disorders" or "affective disorders" means psychopathologic conditions in which a pervasive disturbance of mood constitutes the core manifestation. These terms subsume anxiety and related neuroses, especially the depressive form. Examples of "mood disorders" or "affective disorders" include, but are not limited to, depression, major depressive disorder, single episode depression, recurrent depression, child abuse induced depression, postpartum depression, dysthemia, unipolar disorder, bipolar disorder with manifestations of insomnia and eating disorder, dysthymic disorder, double depression, morbid and clinical depression, mania and cyclothymia.

Nomenclature

In general, the nomenclature used in this Application is based on AUTONOM™ v.4.0, a Beilstein Institute computerized system for the generation of IUPAC systematic nomenclature.

For example, a compound of Formula I wherein $R^1$ is 4-hydroxyheptan-4-yl, $R^2$ is methyl, $R^3$, and $R^4$ are hydrogen, Ar is 2-chloro-4,6-dimethyl-phenyl, and n is 1 is named 4-[7-(2-chloro-4,6-dimethyl-phenyl)-2-methyl-4,5,6,7-tetrahydro-2H-pyrazolo[3,4-b]pyridin-3-yl]-heptan-4-ol.

General Utility

The compounds of this invention are CRF antagonists, and as such are expected to be effective in the treatment of a wide range of stress-related illnesses, mood disorders such as depression, major depressive disorder, single episode depression, recurrent depression, child abuse induced depression, postpartum depression, dysthemia, bipolar disorder and cyclothymia; chronic fatigue syndrome; eating disorders such as obesity, anorexia and bulimia nervosa; generalized anxiety disorder; panic disorder; phobias; obsessive-compulsive disorder; post-traumatic stress disorder; pain perception such as fibromyalgia; headache; stress-induced gastrointestinal dysfunction such as irritable bowel syndrome (IBS), colonic hypersensitivity or spastic colon; hemorrhagic stress; ulcers; stress-induced psychotic episodes; inflammatory disorders such as rheumatoid arthritis and osteoarthritis; asthma; psoriasis; allergies; premature birth; hypertension; congestive heart failure; sleep disorders; neurodegenerative diseases such as Alzheimer's disease, senile dementia, Parkinsons's disease and Huntington's disease; head or spinal cord trauma; ischemic neuronal damage; excitotoxic neuronal damage; epilepsy; stroke; psychosocial dwarfism; chemical dependencies and addictions; drug and alcohol withdrawal symptoms; stress-induced immune dysfunctions; immune suppression and stress-induced infections; cardiovascular or heart related diseases; fertility problems; and/or human immunodeficiency virus infections.

These and other therapeutic uses are described, for example, in Goodman & Gilman's, The Pharmacological Basis of Therapeutics, ninth edition, McGraw-Hill, New York, 1996, Chapter 26:601–616; and Coleman, R. A., Pharmacological Reviews, 1994, 46:205–229.

Testing

The pharmacology of the compounds of this invention was determined by art recognized procedures. The CRF receptor binding affinity of test compounds can be determined by the intracellular CRF stimulated cAMP activity assay and the CRF Receptor Binding Assay as described in more detail in Example 3 and 4 respectively.

Compound Preparation

The compounds of Formulae I and II described herein may be prepared by standard synthetic methods. In particular, certain compounds of Formulae I and II may be prepared from intermediate bromopyrazole 7, the preparation of which is illustrated in Scheme 1 for Formula I, where $R^2$, $R^3$, $R^4$, and n are as described above, and Ar, as described above, is for example phenyl optionally-substituted with one or more groups X.

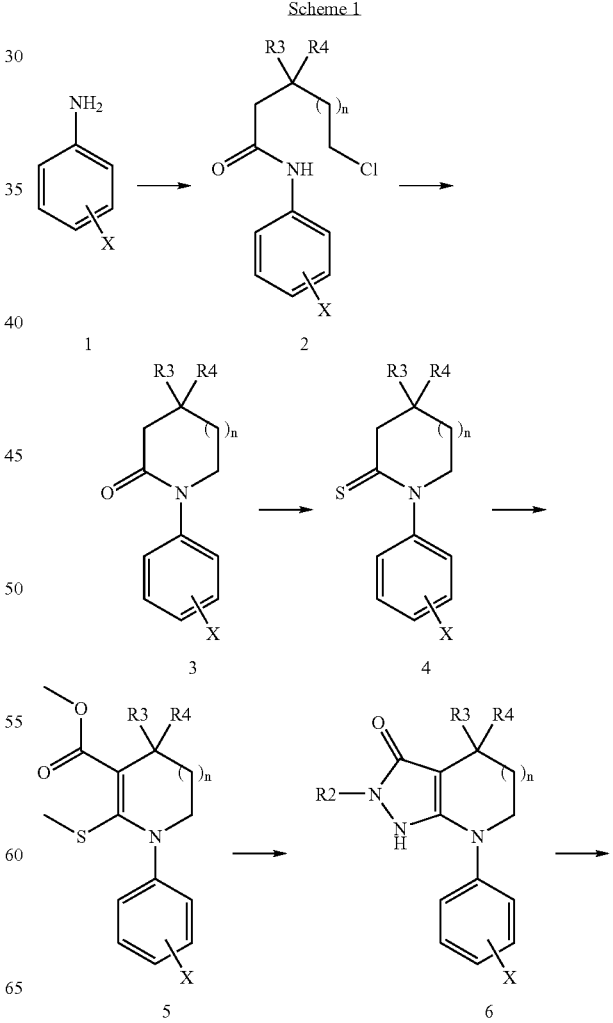

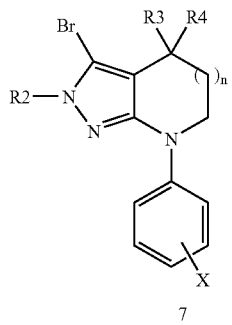

According to Scheme 1, optionally substituted aniline 1 is acylated with a carboxylic acid derivative, optionally substituted with groups $R^3$ and $R^4$, having an ω-leaving group, such as halogen, to provide amide 2, which is subsequently cyclized under basic conditions onto the carbon possessing the leaving group to generate 3. Anilide lactam 3 is converted into the corresponding thione 4, deprotonated, C-acylated, and concurrently S-methylated to form methyl carboxylate 5. Treatment of 5 with $R^2$-substituted hydrazine provides pyrazolinone-fused heterocycle 6, which is brominated to provide bromopyrazole 7. The pyrazole-fused heterocycles can also be similarly prepared with an aminoheteroaryl in place of the aniline. For example, compound 12d (Table 7) is prepared starting from 2-dimethylamino-4-methyl-5-amino pyridine (T. Ebara et al. JP54028330 [CAN 91:40904])

Intermediate bromopyrazole 7 is converted into the compounds of Formulae I and II, as illustrated in Scheme 2 for Formula I, where $R^2$, $R^3$, $R^4$, $R^d$, $R^e$, and n are as described above, and Ar, as described above, is for example phenyl optionally-substituted with one or more groups X.

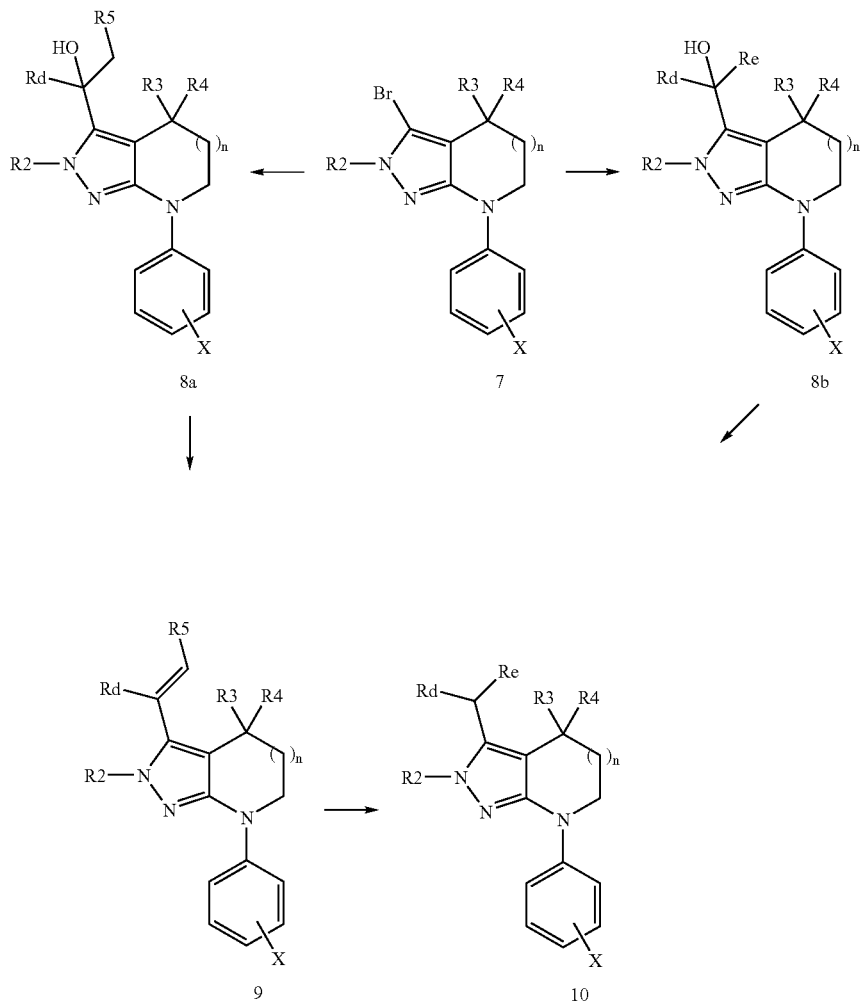

According to Scheme 2, intermediate bromopyrazole 7 is metallated and reacted with an $R^d,R^5$-substituted aldehyde or ketone to provide alcohol 8a which may be eliminated to the corresponding alkene 9. It is appreciated that depending upon the reaction conditions, and the nature of $R^d$ and $R^5$, the double bond stereochemistry resulting from the elimination reaction to alkene.9 may be either an E-double bond, a Z-double bond, or a mixture of both in various ratios. Subsequent reduction of alkene 9, by hydrogenation for example, provides alkane 10. It is understood that $R^e$ as defined above corresponds to $CH_2$—$R^5$ or CH—$R^5$ of alcohol 8a or alkene 9, respectively. Alternatively, bromopyrazole 7 is metallated and reacted with an $R^d,R^e$-substituted aldehyde or ketone to provide alcohol 8b which may be deoxygenated, under radical conditions for example, to provide alkane 10.

Alternatively, intermediate bromopyrazole 7 is converted into the compounds of Formulae I and II, as illustrated in Scheme 3 for Formula I, where $R^2$, $R^3$, $R^4$, $R^a$, $R^b$, and n are as described above, and Ar, as described above, is for example phenyl optionally-substituted with one or more groups X.

Scheme 3

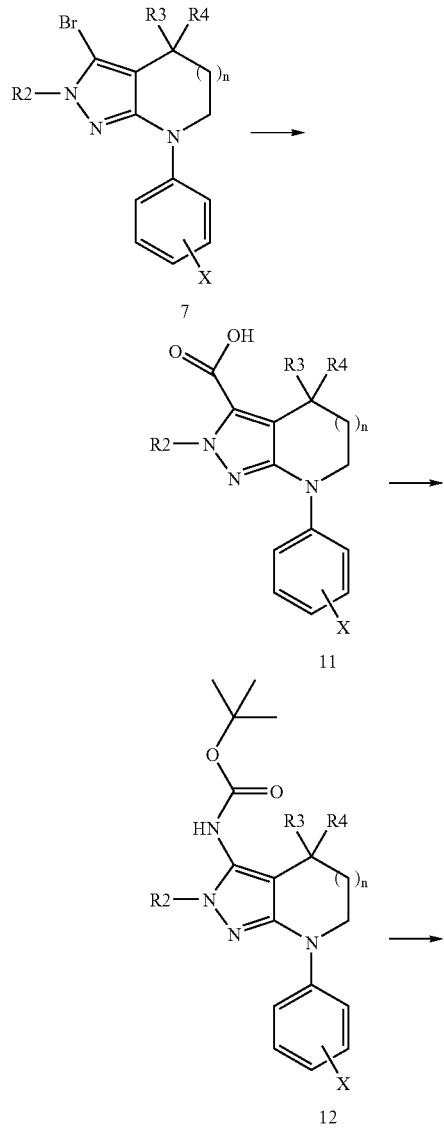

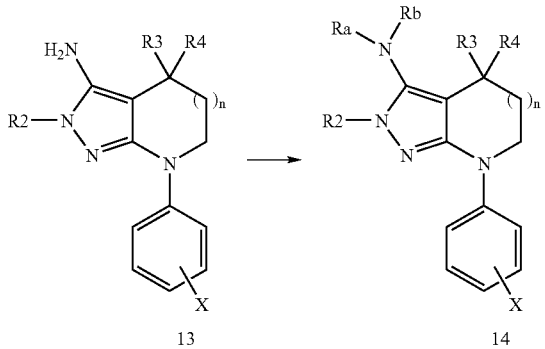

According to Scheme 3, intermediate bromopyrazole 7 is metallated and reacted with carbon dioxide, or a carbon dioxide equivalent, to provide carboxylic acid 11. Acid 11 is converted to the corresponding amine 13 via an amide rearrangement, such as by the Curtius, Lossen, or Schmidt reaction, or as illustrated in Scheme 3 by the Hofmann reaction involving intermediate carbamate 12. Amine 13 is converted into the mono- or disubstituted amine 14 by reductive amination or successive reductive amination, respectively, using an appropriate aldehyde or ketone, and a reducing agent, such as sodium cyanoborohydride, sodium triacetoxyborohydride, and the like. Alternatively, amine 13 is converted into mono- or disubstituted amine 14 via acylation with an appropriate carboxlic acid derivative, such as the corresponding acid chloride, and reduction with an appropriate reducing agent such as diborane, borane-THF complex, and the like. Another alternative conversion of amine 13 to mono- or disubstituted amine 14 is via alkylation with an appropriate alkylating agent, such as methyl iodide, ethyl bromide, and the like, optionally under basic conditions. It is appreciated that each substituent $R^a$ and $R^b$ may be introduced using the same synthetic route described herein, or each substituent may be introduced by a different synthetic route described herein.

Alternatively, intermediate carboxylic acid 11 is converted into the compounds of Formulae I and II, as illustrated in Scheme 4 for Formula I, where $R^2$, $R^3$, $R^4$, $R^a$, $R^b$, and n are as described above, and Ar, as described above, is for example phenyl optionally-substituted with one or more groups X.

Scheme 4

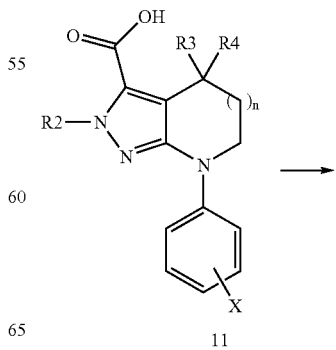

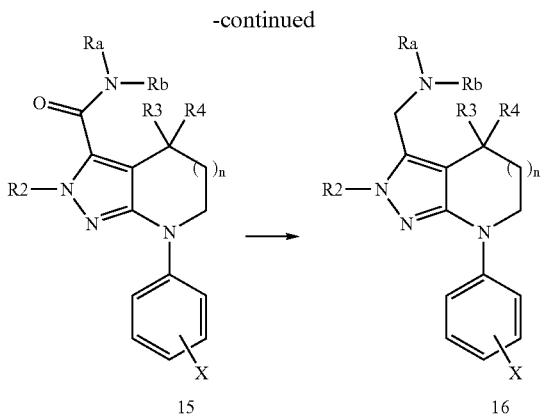

According to Scheme 4, intermediate acid 11 is converted into the corresponding amide 15 and may be further reduced to amine 16.

Alternatively, pyrazolinone-fused heterocyclic 6 is converted into the compounds of Formulae I and II, as illustrated in Scheme 5 for Formula 1, where $R^2$, $R^3$, $R^4$, $R^a$, and n are as described above, and Ar, as described above, is for example phenyl optionally-substituted with one or more groups X.

Scheme 5

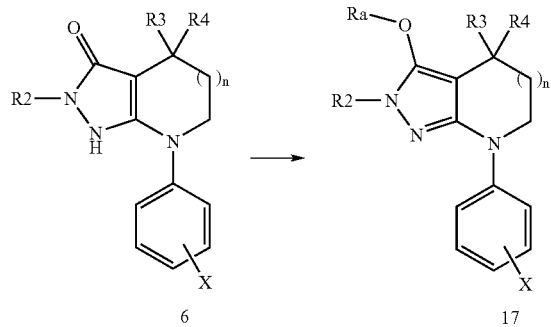

According to Scheme 5, intermediate pyrazolinone-fused heterocycle 6 is converted into the corresponding alkoxy-pyrazole-fused heterocycle 17.

Alternatively, intermediate bromopyrazole 7 is converted into the compounds of Formulae I and II, as illustrated in Scheme 6 for Formula I, where $R^2$, $R^3$, $R^4$, and n are as described above, and Ar, as described above, is for example phenyl optionally-substituted with one or more groups X.

Scheme 6

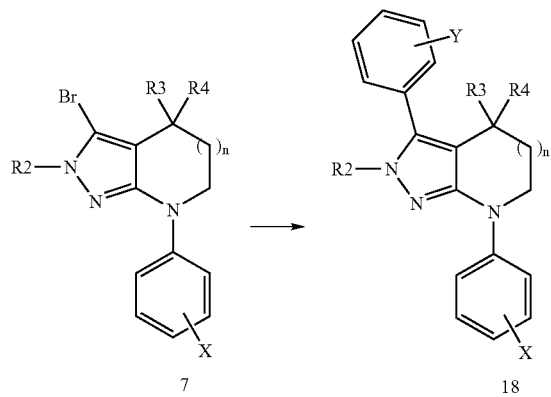

According to Scheme 6, intermediate bromopyrazole 7 is subjected to a metal-catalyzed aryl coupling reaction to provide an aryl pyrazole, as illustrated by, for example phenyl pyrazole 18, optionally substituted with one or more groups Y.

It is understood that the synthetic routes illustrated in Schemes 1–6 are suitable for preparing other compounds of Formulae I and II, including those compounds where Ar, as defined above, is for example naphthyl, pyrimidinyl, or pyridinyl, each of which may be optionally substituted. It is also appreciated that $R^2$ as pertains to the illustrative synthetic sequences of Schemes 1–6 may be a protecting group, as defined above, which may be conveniently removed to provide $R^2$ as hydrogen, or to introduce $R^2$ as alkyl, aryl, acyl, or alkylsulfonyl, as defined above.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gelin the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dode-cylaza-cycloheptan-2-one). Sustained release delivery systems are inserted subcutaneously into to the subdermal layer by surgery or injection. The subderrhal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Example 2.

EXAMPLES

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures), but allowance for some experimental error and deviation, including differences in calibration, rounding of numbers, and the like, is contemplated.

Example 1

3-Bromo-7-(2-chloro-4,6-dimethylphenyl)-2-methyl-4,5,6,7-tetrahydro-2H-pyrazolo[3,4-b]pyridine

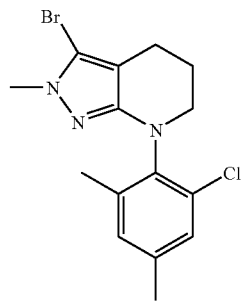

Step 1

5-Chloropentanoic acid (2-chloro-4,6-dimethylphenyl)amide

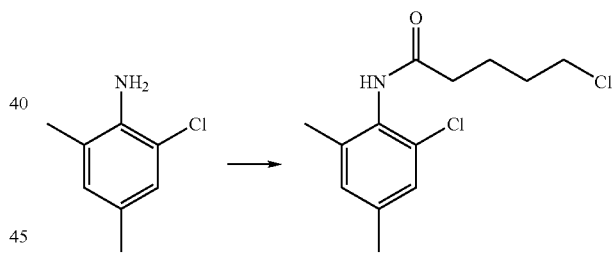

To a solution of 2-chloro-4,6-dimethylaniline (14.7 g) and diisopropylethylamine (18 mL) in 150 mL of THF, was added a solution of 5-chlorovaleryl chloride (12.2 mL) in 75 mL of THF. After the reaction mixture had been allowed to stir at room temperature overnight, it was filtered and the filtrate concentrated on the rotary evaporator. The residue was dissolved in ethyl acetate and washed with 1 M aqueous HCl, saturated aqueous sodium bicarbonate, and brine. The ethyl acetate solution was then dried with magnesium sulfate and concentrated on the rotary evaporator to give a solid which was combined with a 1:1 mixture of hexane and diethyl ether. After this mixture had been stirred for an hour, it was filtered and the collected solids were dried to provide 12.2 g of 5-chloropentanoic acid (2-chloro-4,6-dimethylphenyl)amide, mp 80.6–82.9° C.

Step 2

1-(2-Chloro-4,6-dimethylphenyl)piperidin-2-one

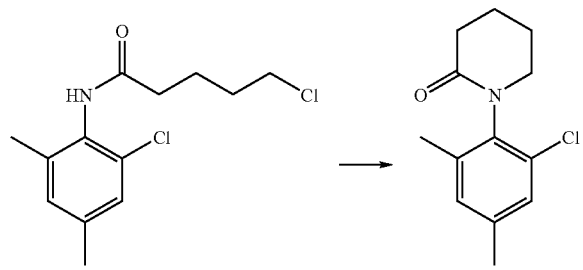

5-Chloropentanoic acid (2-chloro-4,6-dimethylphenyl) amide (21.7 g), potassium t-butoxide (9.34 g), and sodium iodide (1.2 g) were combined in 200 mL t-butanol and the mixture was stirred in a 60° C. oil bath for 3 h. After cooling to room temperature, the reaction mixture was partitioned between ethyl acetate and water. The aqueous phase was washed with additional ethyl acetate. The organic phases were washed with brine, dried with magnesium sulfate, and concentrated to give 18.9 g of 1-(2-chloro-4,6-dimethylphenyl)piperidin-2-one as a solid, mp. 107.7–108.7° C.

Step 3

1-(2-Chloro-4,6-dimethylphenyl)piperidine-2-thione

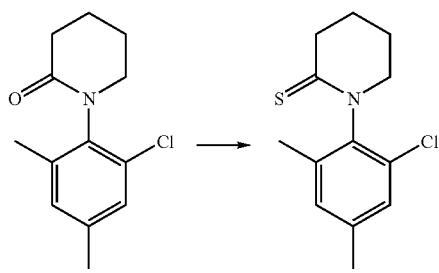

1-(2-Chloro-4,6-dimethylphenyl)piperidin-2-one (18.8 g) and Lawesson's reagent [2,4-bis(4-methoxyphenyl)-1,3-dithia-2,4-diphosphetane-2,4-disulfide] (19.2 g) were combined in 150 mL toluene and the mixture was stirred in an 80° C. oil bath for 3 h. The reaction mixture was then cooled to room temperature and filtered. The filtrate was concentrated on the rotary evaporator and the residue was chromatographed on silica gel, eluting with 9:1 hexane/acetone, to provide 19.4 g of 1-(2-chloro-4,6-dimethylphenyl)piperidine-2-thione, mp 146.8–148.0° C.

Step 4

1-(2-Chloro-4,6-dimethylphenyl)-2-methylsulfanyl-1,4,5,6-tetrahydropyridine-3-carboxylic Acid Methyl Ester

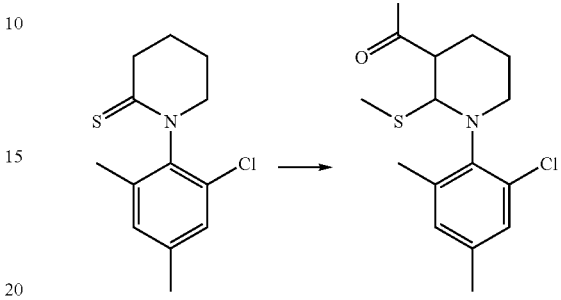

1-(2-Chloro-4,6-dimethylphenyl)piperidine-2-thione (5.11 g), dimethyl carbonate (17.0 mL), sodium hydride (3.7 g of a 60% dispersion in mineral oil), and methanol (0.5 mL) were combined in 100 mL of dioxane and the mixture was stirred in a 120° C. oil bath for 4 h. After the reaction had cooled to room temperature, it was quenched by the addition of aqueous ammonium chloride, diluted with water and washed twice with ethyl acetate. After drying over magnesium sulfate, the ethyl acetate was concentrated and the residue chromatographed on silica gel using an acetone/hexane gradient to provide 5.00 g 1-(2-chloro-4,6-dimethylphenyl)-2-methylsulfanyl-1,4,5,6-tetrahydropyridine-3-carboxylic acid methyl ester, mp 85.3–87.6° C.

Step 5

7-(2-Chloro-4,6-dimethylphenyl)-2-methyl-1,2,4,5,6,7-hexahydropyrazolo-[3,4-b]pyridin-3-one

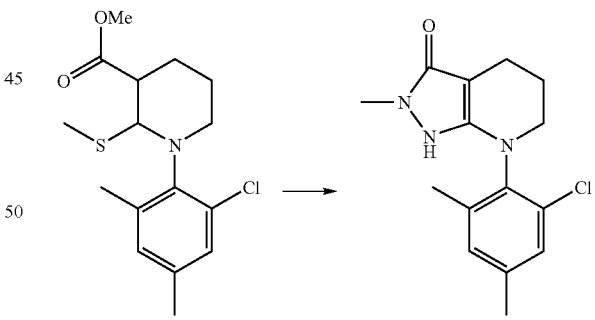

1-(2-Chloro-4,6-dimethylphenyl)-2-methylsulfanyl-1,4,5,6-tetrahydropyridine-3-carboxylic acid methyl ester (4.99 g), methylhydrazine (16.4 mL), p-toluenesulfonic acid monohydrate (2.91 g), and methanol (75 mL) were combined in a glass vessel sealed with a Telfon™ screw cap. The reaction mixture was stirred in a 130° C. oil bath for 24 h, then cooled to room temperature and concentrated on the rotary evaporator. The residue was chromatographed on silica gel using a methanol/dichloromethane gradient to give 3.21 g of 7-(2-chloro-4,6-dimethylphenyl)-2-methyl-1,2,4,5,6,7-hexahydropyrazolo-[3,4-b]pyridin-3-one, mp 95.9–99.9° C.

Step 6

3-Bromo-7-(2-chloro-4,6-dimethylphenyl)-2-methyl-4,5,6,7-tetrahydro-2H-pyrazolo[3,4-b]pyridine 7-(2-Chloro-4,6-dimethylphenyl)-2-methyl-1,2,4,5,6,7-hexahydropyrazolo[3,4-b]pyridin-3-one (3.16 g) and phosphorus oxybromide (15.5 g) were combined and stirred in a 110° C. oil bath for 4 h. After the reaction mixture had cooled to room temperature, it was dissolved in dichloromethane and added to 200 mL of ice/water. This mixture was stirred vigorously for 30 min. The phases were then separated and the aqueous phase was washed with additional dichloromethane. The combined organic phases were washed with aqueous sodium bicarbonate, dried with magnesium sulfate, and concentrated on the rotary evaporator. The residue was chromatographed on silica gel eluting with an acetone/hexane gradient to provide 1.16 g of 3-bromo-7-(2-chloro-4,6-dimethylphenyl)-2-methyl-4,5,6,7-tetrahydro-2H-pyrazolo[3,4-b]pyridine, mp 106–107° C.

Example 2

3-Bromo-7-(2,4-dichlorophenyl)-2-methyl-4,5,6,7-tetrahydro-2H-pyrazolo[3,4-b]pyridine

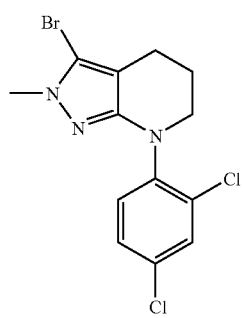

Example 2 was prepared according the procedure described in Example 1, except that 2-chloro-4,6-dimethylaniline was replaced by 2,4-dichloroaniline in step 1, and step 4 was performed as follows:

1-(2,4-Dichlorophenyl)-2-methylsulfanyl-1,4,5,6-tetrahydropyridine-3-carboxylic Acid Methyl Ester

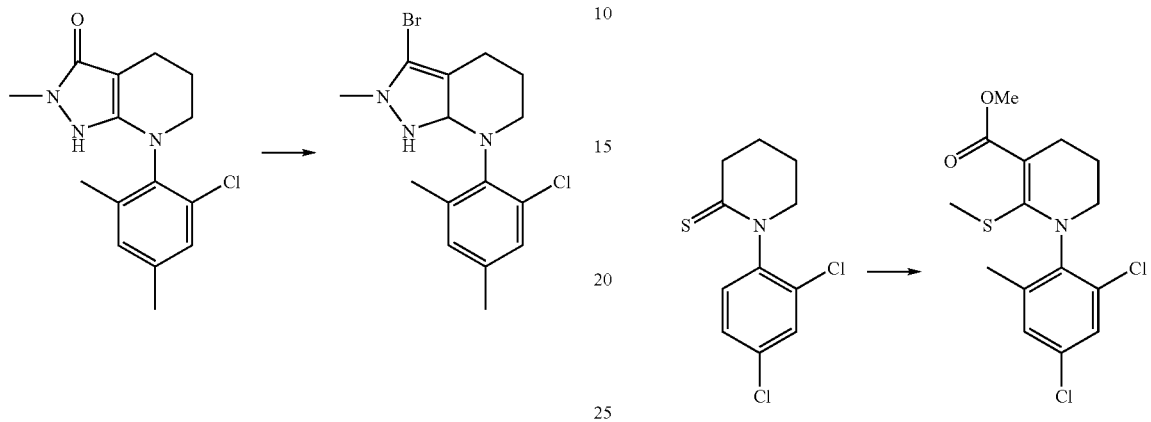

To 39.6 ml of a 3M solution ethylmagnesium bromide in ether was added 100 mL of dry tetrahydrofuran under an atmosphere of nitrogen. Then 16.7 mL of diisopropylamine was added dropwise. The reaction mixture was then heated to 80° C. for 1 h. After cooling to room temperature, the mixture was treated with a solution of 6.19 g of 1-(2,4-dichlorophenyl)piperidine-2-thione in 50 mL of dry tetrahydrofuran, heated to 80° C. for 30 min, and cooled again to room temperature. Then the mixture was treated dropwise with 10.0 mL of dimethylcarbonate and heated to 80° C. for 26 h. After cooling to room temperature, 100 g of ice was added along with 150 mL of 1.2M HCl. The mixture was extracted three times with 100 mL portions of dichloromethane. The combined organic extracts were washed with 100 mL of brine, dried over magnesium sulfate, concentrated, and then kept under high vacuum at 50° C. to remove the higher boiling volatile materials. The residue was purified by flash silica gel chromatography using 7% acetone/hexane as solvent yielding 5.25 g of 1-(2,4-dichlorophenyl)-2-methylsulfanyl-1,4,5,6-tetrahydropyridine-3-carboxylic acid methyl ester as a yellow solid, mp 83–86° C.

Examples 3–4

Example 3 was prepared according to the procedure described in Example 1, except that 2-chloro-4,6-dimethylaniline was replaced by 2,4,6-trimethylaniline in step 1.

Example 4 was prepared according the procedure described in Example 1, except that 2-chloro-4,6-dimethylaniline was replaced by 2,4,6-trimethylaniline, and 5-chlorovaleryl chloride was replaced by 6-chlorocaproyl chloride in step 1.

TABLE 1

Compounds prepared in Examples 1–4.

| Example | Structure | Name | mp (° C.) | MH+ observed (predicted) |
|---|---|---|---|---|
| 1 | 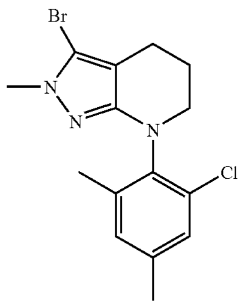 | 3-Bromo-7-(2-chloro-4,6-dimethylphenyl)-2-methyl-4,5,6,7-tetrahydro-2H-pyrazolo[3,4-b]pyridine | 106–107 | 354 (354) |
| 2 | 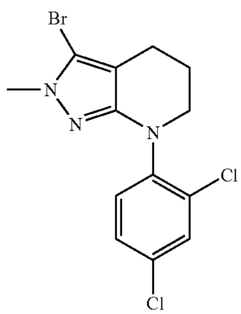 | 3-Bromo-7-(2,4-dichloro-phenyl)-2-methyl-4,5,6,7-tetrahydro-2H-pyrazolo[3,4-b]pyridine | | 360 (360) |
| 3 | 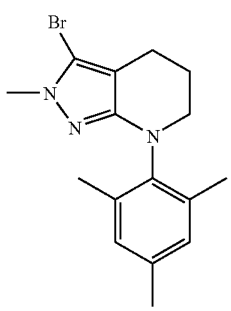 | 3-Bromo-2-methyl-7-(2,4,6-trimethyl-phenyl)-4,5,6,7-tetrahydro-2H-pyrazolo[3,4-b]pyridine | 94.6–97.9 | 334 (334) |
| 4 | 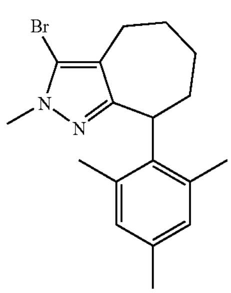 | 3-Bromo-2-methyl-8-(2,4,6-trimethyl-phenyl)-2,4,5,6,7,8-hexahydro-1,2,8-triaza-azulene | | 348 (348) |

Example 5a

4-[7-(2-Chloro-4,6-dimethylphenyl)-2-methyl-4,5,6,7-tetrahydro-2H-gyrazolo-[3,4-b]pyridin-3-yl]heptan-4-ol

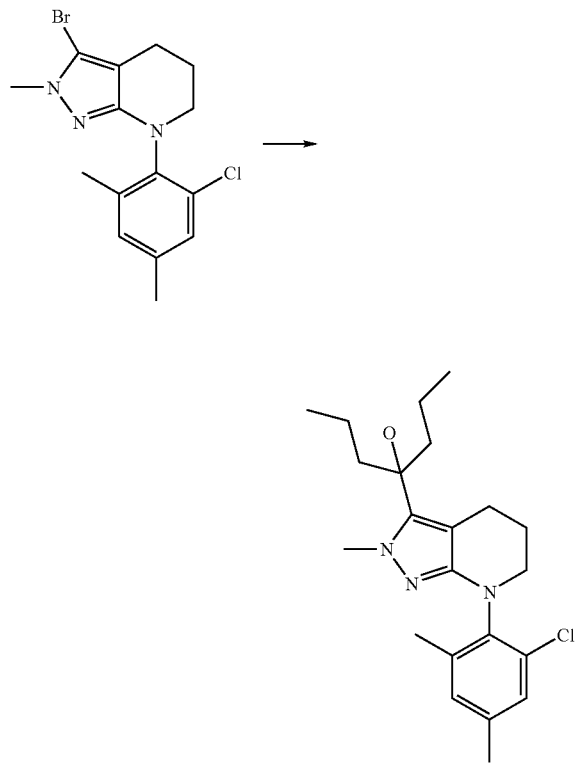

3-Bromo-7-(2-chloro-4,6-dimethylphenyl)-2-methyl-4,5,6,7-tetrahydro-2H-pyrazolo[3,4-b]pyridine (122 mg) and a crystal of 1,10-phenanthroline were dissolved in 3 mL of dry tetrahydrofuran and the solution was chilled to −78° C. under an atmosphere of argon. Then nbutyllithium (2.0 M in cyclohexane) was added until the dark color of the organolithium/phenanthroline complex persisted. An additional 0.17 mL of the butyllithium solution then was added. After 10 min, a solution of 4-heptanone (42.6 mg) in 1 mL tetrahydrofuran was added via syringe. The reaction mixture was allowed to stir at −78° C. for 15 min, then was allowed to warm to 0° C. After quenching with aqueous ammonium chloride, the reaction mixture was partitioned between ethyl acetate and brine. The ethyl acetate was dried with magnesium sulfate and concentrated on the rotary evaporator. The residue was chromatographed on silica gel eluting with 9:1 hexane/acetone to provide 76.0 mg of 4-[7-(2-chloro-4,6-dimethylphenyl)-2-methyl-4,5,6,7-tetrahydro-2H-pyrazolo-[3,4-b]pyridin-3-yl]heptan-4-ol, which was recrystallized from hexane, mp 129–130 ° C.

Examples 5b–5m

Example 5b was prepared according to the procedure described in Example 5a, except that the compound from Example 1 was replaced with the compound from Example 3.

Example 5c was prepared according to the procedure described in Example 5a, except that 4-heptanone was replaced with 1-thienylbutanone and the compound from Example 1 was replaced with the compound from Example 3.

Example 5d was prepared according to the procedure described in Example 5a, except that the compound from Example 1 was replaced with the compound from Example 4.

Example 5e was prepared according to the procedure described in Example 5a, except that the compound from Example 1 was replaced with the compound from Example 2.

Example 5f was prepared according to the procedure described in Example 5a, except that 4-heptanone was replaced with 1,3-bismethoxypropan-2-one and the compound from Example 1 was replaced with the compound from Example 3.

Example 5g was prepared according to the procedure described in Example 5a, except that 4-heptanone was replaced with 1,4-bismethoxybutan-2-one and the compound from Example 1 was replaced with the compound from Example 3.

Example 5h was prepared according to the procedure described in Example 5a, except that 4-heptanone was replaced with 1-thiazol-2-ylpropanone and the compound from Example 1 was replaced with the compound from Example 3.

Example 5i was prepared according to the procedure described in Example 5a, except that 4-heptanone was replaced with 2-furancarboxaldehyde and the compound from Example 1 was replaced with the compound from Example 3.

Example 5j was prepared according to the procedure described in Example 5a, except that 4-heptanone was replaced with propanal and the compound from Example 1 was replaced with the compound from Example 3.

Example 5k was prepared according to the procedure described in Example 5a, except that 4-heptanone was replaced with 1-(1-ethylimidazol-2-yl)butanone and the compound from Example 1 was replaced with the compound from Example 3.

Example 5l was prepared according to the procedure described in Example 5a, except that 4-heptanone was replaced with tetrahydropyran-4-one and the compound from Example 1 was replaced with the compound from Example 3.

Example 5m was prepared according to the procedure described in Example 5a, except that 4-heptanone was replaced with water.

TABLE 2

Compounds prepared in Examples 5.

| Example | Structure | Name | mp (° C.) | MH+ observed (predicted) |
|---|---|---|---|---|
| 5a | 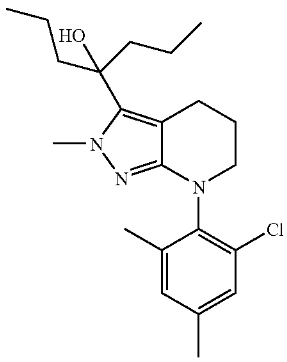 | 4-[7-(2-Chloro-4,6-dimethylphenyl)-2-methyl-4,5,6,7-tetrahydro-2H-pyrazolo[3,4-b]pyridin-3-yl]heptan-4-ol | 129–130 | 390 (390) |
| 5b | 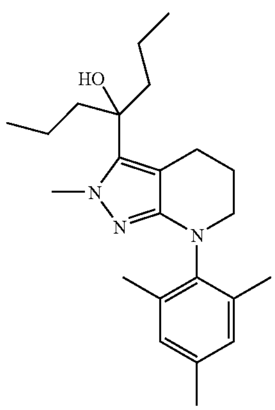 | 4-[2-Methyl-7-(2,4,6-trimethylphenyl)-4,5,6,7-tetrahydro-2H-pyrazolo[3,4-b]pyridin-3-yl]heptan-4-ol | 126–127.9 | 370 (370) |
| 5c | 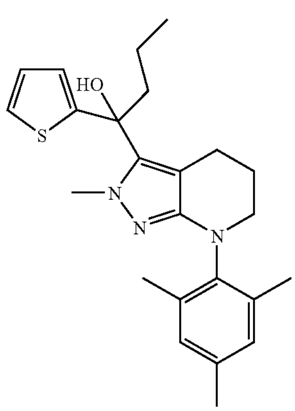 | 1-[8 2-Methyl-7-(2,4,6-trimethylphenyl)-4,5,6,7-tetrahydro-2H-pyrazolo[3,4-b]pyridin-3-yl]-1-thiophen-2-ylbutan-1-ol | 175.9–178.4 | 410 (410) |

TABLE 2-continued

Compounds prepared in Examples 5.

| Example | Structure | Name | mp (° C.) | MH+ observed (predicted) |
|---|---|---|---|---|
| 5d | 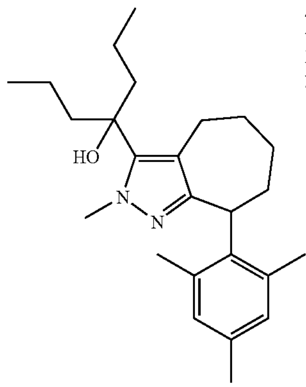 | 4-[2-Methyl-8-(2,4,6-trimethylphenyl)-2,4,5,6,7,8-hexahydro-1,2,8-triazaazulen-3-yl]heptan-4-ol | 87–91.1 | 384 (384) |
| 5e | 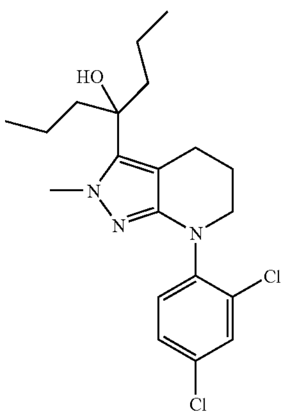 | 4-[7-(2,4-Dichlorophenyl)-2-methyl-4,5,6,7-tetrahydro-2H-pyrazolo[3,4-b]pyridin-3-yl]heptan-4-ol | 121.4–122.6 | 396 (396) |
| 5f | 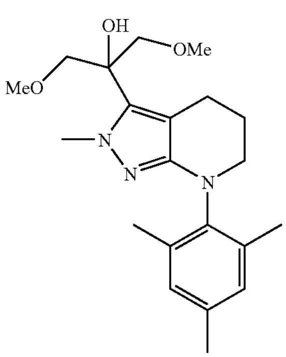 | 1,3-Dimethoxy-2-[2-methyl-7-(2,4,6-trimethylphenyl)-4,5,6,7-tetrahydro-2H-pyrazolo[3,4-b]pyridin-3-yl]propan-2-ol | 120.3–121.8 | 374 (374) |

TABLE 2-continued

Compounds prepared in Examples 5.

| Example | Structure | Name | mp (° C.) | MH+ observed (predicted) |
|---|---|---|---|---|
| 5g | 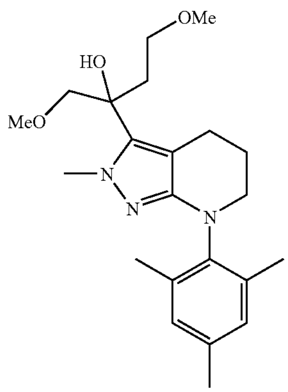 | 1,4-Dimethoxy-2-[2-methyl-7-(2,4,6-trimethylphenyl)-4,5,6,7-tetrahydro-2H-pyrazolo[3,4-b]pyridin-3-yl]butan-2-ol | 107.9–110.9 | 388 (388) |
| 5h | 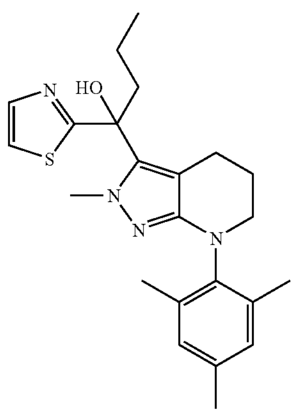 | 1-[2-Methyl-7-(2,4,6-trimethylphenyl)-4,5,6,7-tetrahydro-2H-pyrazolo[3,4-b]pyridin-3-yl]-1-thiazol-2-ylbutan-1-ol | 160.1–165.6 | 411 (411) |
| 5i | 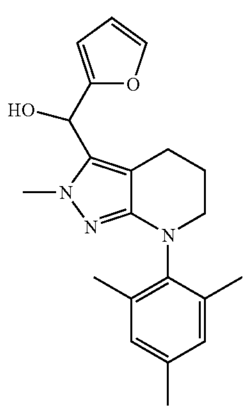 | Furan-2-yl[2-methyl-7-(2,4,6-trimethyl-phenyl)-4,5,6,7-tetrahydro-2H-pyrazolo[3,4-b]pyridin-3-yl]methanol | 163.1–174.4 | 352 (352) |

TABLE 2-continued

Compounds prepared in Examples 5.

| Example | Structure | Name | mp (° C.) | MH+ observed (predicted) |
|---|---|---|---|---|
| 5j | 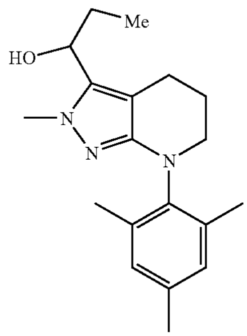 | 1-[2-Methyl-7-(2,4,6-trimethylphenyl)-4,5,6,7-tetrahydro-2H-pyrazolo[3,4-b]pyridin-3-yl]propan-1-ol | 179.4–180.9 | 314 (314) |
| 5k | 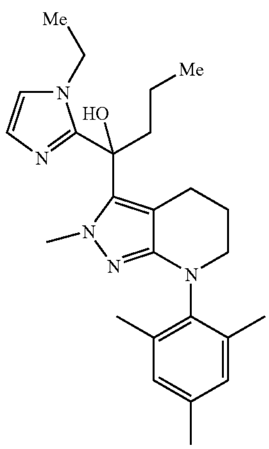 | 1-(1-Ethyl-1H-imidazol-2-yl)-1-[2-methyl-7-(2,4,6-trimethylphenyl)-4,5,6,7-tetrahydro-2H-pyrazolo[3,4-b]pyridin-3-yl]butan-1ol | 94.9–100.9 | 422 (422) |
| 5l | 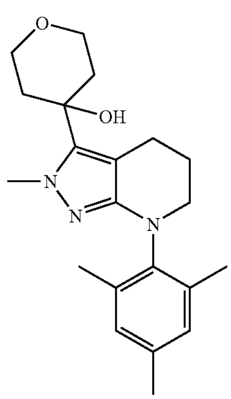 | 4-[2-Methyl-7-(2,4,6-trimethylphenyl)-4,5,6,7-tetrahydro-2H-pyrazolo[3,4-b]pyridin-3-yl]tetrahydropyran-4-ol | 193–195.1 | 356 (356) |
| 5m | 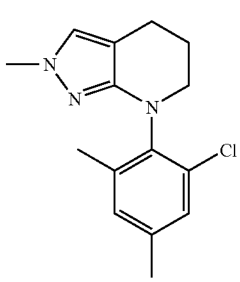 | 7-(2-Chloro-4,6-dimethylphenyl)-2-methyl-4,5,6,7-tetrahydro-2H-pyrazolo[3,4-b]pyridine | 97–98 | 276 (276) |

Example 6a 7-(2-Chloro-4,6-dimethylphenyl)-2-methyl-3-(1-propylbut-1-enyl)-4,5,6,7-tetrahydro-2H-pyrazolo[3,4-b]pyridine

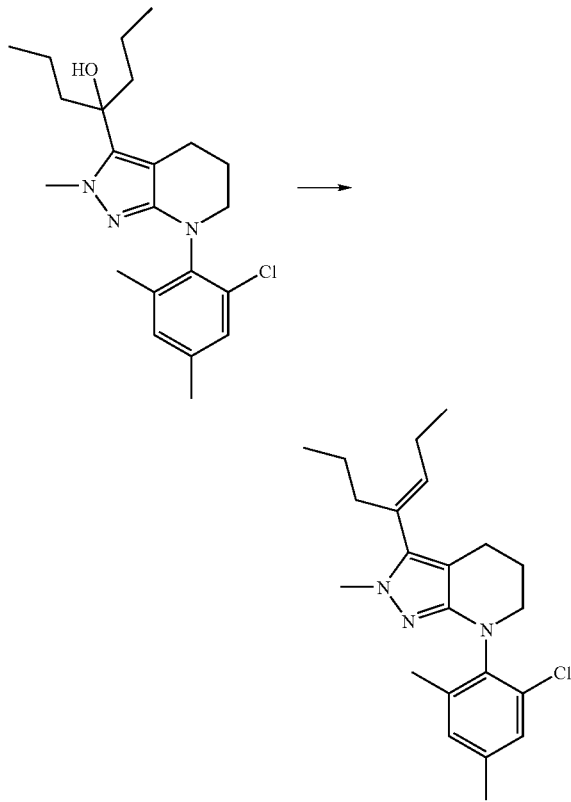

4-[7-(2-Chloro-4,6-dimethylphenyl)-2-methyl-4,5,6,7-tetrahydro-2H-pyrazolo[3,4-b]pyridin-3-yl]heptan-4-ol (594 mg) and p-toluenesulfonic acid monohydrate (74 mg) were combined in 13 mL toluene and the stirred mixture was heated to 110° C. for 11 h. The reaction mixture was then cooled to room temperature and partitioned between ethyl acetate and aqueous sodium bicarbonate. The aqueous phase was washed with additional ethyl acetate. The combined ethyl acetate was washed with brine, dried with magnesium sulfate, and concentrated. The residue was chromatographed on silica gel eluting with an acetone/hexane gradient to provide 461 mg of 7-(2-chloro-4,6-dimethylphenyl)-2-methyl-3-(1-propylbut-1-enyl)-4,5,6,7-tetrahydro-2H-pyrazolo[3,4-b]pyridine, which was recrystallized from hexane, mp 86.7–88.2° C.

Examples 6b–6f

Example 6b was prepared according to the procedure described in Example 6a, except that 4-[7-(2-chloro-4,6-dimethylphenyl)-2-methyl-4,5,6,7-tetrahydro-2H-pyrazolo[3,4-b]pyridin-3-yl]heptan-4-ol was replaced by the compound from Example 5b.

Example 6c was prepared according to the procedure described in Example 6a, except that 4-[7-(2-chloro-4,6-dimethylphenyl)-2-methyl-4,5,6,7-tetrahydro-2H-pyrazolo[3,4-b]pyridin-3-yl]heptan-4-ol was replaced by the compound from Example 5c.

Example 6d was prepared according to the procedure described in Example 6a, except that 4-[7-(2-chloro-4,6-dimethylphenyl)-2-methyl-4,5,6,7-tetrahydro-2H-pyrazolo[3,4-b]pyridin-3-yl]heptan-4-ol was replaced by the compound from Example 5d.

Example 6e was prepared according to the procedure described in Example 6a, except that 4-[7-(2-chloro-4,6-dimethylphenyl)-2-methyl-4,5,6,7-tetrahydro-2H-pyrazolo[3,4-b]pyridin-3-yl]heptan-4-ol was replaced by the compound from Example 5e.

Example 6f was prepared according to the procedure described in Example 6a, except that 4-[7-(2-chloro-4,6-dimethylphenyl)-2-methyl-4,5,6,7-tetrahydro-2H-pyrazolo[3,4-b]pyridin-3-yl]heptan-4-ol was replaced by the compound from Example 5h.

TABLE 3

Compounds prepared in Examples 6.

| Example | Structure | Name | mp (° C.) | MH+ observed (predicted) |
|---|---|---|---|---|
| 6a | 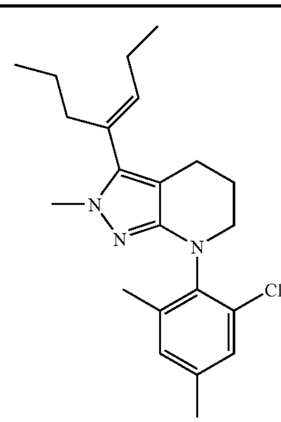 | 7-(2-Chloro-4,6-dimethylphenyl)-2-methyl-3-(1-propylbut-1-enyl)-4,5,6,7-tetrahydro-2H-pyrazolo[3,4-b]pyridine | 86.7–88.2 | 372 (372) |

TABLE 3-continued

Compounds prepared in Examples 6.

| Example | Structure | Name | mp (° C.) | MH+ observed (predicted) |
|---------|-----------|------|-----------|--------------------------|
| 6b | 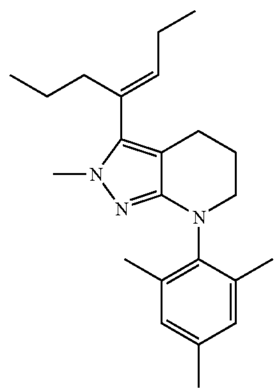 | 2-Methyl-3-(1-propylbut-1-enyl)-7-(2,4,6-trimethylphenyl)-4,5,6,7-tetrahydro-2H-pyrazolo[3,4-b]pyridine | 101.6–102.6 | 352 (352) |
| 6c | 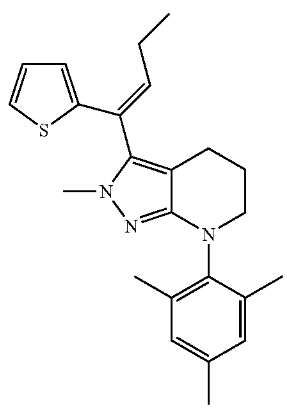 | 2-Methyl-3-(1-thiophen-2-ylbut-1-enyl)-7-(2,4,6-trimethylphenyl)-4,5,6,7-tetrahydro-2H-pyrazolo[3,4-b]pyridine | oil | 392 (392) |
| 6d | 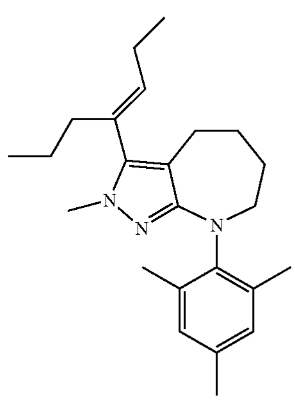 | 2-Methyl-3-(1-propylbut-1-enyl)-8-(2,4,6-trimethylphenyl)-2,4,5,6,7,8-hexahydro-1,2,8-triazaazulene | 101.9–103.9 | 366 (366) |

TABLE 3-continued

Compounds prepared in Examples 6.

| Example | Structure | Name | mp (° C.) | MH+ observed (predicted) |
|---|---|---|---|---|
| 6e | 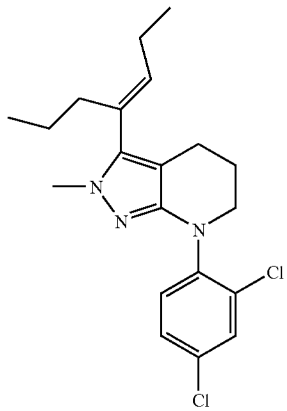 | 7-(2,4-Dichlorophenyl)-2-methyl-3-(1-propylbut-1-enyl)-4,5,6,7-tetrahydro-2H-pyrazolo[3,4-b]pyridine | oil | 378 (378) |
| 6f | 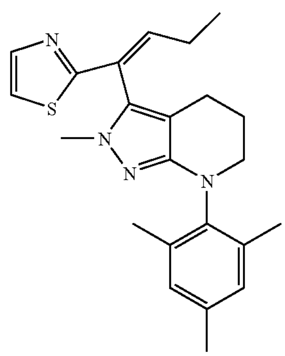 | 2-Methyl-3-(1-thiazol-2-ylbut-1-enyl)-7-(2,4,6-trimethyl-phenyl)-4,5,6,7-tetrahydro-2H-pyrazolo[3,4-b]pyridine | | 393 (393) |

Example 7a 7-(2-Chloro-4,6-dimethylphenyl)-2-methyl-3-(1-propylbutyl)-4,5,6,7-tetrahydro-2H-pyrazolo[3,4-b]pyridine

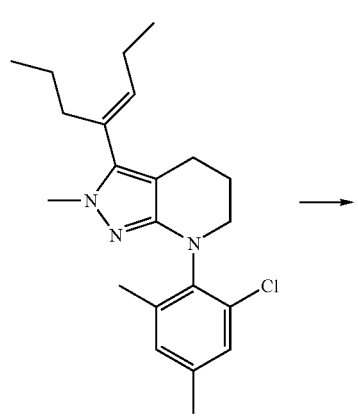

→

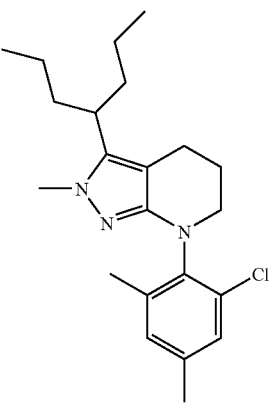

7-(2-Chloro-4,6-dimethylphenyl)-2-methyl-3-(1-propyl-but-1-enyl)-4,5,6,7-tetrahydro-2H-pyrazolo[3,4-b]pyridine (41.5 mg) was dissolved in acetic acid (1 mL) and 12 mg of 10% palladium on carbon was added. The mixture was stirred under hydrogen at one atmosphere for 12 h. The mixture was diluted with ethyl acetate and filtered through diatomaceous earth which was then washed with ethyl acetate. The ethyl acetate filtrate was washed with aqueous sodium bicarbonate, dried with magnesium sulfate, and concentrated. The residue was chromatographed on silica gel eluting with an acetone/hexane gradient to provide 10.2 mg of 7-(2-chloro-4,6-dimethylphenyl)-2-methyl-3-(1-propylbutyl)-4,5,6,7-tetrahydro-2H-pyrazolo[3,4-b]pyridine, as a crystalline film, ms m/z 374 (MH$^+$).

Examples 7b–7d

Example 7b was prepared according to the procedure described in Example 7a, except that 7-(2-chloro-4,6-dimethylphenyl)-2-methyl-3-(1-propylbut-1-enyl)- 4,5,6,7-tetrahydro-2Hpyrazolo[3,4-b]pyridine was replaced by the compound from Example 6b.

Example 7c was prepared according to the procedure described in Example 7a, except that 7-(2-chloro-4,6-dimethylphenyl)-2-methyl-3-(1-propylbut-1-enyl)-4,5,6,7-tetrahydro-2H-pyrazolo[3,4-b]pyridine was replaced by the compound from Example 6c.

Example 7d was prepared according to the procedure described in Example 7a, except that 7-(2-chloro-4,6-dimethylphenyl)-2-methyl-3-(1-propylbut-1-enyl)-4,5,6,7-tetrahydro-2H-pyrazolo[3,4-b]pyridine was replaced by the compound from Example 6d.

TABLE 4

Compounds prepared in Examples 7.

| Example | Structure | Name | mp (° C.) | MH+ observed (predicted) |
|---|---|---|---|---|
| 7a | 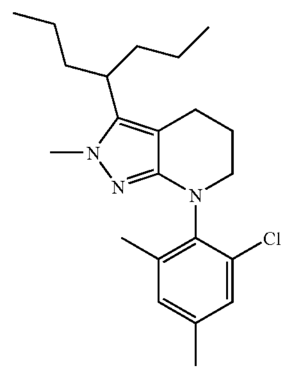 | 7-(2-Chloro-4,6-dimethylphenyl)-2-methyl-3-(1-propylbutyl)-4,5,6,7-tetrahydro-2H-pyrazolo[3,4-b]pyridine | | 374 (374) |
| 7b | 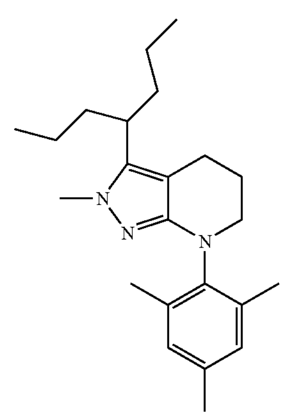 | 2-Methyl-3-(1-propylbutyl)-7-(2,4,6-trimethylphenyl)-4,5,6,7-tetrahydro-2H-pyrazolo[3,4-b]pyridine | 91.5–92 | 354 (354) |

TABLE 4-continued

Compounds prepared in Examples 7.

| Example | Structure | Name | mp (° C.) | MH+ observed (predicted) |
|---|---|---|---|---|
| 7c | 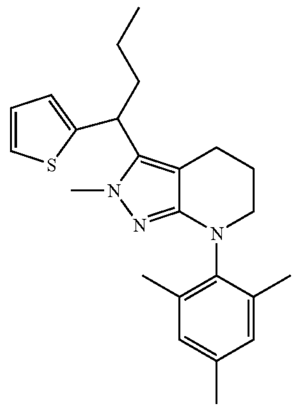 | 2-Methyl-3-(1-thiophen-2-ylbutyl)-7-(2,4,6-trimethylphenyl)-4,5,6,7-tetrahydro-2H-pyrazolo[3,4-b]pyridine | 87.6–90.3 | 394 (394) |
| 7d | 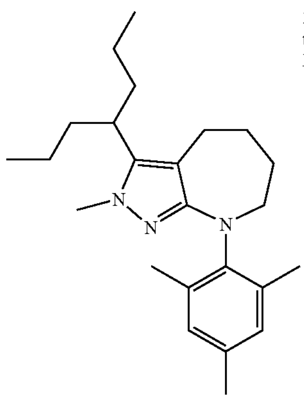 | 2-Methyl-3-(1-propylbutyl)-8-(2,4,6-trimethylphenyl)-2,4,5,6,7,8-hexahydro-1,2,8-triazaazulene | 96.0–98.1 | 368 (368) |

Example 8a 7-(2-Chloro-4,6-dimethylphenyl)-2-methyl-4,5,6,7-tetrahydro-2H-pyrazolo[3,4-b]pyridine-3-carboxylic Acid

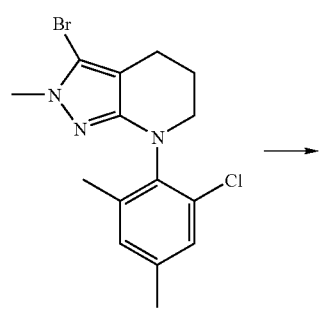

-continued

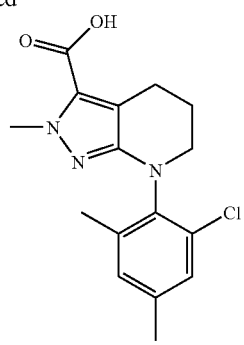

3-Bromo-7-(2-chloro-4,6-dimethylphenyl)-2-methyl-4,5,6,7-tetrahydro-2H-pyrazolo[3,4-b]pyridine (1.46 g) and a few crystals of 1, 10 phenanthroline were dissolved in 25 mL of dry tetrahydrofuran and chilled to −78° C. under an atmosphere of argon. Then a 2.0 M solution of n-butyllithium in cyclohexane was added dropwise until the dark color of the phenanthroline/organolithium complex persisted. Then an additional 2.05 mL of the n-butyllithium solution was added. After 10 minutes, carbon dioxide, generated from dry ice, was bubbled through the reaction mixture for 5 minutes. After the reaction mixture had been stirred at −78° C. for 5 minutes, the cooling bath was removed and the mixture was allowed to warm for 5 minutes before being quenched by the addition of water. The mixture was combined with ethyl acetate and water, acidified with dilute hydrochloric acid, and the phases separated. The ethyl acetate was dried with magnesium sulfate and concentrated. The residue was chromatographed on silica gel eluting with an acetone/hexane gradient to provide 1.11 g of 7-(2-chloro-4,6-dimethylphenyl)-2-methyl-4,5,6,7-tetrahydro-2H-pyrazolo[3,4-b]pyridine-3-carboxylic acid, mp 247.8–248.3° C.

Example 8b 7-(2,4,6-Trimethylphenyl)-2-methyl-4,5,6,7-tetrahydro-2H-pyrazolo[3,4-b]pyridine-3-carboxylic Acid Example 8b was prepared according to the procedure described in Example 8a, except that 3-bromo-7-(2-chloro-4,6-dimethylphenyl)-2-methyl-4,5,6,7-tetrahydro-2H-pyrazolo[3,4-b]pyridine was replaced by the compound from Example 3.

Example 8c

[7-(2-Chloro-4,6-dimethylphenyl)-2-methyl-4,5,6,7-tetrahydro-2H-pyrazolo[3,4-b]pyridin-3-yl]carbamic Acid Tert-butyl Ester

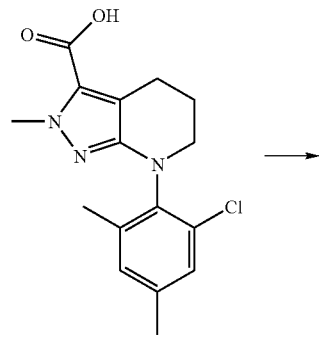

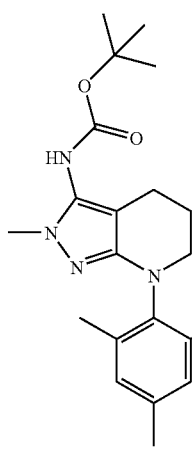

A 159 mg sample of 7-(2-chloro-4,6-dimethylphenyl)-2-methyl-4,5,6,7-tetrahydro-2H-pyrazolo[3,4-b]pyridine-3-carboxylic acid was combined with 2.5 mL of t-butanol and 140 μL of triethylamine was added. Then 129 μL of diphenylphosphoryl azide was added and the reaction mixture was heated to 85° C. for 2 h. After cooling to room temperature, the reaction mixture was dissolved in ethyl acetate and washed with 1M aqueous sodium bisulfate, aqueous sodium bicarbonate, water, and brine. The ethyl acetate solution was dried with magnesium sulfate and concentrated to give material which was chromatographed on silica gel eluting with an acetone/hexane gradient. Product containing fractions were concentrated to give a solid residue which was slurried in a small amount of boiling hexane. After the mixture cooled to room temperature, the solids were collected by filtration to provide 71 mg of [7-(2-chloro-4,6-dimethylphenyl)-2-methyl-4,5,6,7-tetrahydro-2H-pyrazolo[3,4-b]pyridin-3-yl]carbamic acid tert-butyl ester, mp 171.4–175.7° C.

Example 8d

Example 8d was prepared according to the procedure described in Example 8c, except that t-butanol was replaced by ethanol.

Example 9a

[7-(2-Chloro-4,6-dimethylphenyl)-2-methyl-4,5,6,7-tetrahydro-2H-pyrazolo[3,4-b]pyridin-3-yl]dipropylamine

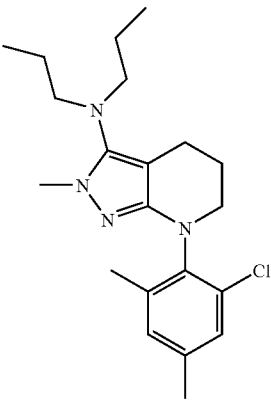

Step 1

7-(2-Chloro-4,6-dimethylhenyl)-2-methyl-4,5,6,7-tetrahydro-2H-pyrazolo[3,4-b]pyridin-3-ylamine

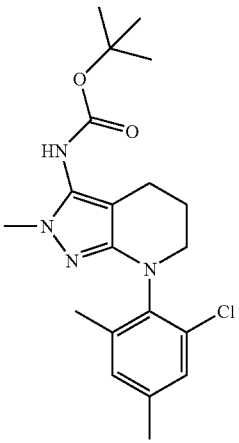

-continued

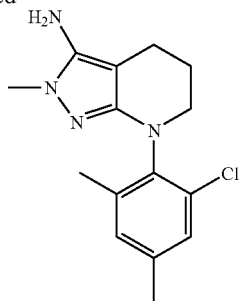

To a 0° C. solution of 287 mg of [7-(2-chloro-4,6-dimethylphenyl)-2-methyl-4,5,6,7-tetrahydro-2H-pyrazolo[3,4-b]pyridin-3-yl]carbamic acid tert-butyl ester (Example 8c) in 9 mL of dichloromethane, was added 3 mL of trifluoroacetic acid. After 15 min, the cooling bath was removed and the reaction mixture was allowed to stir and warm to room temperature during 3 h. The reaction mixture was then diluted with dichloromethane and washed with dilute aqueous sodium hydroxide. The aqueous phase was washed with additional dichloromethane, after which the combined organics were dried with magnesium sulfate and concentrated. The residue was chromatographed on silica gel eluting with a methanol/dichloromethane gradient to provide 182 mg of 7-(2-chloro-4,6-dimethylphenyl)-2-methyl-4,5,6,7-tetrahydro-2H-pyrazolo[3,4-b]pyridin-3-ylamine, mp 234–236° C.

Step 2

[7-(2-Chloro-4,6-dimethylphenyl)-2-methyl-4,5,6,7-tetrahydro-2H-pyrazolo[3,4-b]pyridin-3-yl]dipropylamine

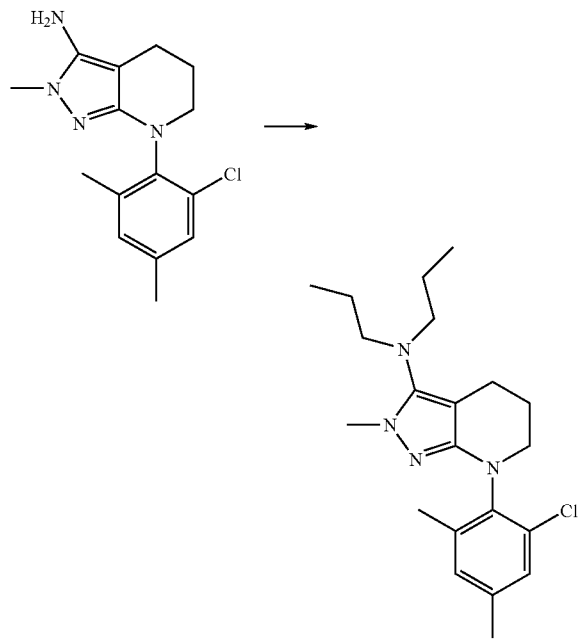

To a solution of 55 mg of 7-(2-chloro-4,6-dimethylphenyl)-2-methyl-4,5,6,7-tetrahydro-2H-pyrazolo[3,4-b]pyridin-3-ylamine in 3 mL of dichloroethane was added 29 μL of propionaldehyde followed a few minutes later by 124 mg of sodium triacetoxyborohydride. The reaction mixture was stirred at room temperature for 2 d, during which time an additional 30 μL of propionaldehyde and an additional 62 mg of sodium triacetoxyborohydride were added to drive the reaction to completion. The mixture was then diluted with dichloromethane and washed with dilute aqueous sodium hydroxide. The organics were dried over magnesium sulfate and concentrated. The residue was chromatographed on silica gel eluting with an acetone/hexane gradient to provide a solid which was recrystallized from hexane to give 17 mg of [7-(2-chloro-4,6-dimethylphenyl)-2-methyl-4,5,6,7-tetrahydro-2H-pyrazolo[3,4-b]pyridin-3-yl]dipropylamine, mp 90–91° C.

Example 9b

Example 9b was prepared according to the procedure described in Example 9a, except that step 2 was performed as follows:

Step 2

[7-(2-Chloro-4,6-dimethylphenyl)-2-methyl-4,5,6,7-tetrahydro-2H-pyrazolo[3,4-b]pyridin-3-yl](1-propylbutyl)amine

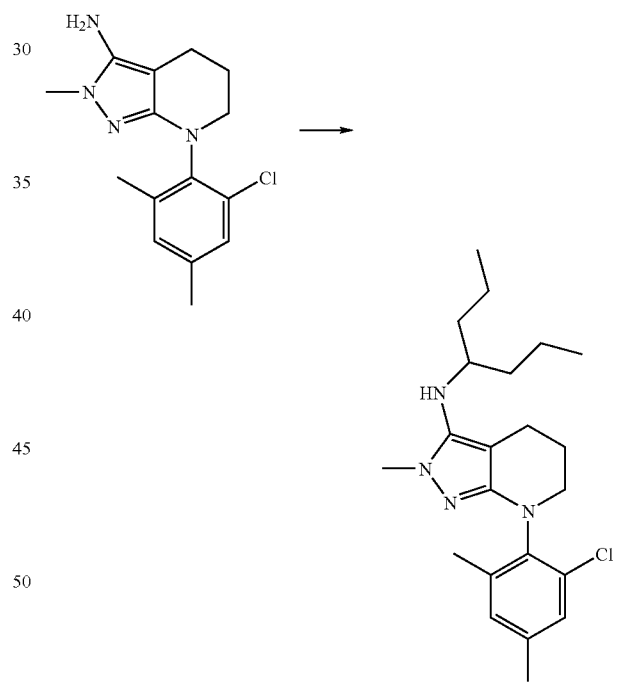

7-(2-Chloro-4,6-dimethylphenyl)-2-methyl-4,5,6,7-tetrahydro-2H-pyrazolo[3,4-b]pyridin-3-ylamine (45.7 mg) and 4-heptanone (24 μL) were dissolved and stirred in 3 mL of dichloroethane. After 15 min, 44.5 mg of sodium triacetoxyborohydride was added. The reaction mixture was stirred at 60° C. during the day and at room temperature over night during 3 d. During this period, an additional 109 μL of 4-heptanone and an additional 104 mg of sodium triacetoxyborohydride were added to drive the reaction to completion. The reaction mixture was then partitioned between ethyl acetate and water. The ethyl acetate was dried with magnesium sulfate and concentrated. The crude product was chromatographed on silica gel eluting with an acetone/hexane gradient to provide 11 mg of [7-(2-chloro-4,6-dimethylphenyl)-2-methyl-4,5,6,7-tetrahydro-2H-pyrazolo[3,4-b]pyridin-3-yl](1-propylbutyl)amine as a crystalline film, ms m/z 389 (MH⁺).

Example 9c

[7-(2-Chloro-4,6-dimethylphenyl)-2-methyl-4,5,6,7-tetrahydro-2H-pyrazolo[3,4-b]pyridin-3-yl]furan-2-ylmethylpropylamine

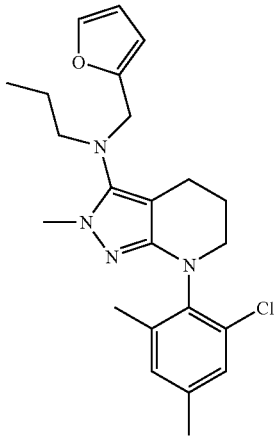

Step 1

N-[7-(2-Chloro-4,6-dimethylphenyl)-2-methyl-4,5,6,7-tetrahydro-2H-pyrazolo[3,4-b]pyridin-3-yl]propionamide

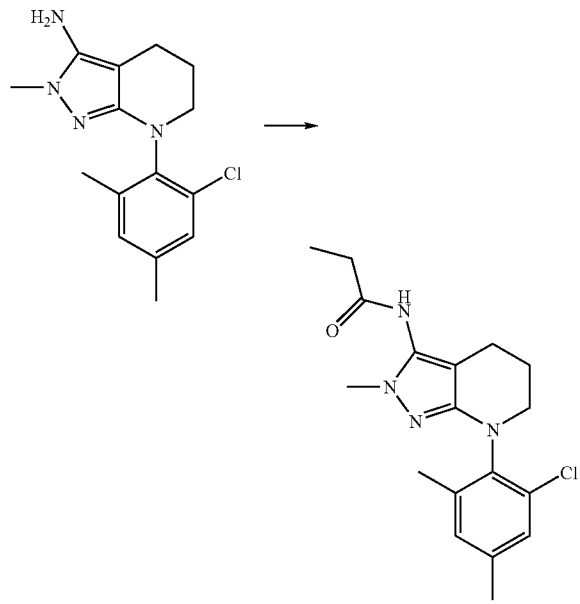

To a stirred solution of 7-(2-chloro-4,6-dimethylphenyl)-2-methyl-4,5,6,7-tetrahydro-2H-pyrazolo[3,4-b]pyridin-3-ylamine (0.51 g) and triethylamine (0.27 mL) in dichloromethane (40 mL) at 0° C. was added propionyl chloride (0.17 mL) in dichloromethane (10 mL) dropwise over 25 minutes. The resulting mixture was stirred for an additional 1 hour at 0° C., followed by 14 hours at room temperature. The reaction mixture was then stirred with an aqueous 5% citric acid solution (40 mL) for 10 minutes. The layers were separated, and the aqueous layer was further extracted with dichloromethane (50 mL). The combined organic extracts were dried over anhydrous sodium sulfate, then decanted from the desiccating agent and concentrated under reduced pressure. The resulting residue was purified by silica gel chromatography using a dichloromethane/methanol gradient to afford N-[7-(2-chloro-4,6-dimethylphenyl)-2-methyl-4,5,6,7-tetrahydro-2H-pyrazolo[3,4-b]pyridin-3-yl]propionamide (0.49 g) as an off white solid, ms m/z 347 (MH⁺).

Step 2

[7-(2-Chloro-4,6-dimethylphenyl)-2-methyl-4,5,6,7-tetrahydro-2H-pyrazolo[3,4-b]pyridin-3-yl]propylamine To a stirred, chilled (0° C.) solution of N-[7-(2-chloro-4,6-dimethylphenyl)-2-methyl-4,5,6,7-tetrahydro-2H-pyrazolo[3,4-b]pyridin-3-yl]propionamide (0.48 g) in tetrahydrofuran (9 mL), under nitrogen, was added borane-THF complex (4.1 mL of a 1.0 M tetrahydrofuran solution) in one portion. The resulting mixture was stirred for 1 hour at 0° C., then stirred for 48 hours at room temperature. The reaction mixture was then treated with 1:2 acetic acid/ethyl acetate (11 mL), mixed briefly, and allowed to stand at room temperature for 24 hours. The resulting mixture was added to a 3% aqueous sodium hydroxide solution (75 mL), and extracted with ethyl acetate (3×75 mL). The combined organic extracts were dried over anhydrous sodium sulfate, then decanted from the desiccating agent and concentrated under reduced pressure to provide, without further purification, [7-(2-chloro-4,6-dimethylphenyl)-2-methyl-4,5,6,7-tetrahydro-2H-pyrazolo[3,4-b]pyridin-3-yl]propylamine (0.45 g), as a pale yellow solid, ms m/z 333 (MH⁺).

Step 3

[7-(2-Chloro-4,6-dimethylphenyl)-2-methyl-4,5,6,7-tetrahydro-2H-pyrazolo[3,4-b]pyridin-3-yl]furan-2-ylmethylpropylamine

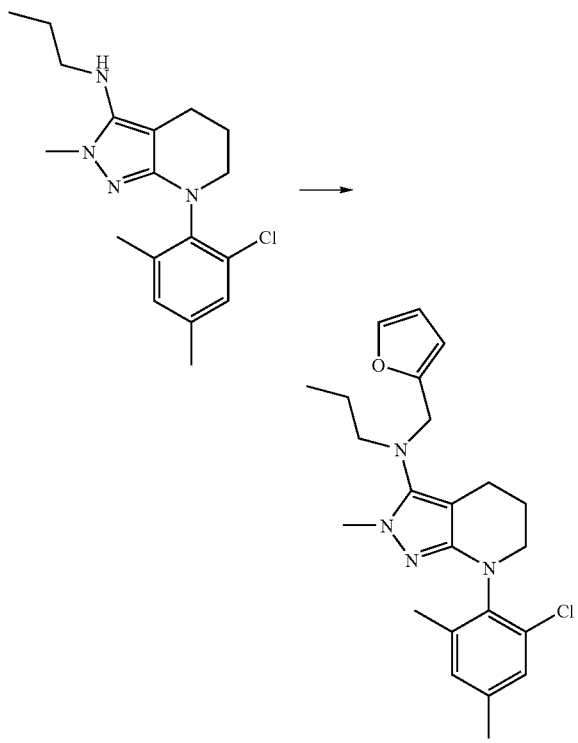

[7-(2-Chloro-4,6-dimethylphenyl)-2-methyl-4,5,6,7-tetrahydro-2H-pyrazolo[3,4-b]pyridin-3-yl]propylamine (17 mg) was treated with a solution of 2-furancarboxaldehyde (9 mg) in 1,2-dichloroethane (0.38 mL). To the resulting mixture was then added acetic acid (15 mg), followed by sodium triacetoxyborohydride (30 mg). At room temperature, the resulting mixture was agitated for 72 hours using a rotary shaker. The reaction mixture was then treated with saturated aqueous sodium bicarbonate (2 mL) and extracted with ethyl acetate (3×2 mL). The combined organic extracts were then concentrated under reduced pressure. The resulting orange-yellow residue was purified by preparative high-pressure liquid chromatography (HPLC) on reversed-phase (C18) silica gel (gradient, acetonitrile-0.1% trifluoroacetic acid=10:90 to 90:10) to afford [7-(2-chloro-4,6-dimethylphenyl)-2-methyl-4,5,6,7-tetrahydro-2H-pyrazolo[3,4-b]pyridin-3-yl]furan-2-ylmethylpropylamine, trifluoroacetate salt (5 mg) as a yellow solid, ms m/z 413 (MH+).

Examples 9d–9ai

Example 9d was prepared according to the procedure described in Example 9c, except that 2-furancarboxaldehyde was replaced by pyridine-2-carboxaldehyde in step 3.

Example 9e was prepared according to the procedure described in Example 9c, except that 2-furancarboxaldehyde was replaced by pyridine-4-carboxaldehyde in step 3.

Example 9f was prepared according to the procedure described in Example 9c, except that 2-furancarboxaldehyde was replaced by imidazole-2-carboxaldehyde in step 3.

Example 9g was prepared according to the procedure described in Example 9c, except that 2-furancarboxaldehyde was replaced by pyridine-3-carboxaldehyde in step 3.

Example 9h was prepared according to the procedure described in Example 9c, except that 2-furancarboxaldehyde was replaced by imidazole-4-carboxaldehyde in step 3.

Example 9i was prepared according to the procedure described in Example 9c, except that 2-furancarboxaldehyde was replaced by 3,4,5-trimethoxybenzaldehyde in step 3.

Example 9j was prepared according to the procedure described in Example 9c, except that 2-furancarboxaldehyde was replaced by 2,3,4-trimethoxybenzaldehyde in step 3.

Example 9k was prepared according to the procedure described in Example 9c, except that 2-furancarboxaldehyde was replaced by 1-methylimidazole-4-carboxaldehyde in step 3.

Example 9l was prepared according to the procedure described in Example 9c, except that 2-furancarboxaldehyde was replaced by 3-methylimidazole-4-carboxaldehyde in step 3.

Examples 9m–9ae and 9ai in Table 5 were prepared by reductive amination as described in step 3 of Example 9c with the appropriate secondary amines and aldehyde. The secondary amines were prepared by reduction of amides 10c and 10d (Table 6) as described in step 2 of Example 9c.

Example 9af (1-Methoxymethylpropyl)-[2-methyl-7-(2,4,6-trimethylphenyl)-4,5,6,7-tetrahydro-2H-pyrazolo[3,4-b]pyridin-3-yl]-amine

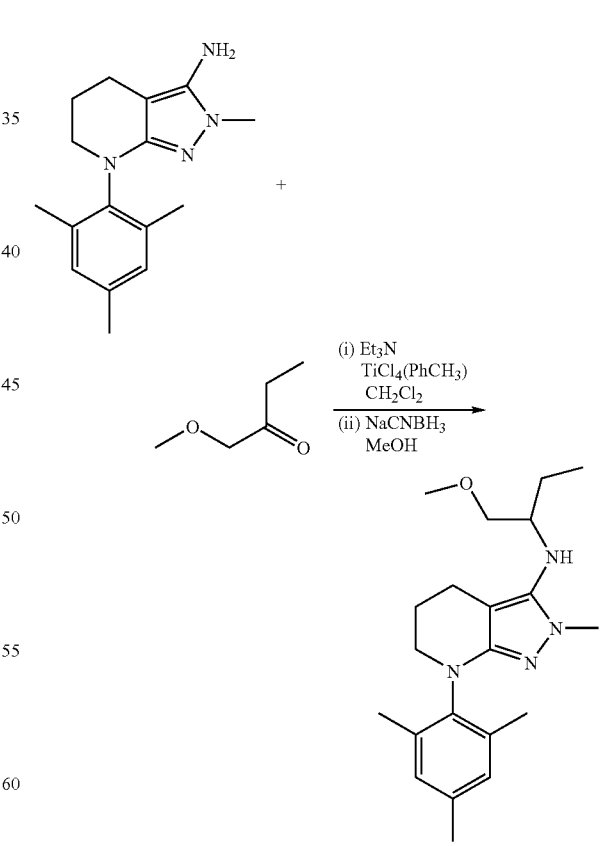

2-Methyl-7-(2,4,6-trimethyl-phenyl)-4,5,6,7-tetrahydro-2H-pyrazolo[3,4-b]pyridin-3-ylamine (101 mg, 0.373 mmol) was dissolved in CH$_2$Cl$_2$ (2 mL). Et$_3$N (0.25 mL, 1.79 mmol) and the 1-methoxy-butan-2-one (65 mg, 0.636 mmol) were added at room temperature. A solution of TiCl$_4$ in toluene (1 M; 0.35 mL, 0.35 mmol) was added dropwise via syringe. The mixture was then stirred at room temperature overnight. NaCNBH$_3$ (120 mg, 1.9 mmol) in methanol (1 mL) was added slowly. The stirring continued at room temperature for 0.5 h and the reaction was quenched by the addition of 2 N NaOH (2 mL). EtOAc was added and the layers were separated. The organic layer was washed with water, brine and dried over MgSO$_4$ The solvent was removed and the residue purified by chromatography on SiO$_2$, (gradient elution: 2% MeOH in CH$_2$Cl$_2$ containing 0.1% NH$_4$OH to 3% MeOH in CH$_2$Cl$_2$ containing 0.15% NH$_4$OH over 20 minutes) to yield 102 mg of product (0.286 mmol; 77%).

Examples 9ag, 9ah, 9aj and 9ak were prepared in analogous fashion using 3-pentanone, 1,3-dimethoxypropan-2-one, and 1,4-dimethoxypentan-2-one.

Example 9al was prepared using the appropriate methodology described hereinabove to prepare propyl 7-(2,4,6-trimethylphenyl)-2-methyl-4,5,6,7-tetrahydro-2H-pyrazolo[3,4-b]pyridin-3-ylamine which is reacted with phenylsulfonyl chloride utilizing Schotten-Bauman conditions.

TABLE 5

Compounds prepared in Examples 8–9.

| Example | Structure | Name | mp (° C.) | MH+ observed (predicted) |
|---|---|---|---|---|
| 8a | 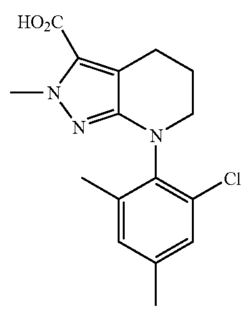 | 7-(2-Chloro-4,6-dimethylphenyl)-2-methyl-4,5,6,7-tetrahydro-2H-pyrazolo[3,4-b]pyridine-3-carboxylic acid | 247.8–248.3 | 320 (320) |
| 8b | 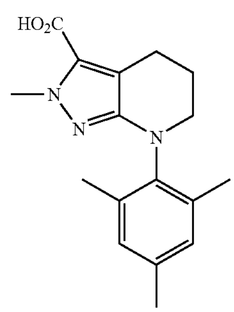 | 7-(2,4,6-Trimethylphenyl)-2-methyl-4,5,6,7-tetrahydro-2H-pyrazolo[3,4-b]pyridine-3-carboxylic acid | 228.6–233.9 | 300 (300) |
| 8c | 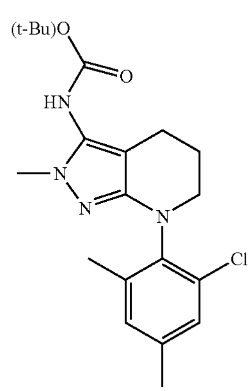 | [7-(2-Chloro-4,6-dimethylphenyl)-2-methyl-4,5,6,7-tetrahydro-2H-pyrazolo[3,4-b]pyridin-3-yl]carbamic acid tert-butyl ester | 171.4–175.7 | 391 (391) |

TABLE 5-continued

Compounds prepared in Examples 8–9.

| Example | Structure | Name | mp (° C.) | MH+ observed (predicted) |
|---|---|---|---|---|
| 8d | 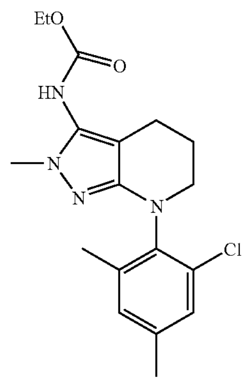 | [7-(2-Chloro-4,6-dimethylphenyl)-2-methyl-4,5,6,7-tetrahydro-2H-pyrazolo[3,4-b]pyridin-3-yl]carbamic acid ethyl ester | 204.0–207.8 | 363 (363) |
| 9a | 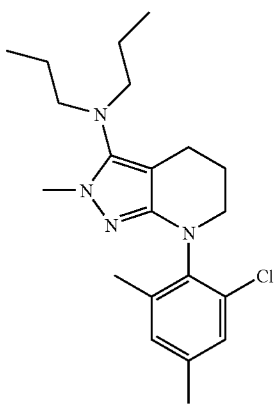 | [7-(2-Chloro-4,6-dimethylphenyl)-2-methyl-4,5,6,7-tetrahydro-2H-pyrazolo[3,4-b]pyridin-3-yl]dipropylamine | 90–91 | 375 (375) |
| 9b | 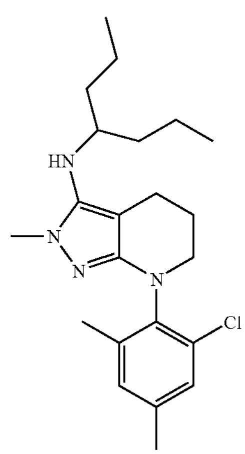 | [7-(2-Chloro-4,6-dimethylphenyl)-2-methyl-4,5,6,7-tetrahydro-2H-pyrazolo[3,4-b]pyridin-3-yl](1-propylbutyl)amine | | 389 (389) |

TABLE 5-continued

Compounds prepared in Examples 8–9.

| Example | Structure | Name | mp (° C.) | MH+ observed (predicted) |
|---|---|---|---|---|
| 9c | 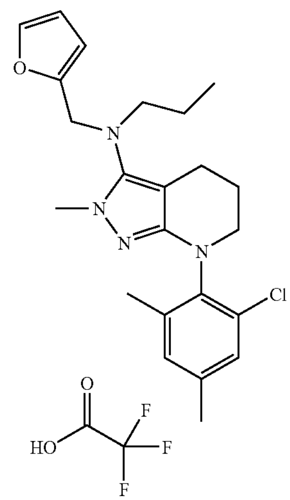 | [7-(2-Chloro-4,6-dimethyl-phenyl)-2-methyl-4,5,6,7-tetrahydro-2H-pyrazolo[3,4-b]pyridin-3-yl]-furan-2-ylmethyl-propyl-amine trifluoroacetic acid salt | | 413 (413) |
| 9d | 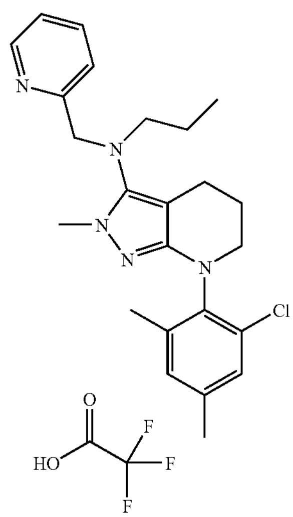 | [7-(2-Chloro-4,6-dimethyl-phenyl)-2-methyl-4,5,6,7-tetrahydro-2H-pyrazolo[3,4-b]pyridin-3-yl]-propyl-pyridin-2-ylmethyl-amine trifluoroacetic acid salt | | 424 (424) |

TABLE 5-continued

Compounds prepared in Examples 8–9.

| Example | Structure | Name | mp (° C.) | MH+ observed (predicted) |
|---|---|---|---|---|
| 9e | 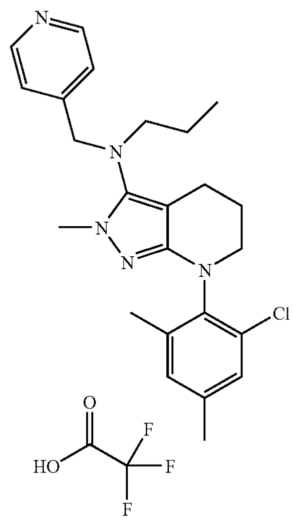 | [7-(2-Chloro-4,6-dimethyl-phenyl)-2-methyl-4,5,6,7-tetrahydro-2H-pyrazolo[3,4-b]pyridin-3-yl]-propyl-pyridin-4-ylmethyl-amine trifluoroacetic acid salt | | 424 (424) |
| 9f | 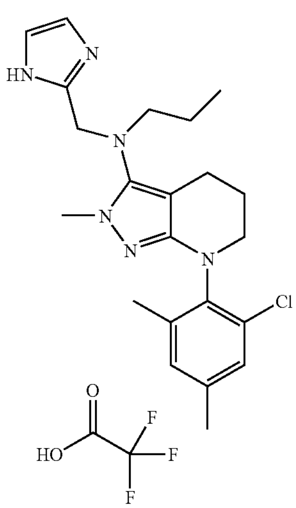 | [7-(2-Chloro-4,6-dimethyl-phenyl)-2-methyl-4,5,6,7-tetrahydro-2H-pyrazolo[3,4-b]pyridin-3-yl]-(1H-imidazol-2-ylmethyl)-propyl-amine trifluoroacetic acid salt | | 413 (413) |

TABLE 5-continued
Compounds prepared in Examples 8–9.
| Example | Structure | Name | mp (° C.) | MH+ observed (predicted) |
|---|---|---|---|---|
| 9g | 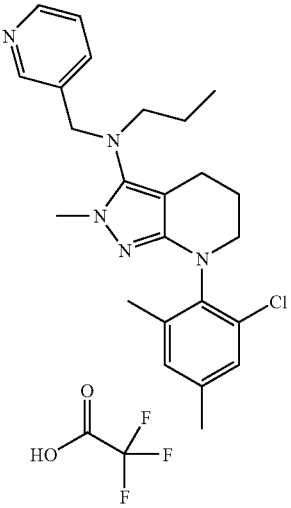 | [7-(2-Chloro-4,6-dimethyl-phenyl)-2-methyl-4,5,6,7-tetrahydro-2H-pyrazolo[3,4-b]pyridin-3-yl]-propyl-pyridin-3-ylmethyl-amine trifluoroacetic acid salt | | 424 (424) |
| 9h | 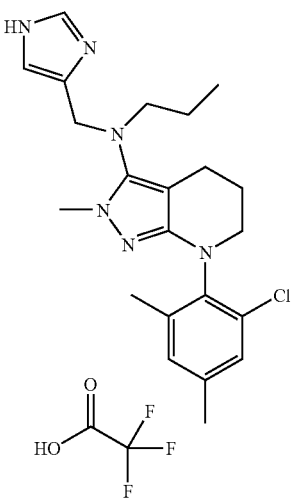 | [7-(2-Chloro-4,6-dimethyl-phenyl)-2-methyl-4,5,6,7-tetrahydro-2H-pyrazolo[3,4-b]pyridin-3-yl]-(1H-imidazol-4-ylmethyl)-propyl-amine trifluoroacetic acid salt | | 413 (413) |

TABLE 5-continued

Compounds prepared in Examples 8–9.

| Example | Structure | Name | mp (° C.) | MH+ observed (predicted) |
|---|---|---|---|---|
| 9i | 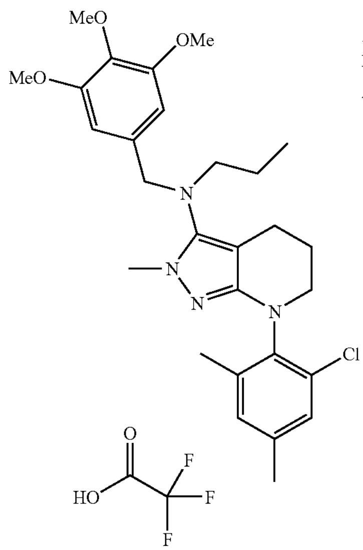 | [7-(2-Chloro-4,6-dimethyl-phenyl)-2-methyl-4,5,6,7-tetrahydro-2H-pyrazolo[3,4-b]pyridin-3-yl]-propyl-(3,4,5-trimethoxy-benzyl)-amine trifluoroacetic acid salt | | 513 (513) |
| 9j | 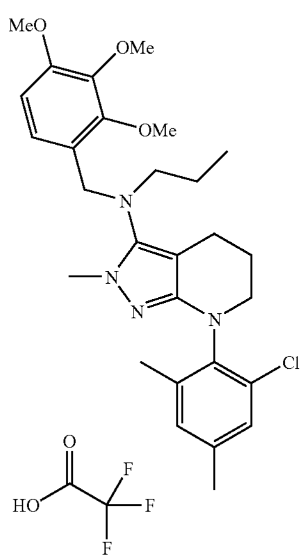 | [7-(2-Chloro-4,6-dimethyl-phenyl)-2-methyl-4,5,6,7-tetrahydro-2H-pyrazolo[3,4-b]pyridin-3-yl]-propyl-(2,3,4-trimethoxy-benzyl)-amine trifluoroacetic acid salt | | 513 (513) |

TABLE 5-continued

Compounds prepared in Examples 8–9.

| Example | Structure | Name | mp (° C.) | MH+ observed (predicted) |
|---|---|---|---|---|
| 9k | 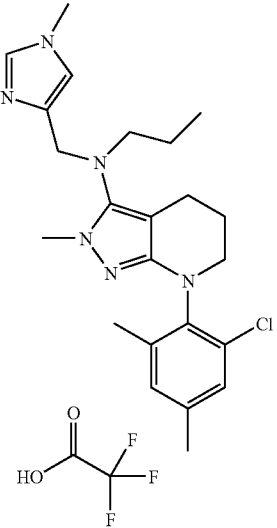 | [7-(2-Chloro-4,6-dimethyl-phenyl)-2-methyl-4,5,6,7-tetrahydro-2H-pyrazolo[3,4-b]pyridin-3-yl-(1-methyl-1H-imidazol-4-ylmethyl)-propyl-amine trifluoroacetic acid salt | | 427 (427) |
| 9l | 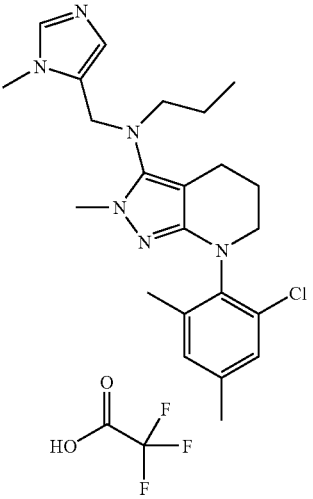 | [7-(2-Chloro-4,6-dimethyl-phenyl)-2-methyl-4,5,6,7-tetrahydro-2H-pyrazolo[3,4-b]pyridin-3-yl]-(3-methyl-3H-imidazol-4-ylmethyl)-propyl-amine trifluoroacetic acid salt | | 427 (427) |

TABLE 5-continued

Compounds prepared in Examples 8–9.

| Example | Structure | Name | mp (° C.) | MH+ observed (predicted) |
|---------|-----------|------|-----------|--------------------------|
| 9m | 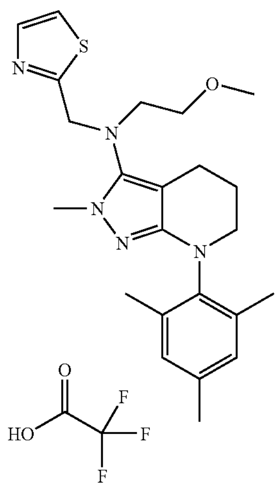 | (2-Methoxy-ethyl)-[2-methyl-7-(2,4,6-trimethylphenyl)-4,5,6,7-tetrahydro-2H-pyrazolo[3,4-b]pyridin-3-yl]thiazol-2-ylmethylamine, trifluoroacetic acid salt | | 426 (426) |
| 9n | 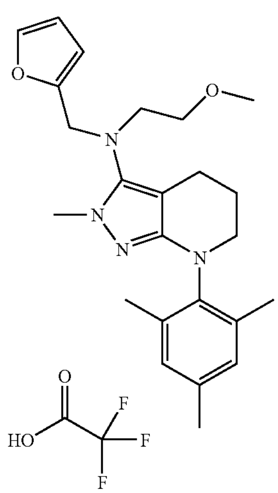 | Furan-2-ylmethyl-(2-methoxy-ethyl)-[2-methyl-7-(2,4,6-trimethyl-phenyl)-4,5,6,7-tetrahydro-2H-pyrazolo[3,4-b]pyridin-3-yl]amine, trifluoroacetic acid salt | | 409 (409) |

TABLE 5-continued

Compounds prepared in Examples 8–9.

| Example | Structure | Name | mp (° C.) | MH+ observed (predicted) |
|---|---|---|---|---|
| 9o | 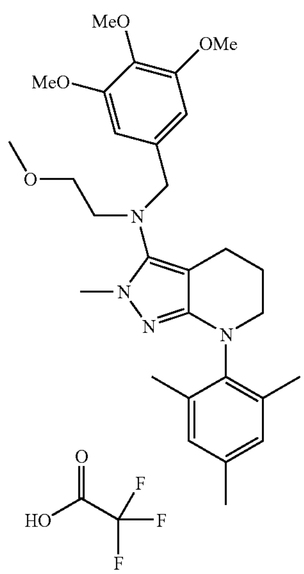 | (2-Methoxyethyl)-[2-methyl-7-(2,4,6-trimethylphenyl)-4,5,6,7-tetrahydro-2H-pyrazolo[3,4-b]pyridin-3-yl]-(3,4,5-trimethoxy-benzyl)amine, trifluoroacetic acid salt | | 509 (509) |
| 9p | 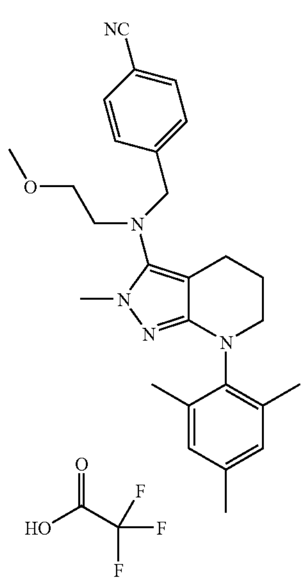 | 4({(2-Methoxyethyl)-[2-methyl-7-(2,4,6-trimethylphenyl)-4,5,6,7-tetrahydro-2H-pyrazolo[3,4-b]pyridin-3-yl]amino}methyl)benzonitrile, trifluoroacetic acid salt | | 444 (444) |

TABLE 5-continued
Compounds prepared in Examples 8–9.
| Example | Structure | Name | mp (° C.) | MH+ observed (predicted) |
|---|---|---|---|---|
| 9q | 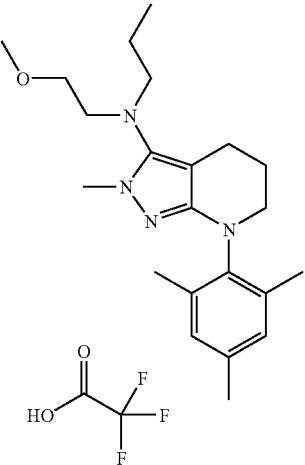 | (2-Methoxyethyl)-[2-methyl-7-(2,4,6-trimethylphenyl)-4,5,6,7-tetrahydro-2H-pyrazolo[3,4-b]pyridin-3-yl]propylamine, trifluoroacetic acid salt | | 371 (371) |
| 9r | 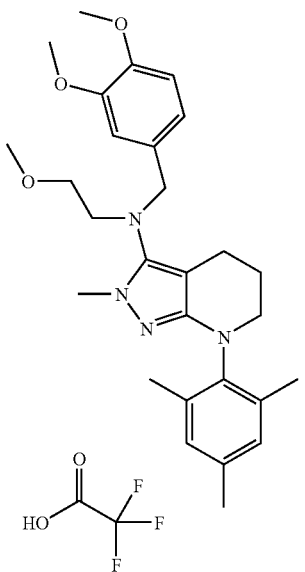 | (3,4-Dimethoxybenzyl)-(2-methoxyethyl)-[2-methyl-7-(2,4,6-trimethyl-phenyl)-4,5,6,7-tetrahydro-2H-pyrazolo[3,4-b]pyridin-3-yl]-amine, trifluoroacetic acid salt | | 479 (479) |

TABLE 5-continued

Compounds prepared in Examples 8–9.

| Example | Structure | Name | mp (° C.) | MH+ observed (predicted) |
|---|---|---|---|---|
| 9s | 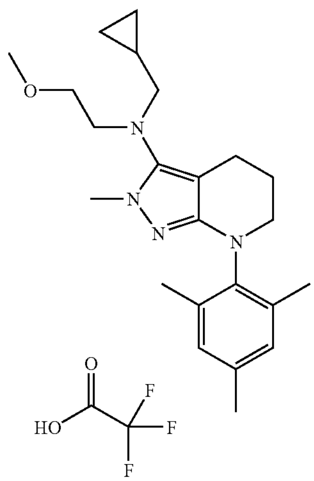 | Cyclopropylmethyl-(2-methoxyethyl)-[2-methyl-7-(2,4,6-trimethylphenyl)-4,5,6,7-tetrahydro-2H-pyrazolo[3,4-b]pyridin-3-yl]-amine | oil | 383 (383) |
| 9t | 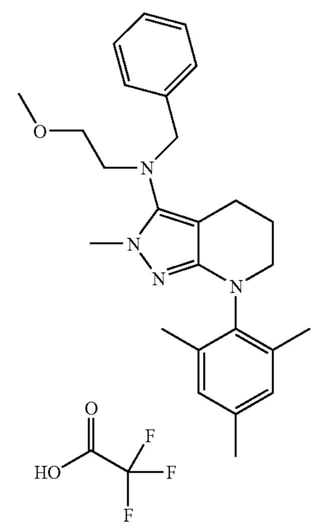 | Benzyl-(2-methoxyethyl)-[2-methyl-7-(2,4,6-trimethylphenyl)-4,5,6,7-tetrahydro-2H-pyrazolo[3,4-b]pyridin-3-yl]-amine, trifluoroacetic acid salt | | 419 (419) |
| 9u | 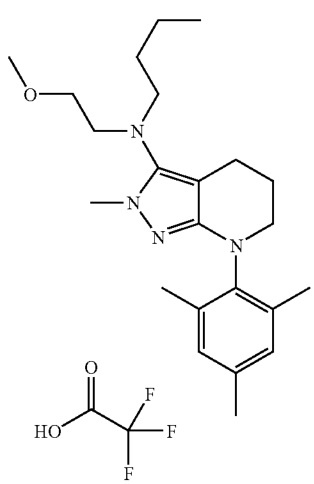 | Butyl-(2-methoxyethyl)-[2-methyl-7-(2,4,6-trimethylphenyl)-4,5,6,7-tetrahydro-2H-pyrazolo[3,4-b]pyridin-3-yl]-amine, trifluoroacetic acid salt | | 385 (385) |

TABLE 5-continued

Compounds prepared in Examples 8–9.

| Example | Structure | Name | mp (° C.) | MH+ observed (predicted) |
|---|---|---|---|---|
| 9v | 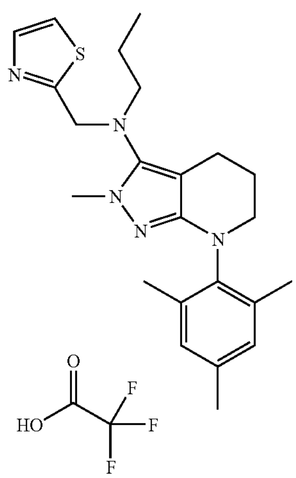 | [2-Methyl-7-(2,4,6-trimethylphenyl)-4,5,6,7-tetrahydro-2H-pyrazolo[3,4-b]pyridin-3-yl]-propylthiazol-2-ylmethylamine, trifluoroacetic acid salt | | 410 (410) |
| 9w | 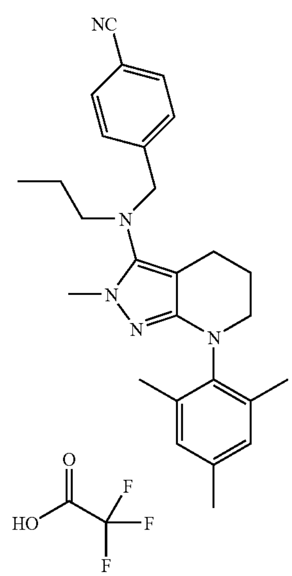 | 4-({[2-Methyl-7-(2,4,6-trimethyl-phenyl)-4,5,6,7-tetrahydro-2H-pyrazolo[3,4-b]pyridin-3-yl]-propylamino}-methyl)-benzonitrile, trifluoroacetic acid salt | | 428 (428) |

TABLE 5-continued
Compounds prepared in Examples 8–9.
| Example | Structure | Name | mp (° C.) | MH+ observed (predicted) |
|---|---|---|---|---|
| 9x | 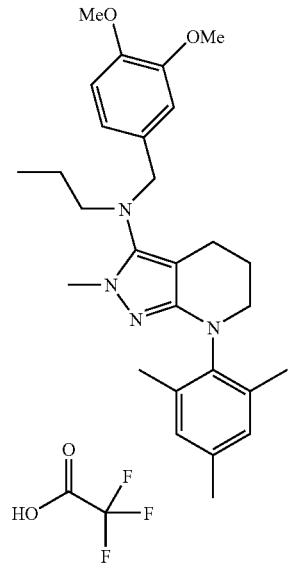 | (3,4-Dimethoxybenzyl)-[2-methyl-7-(2,4,6-trimethylphenyl)-4,5,6,7-tetrahydro-2H-pyrazolo[3,4-b]pyridin-3-yl]-propylamine, trifluoroacetic acid salt | | 463 (463) |
| 9y | 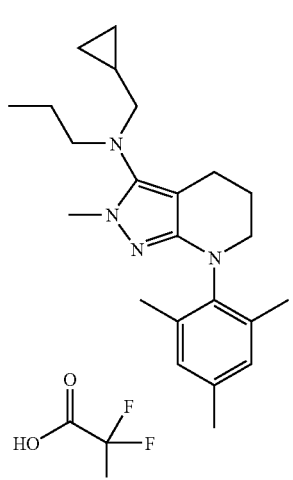 | Cyclopropylmethyl-[2-methyl-7-(2,4,6-trimethylphenyl)-4,5,6,7-tetrahydro-2H-pyrazolo[3,4-b]pyridin-3-yl]-propylamine, trifluoroacetic acid salt | | 367 (367) |

TABLE 5-continued
Compounds prepared in Examples 8–9.
| Example | Structure | Name | mp (° C.) | MH+ observed (predicted) |
|---|---|---|---|---|
| 9z | 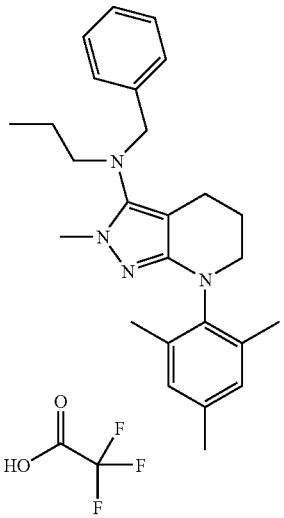 | Benzyl-[2-methyl-7-(2,4,6-trimethylphenyl)-4,5,6,7-tetrahydro-2H-pyrazolo[3,4-b]pyridin-3-yl]-proprylamine, trifluoroacetic acid salt | | 403 (403) |
| 9aa | 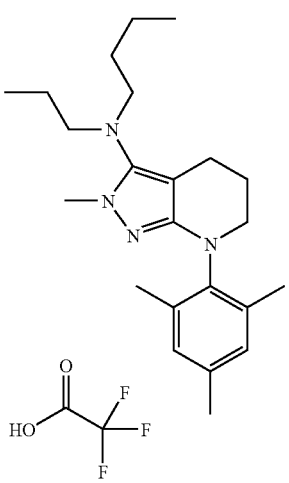 | Butyl-[2-methyl-7-(2,4,6-trimethylphenyl)-4,5,6,7-tetrahydro-2H-pyrazolo[3,4-b]pyridin-3-yl]-propylamine, trifluoroacetic acid salt | | 369 (369) |

TABLE 5-continued

Compounds prepared in Examples 8–9.

| Example | Structure | Name | mp (° C.) | MH+ observed (predicted) |
|---------|-----------|------|-----------|--------------------------|
| 9ab | 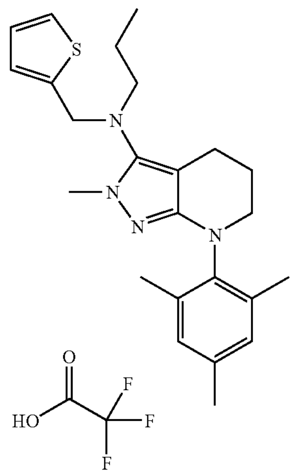 | [2-Methyl-7-(2,4,6-trimethylphenyl)-4,5,6,7-tetrahydro-2H-pyrazolo[3,4-b]pyridin-3-yl]-propylthiophen-2-ylmethylamine, trifluoroacetic acid salt | | 409 (409) |
| 9ac | 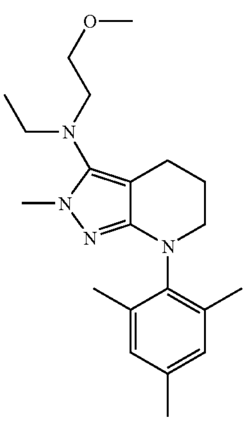 | Ethyl-(2-methoxyethyl)-[2-methyl-tetrahydro-2H-pyrazolo[3,4-b]pyridin-3-yl]-amine | oil | 357 (357) |
| 9ad | 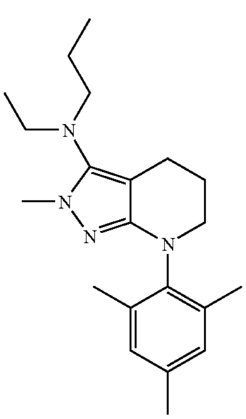 | Ethyl-[2-methyl-7-(2,4,6-trimethylphenyl)-4,5,6,7-tetrahydro-2H-pyrazolo[3,4-b]pyridin-3-yl]-propylamine | oil | 341 (341) |

TABLE 5-continued

Compounds prepared in Examples 8–9.

| Example | Structure | Name | mp (° C.) | MH+ observed (predicted) |
|---|---|---|---|---|
| 9ae | 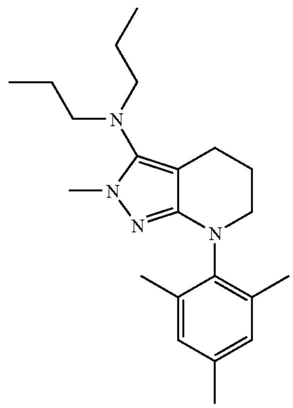 | [2-Methyl-7-(2,4,6-trimethylphenyl)-4,5,6,7-tetrahydro-2H-pyrazolo[3,4-b]pyridin-3-yl]-dipropylamine | 88.9–91.5 | 355 (355) |
| 9af | 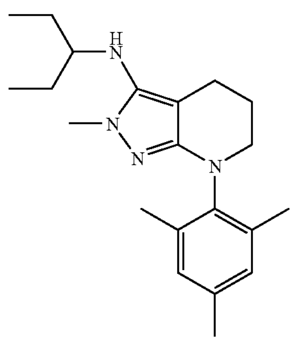 | (1-Ethylpropyl)-[2-methyl-7-(2,4,6-trimethyl-phenyl)-4,5,6,7-tetrahydro-2H-pyrazolo[3,4-b]pyridin-3-yl]-amine | 99.3–104.9 | 341 (341) |
| 9ag | 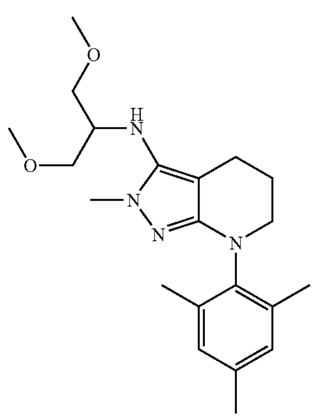 | (2-Methoxy-1-methoxymethylethyl)-[2-methyl-7-(2,4,6-trimethyphenyl)-4,5,6,7-tetrahydro-2H-pyrazolo[3,4-b]pyridin-3-yl]-amine | oil | 373 (373) |

TABLE 5-continued

Compounds prepared in Examples 8–9.

| Example | Structure | Name | mp (° C.) | MH+ observed (predicted) |
|---|---|---|---|---|
| 9ah | 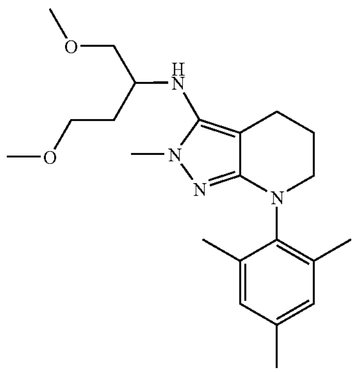 | (3-Methoxy-1-methoxymethylpropyl)-[2-methyl-7-(2,4,6-trimethyphenyl)-4,5,6,7-tetrahydro-2H-pyrazolo[3,4-b]pyridin-3-yl]-amine | oil | 387 (387) |
| 9ai | 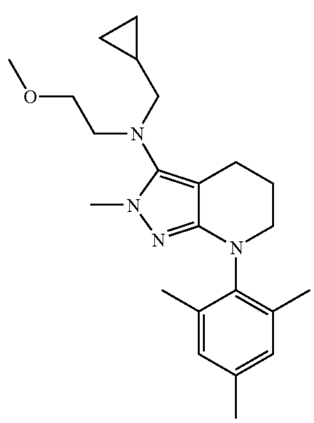 | Cyclopropylmethyl-(2-methoxyethyl)-[2-methyl-7-(2,4,6-trimethylphenyl)-4,5,6,7-tetrahydro-2H-pyrazolo[3,4-b]pyridin-3-yl]-amine | oil | 383 (383) |
| 9aj | 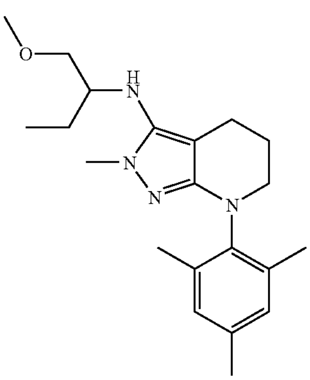 | (1-Methoxymethylpropyl)-[2-methyl-7-(2,4,6-trimethylphenyl)-4,5,6,7-tetrahydro-2H-pyrazolo[3,4-b]pyridin-3-yl]-amine | 96.5–102.5 | 357 (357) |

TABLE 5-continued

Compounds prepared in Examples 8–9.

| Example | Structure | Name | mp (° C.) | MH+ observed (predicted) |
|---|---|---|---|---|
| 9ak | 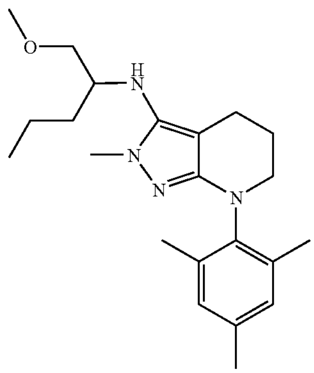 | (1-Methoxymethylbutyl)-[2-methyl-7-(2,4,6-trimethylphenyl)-4,5,6,7-tetrahydro-2H-pyrazolo[3,4-b]pyridin-3-yl]-amine | 100.1–104.4 | 371 (371) |
| 9al | 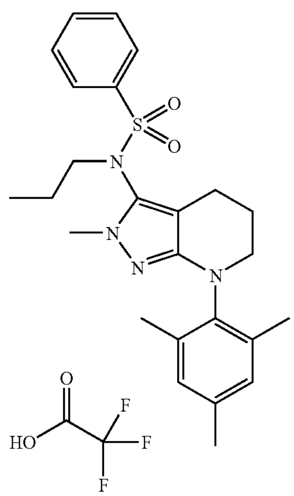 | N-[2-Methyl-7-(2,4,6-trimethylphenyl)-4,5,6,7-tetrahydro-2H-pyrazolo[3,4-b]pyridin-3-yl]-N-propylbenzenesulfonamide, trifluoroacetic acid salt | | 453 (453) |

Example 10a 7-(2-Chloro-4,6-dimethylphenyl)-2-methyl-4,5,6,7-tetrahydro-2H-pyrazolo[3,4-b]pyridine-3-carboxylic Acid Cyclopropylmethylpropylamide

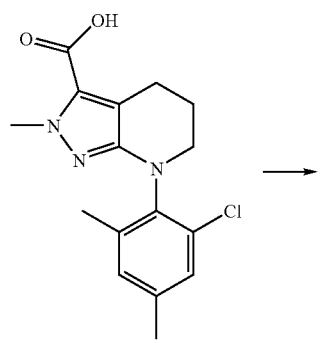

→

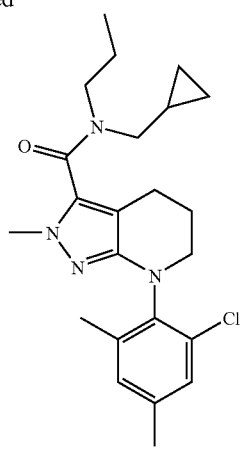

7-(2-Chloro-4,6-dimethylphenyl)-2-methyl-4,5,6,7-tetrahydro-2H-pyrazolo[3,4-b]pyridine-3-carboxylic acid (107.0 mg), 1-hydroxybenzotriazole hydrate (50.3 mg), 1-[3-(dimethylamino)propyl]-3-ethylcarbodiimide hydrochloride (72.5 mg), triethylamine (93 μL), and N-propylcyclopropanemethylamine (49 μL) were combined in 4 mL of dichloromethane and stirred at room temperature over night. The reaction mixture was then partitioned between ethyl acetate and 1M hydrochloric acid. The ethyl acetate solution was washed with aqueous sodium bicarbonate, dried with magnesium sulfate, and concentrated. The crude product was chromatographed on silica gel eluting with an acetone/hexane gradient giving a solid. Recrystallization from hexane provided 75.6 mg of 7-(2-chloro-4,6-dimethylphenyl)-2-methyl-4,5,6,7-tetrahydro-2H-pyrazolo[3,4-b]pyridine-3-carboxylic acid cyclopropylmethylpropylamide, mp 120.6–122.0° C.

Example 10b (3,4-Dihydro-1H-isoquinolyl-2-yl)[2-methyl-7-(2,4,6-trimethylphenyl)-4,5,6,7-tetrahydro-2H-pyrazolo[3,4-b]pyridin-3-yl]methanone

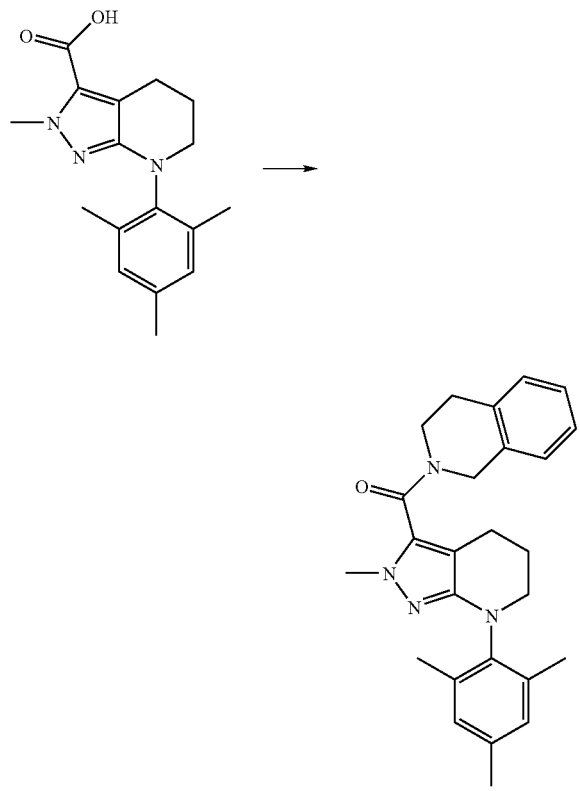

A suspension of 125 mg of 2-methyl-7-(2,4,6-trimethylphenyl)-4,5,6,7-tetrahydro-2H-pyrazolo[3,4-b]pyridine-3-carboxylic acid in 5 mL of dichloromethane was treated with 116 μL of triethylamine, 56 mg of 1-hydroxybenzotriazole hydrate, 88 mg of 1-[3-(dimethylamino)propyl]-3-ethylcarbodiimide hydrochloride, and 52 μL of 1,2,3,4-tetrahydroisoquinoline and stirred under an atmosphere of nitrogen at room temperature for 20 h. The mixture was diluted with 50 mL of ethyl acetate, washed with 30 mL of 0.5M HCl, washed with 30 mL of saturated sodium bicarbonate solution, dried over magnesium sulfate, and evaporated to dryness yielding 149 mg of (3,4-dihydro-1H-isoquinolin-2-yl) [2-methyl-7-(2,4,6-trimethylphenyl)-4,5,6,7-tetrahydro-2H-pyrazolo[3,4-b]pyridin-3-yl]methanone, mp 80.3–87.7° C.

Example 10c was prepared by acylation of 2-methyl-7-(2,4,6-trimethylphenyl)-4,5,6,7-tetrahydro-2H-pyrazolo[3,4-b]pyridin-3-ylamine (prepared from example 8b using procedures described for examples 8c and 9a; step 1) with propionyl chloride.

Example 10d was prepared by acylation of 7-(2,4,6-trimethylphenyl)-2-methyl-4,5,6,7-tetrahydro-2H-pyrazolo[3,4-b]pyridin-3-ylamine (prepared from example 8b using procedures described for examples 8c and 9a; step 1) with methoxyacetyl chloride.

Example 11

2-[2-Methyl-7-(2,4,6-trimethylphenyl)-4,5,6,7-tetrahydro-2H-pyrazolo[3,4-b]pyridin-3-ylmethyl]-1,2,3,4-tetrahydroisoquinoline Dihydrochloride

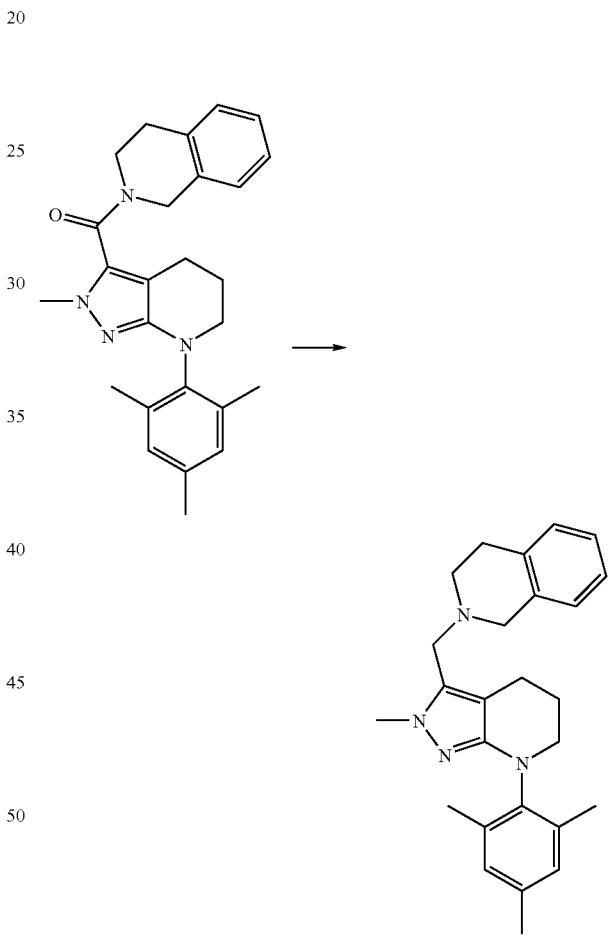

A solution of 140 mg of (3,4-dihydro-1H-isoquinolin-2-yl)[2-methyl-7-(2,4,6-trimethylphenyl)-4,5,6,7-tetrahydro-2H-pyrazolo[3,4-b]pyridin-3-yl]methanone in 6 mL of dry tetrahydrofuran was treated with 4 mL of 1M borane-tetrahydrofuran complex in tetrahydrofuran and stirred under an atmosphere of nitrogen at room temperature for 15 h. The mixture was slowly treated with 5 mL of concentrated HCl and heated at 45° C. for 5 h. The mixture was then cooled to room temperature and made alkaline by the cautious addition of solid sodium bicarbonate. After diluting with water, the mixture was washed twice with 30 mL portions of ethyl acetate. The combined organic extracts were washed with 30 mL of brine, dried over magnesium sulfate, and evaporated to dryness. The residue was purified on a flash silica gel column eluting with 10% acetone/hexane solvent yielding 47 mg of the free base. The dihydrochloride salt was prepared using 1M HCl in ether giving 49 mg of 2-[2-methyl-7-(2,4,6-trimethylphenyl)-4,5,6,7-tetrahydro-2H-pyrazolo[3,4-b]pyridin-3-ylmethyl]-1,2,3,4-tetrahydroisoquinoline dihydrochloride, mp 236.4–241° C.

TABLE 6

Compounds prepared in Examples 10a–10d, and 11.

| Example | Structure | Name | (° C.) | MH+ observed (predicted) |
|---|---|---|---|---|
| 10a | 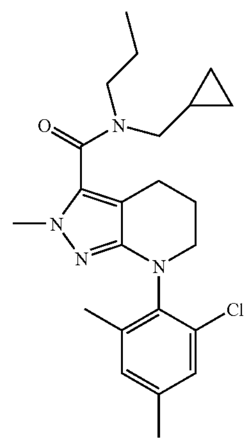 | 7-(2-Chloro-4,6-dimethylphenyl)-2-methyl-4,5,6,7-tetrahydro-2H-pyrazolo[3,4-b]pyridine-3-carboxylic acid cyclopropylmethylpropylamide | 120.6–122.0 | 415 (415) |
| 10b | 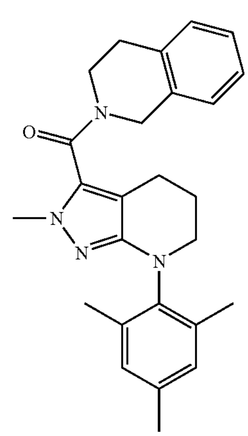 | (3,4-Dihydro-1H-isoquinolin-2-yl)-[2-methyl-7-(2,4,6-trimethylphenyl)-4,5 6,7-tetrahydro-2H-pyrazolo[3,4-b]pyridin-3-yl]-methanone | 80.3–87.7 | 415 (415) |

TABLE 6-continued

Compounds prepared in Examples 10a–10d, and 11.

| Example | Structure | Name | (° C.) | MH+ observed (predicted) |
|---------|-----------|------|--------|--------------------------|
| 10c | 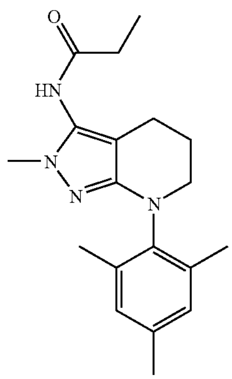 | N-[2-Methyl-7-(2,4,6-trimethylphenyl)-4,5,6,7-tetrahydro-2H-pyrazolo[3,4-b]pyridin-3-yl]propionamide | 226–228 | 327 (327) |
| 10d | 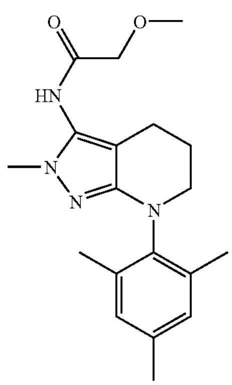 | 2-Methoxy-N-[2-methyl-7-(2,4,6-trimethyl-phenyl)-4,5,6,7-tetrahydro-2H-pyrazolo[3,4-b]pyridin-3-yl]acetamide | 133.8–135.0 | 343 (343) |
| 11 | 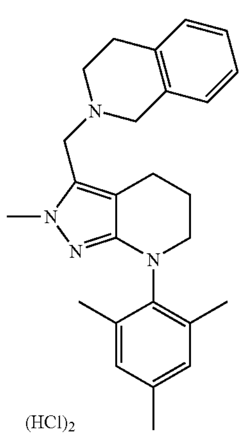 | 2-[2-Methyl-7-(2,4,6-trimethyl-phenyl)-4,5,6,7-tetrahydro-2H-pyrazolo[3,4-b]pyridin-3-ylmethyl]-1,2,3,4-tetrahydroisoquinoline dihydrochloride | 236.4–241.0 | 401 (401) |

Example 12a 7-(2-Chloro-4,6-dimethylphenyl)-2-methyl-3-(1-propylbutoxy)-4,5,6,7-tetrahydro-2H-pyrazolo[3,4-b]pyridine

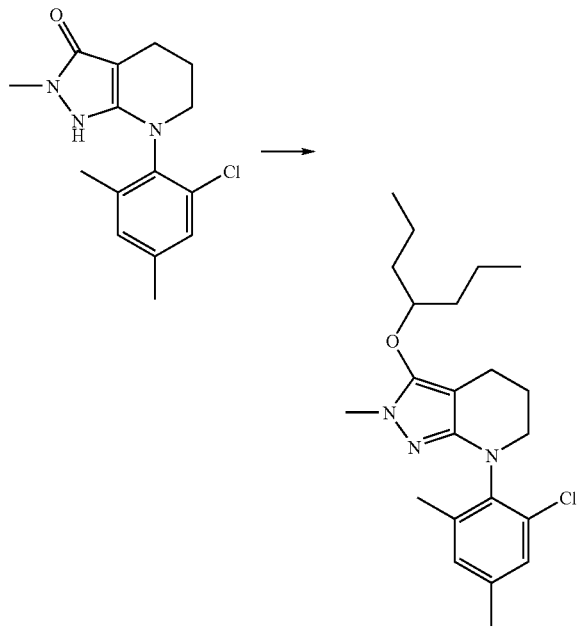

A mixture of 200 mg of 7-(2-chloro-4,6-dimethylphenyl)-2-methyl-1,2,4,5,6,7-hexahydropyrazolo[3,4-b]pyridin-3-one (Example 1, step 5) and 337 mg of triphenylphosphine in 15 mL of dry tetrahydrofuran was treated with 124 mg of 4-heptanol and 224 mg of diethylazodicarboxylate. The mixture was placed under an atmosphere of nitrogen and stirred at room temperature for 16 h. The solvent was evaporated and the residue was purified by flash column chromatography on silica gel using 15% ethyl acetate/hexane as solvent giving 84 mg of 7-(2-chloro-4,6-dimethylphenyl)-2-methyl-3-(1-propylbutoxy)-4,5,6,7-tetrahydro-2H-pyrazolo[3,4-b]pyridine as a colorless oil, ms m/z 390 (MH$^+$).

Example 12b 7-(2,4-Dichlorophenyl)-2-methyl-3-(1-propylbutoxy)-4,5,6,7-tetrahydro-2H-pyrazolo[3,4-b]pyridine Hydrochloride Example 12b was prepared according to the procedure described in Example 12a, except that 7-(2-chloro-4,6-dimethylphenyl)-2-methyl-1,2,4,5,6,7-hexahydropyrazolo[3,4-b]pyridin-3-one was replaced by 7-(2,4-dichlorophenyl)-2-methyl-1,2,4,5,6,7-hexahydropyrazolo[3,4-b]pyridin-3-one.

Example 12c 7-(2-methyl-4-methoxyphenyl)-2-methyl-3-(1-propylbutoxy)-4,5,6,7-tetrahydro-2H-pyrazolo[3,4-b]pyridine Hydrochloride Example 12c was prepared according to the procedure described in Example 12a, except that 7-(2-chloro-4,6-dimethylphenyl)-2-methyl-1,2,4,5,6,7-hexahydropyrazolo[3,4-b]pyridin-3-one was replaced by 7-(4-methoxy-2-methyl-phenyl)-2-methyl-1,2,4,5,6,7-hexahydro-pyrazolo[3,4-b]pyridin-3-one.

Example 12d

Dimethyl-{4-methyl-5-[2-methyl-3-(1-propylbutoxy)-2,4,5,6-tetrahydro-pyrazolo[3,4-b]pyridin-7-yl]-pyridin-2-yl}-amine Example 12c was prepared according to the procedure described in Example 12a, except that 7-(2-chloro-4,6-dimethylphenyl)-2-methyl-1,2,4,5,6,7-hexahydropyrazolo[3,4-b]pyridin-3-one was replaced by 7-(6-dimethylamino-4-methylpyridin-3-yl)-2-methyl-1,2,4,5,6,7-hexahydropyrazolo[3,4-b]pyridin-3-one.

TABLE 7

Compounds prepared in Examples 12a–12d.

| Example | Structure | Name | mp (° C.) | MH+ observed (predicted) |
|---|---|---|---|---|
| 12a | 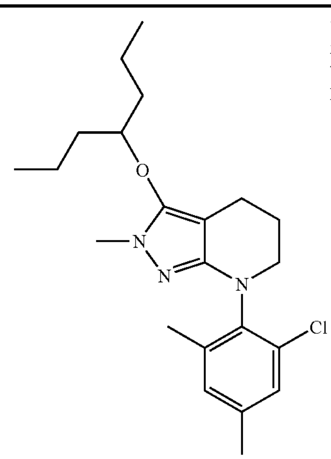 | 7-(2-Chloro-4,6-dimethylphenyl)-2-methyl-3-(1-propylbutoxy)-4,5,6,7-tetrahydro-2H-pyrazolo[3,4-b]pyridine | oil | 390 (390) |

TABLE 7-continued

Compounds prepared in Examples 12a–12d.

| Example | Structure | Name | mp (° C.) | MH+ observed (predicted) |
|---|---|---|---|---|
| 12b | 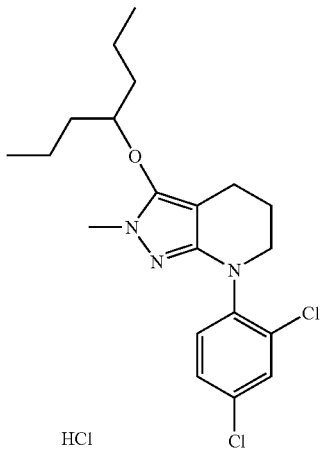 | 7-(2,4-Dichlorophenyl)-2-methyl-3-(1-propylbutoxy)-4,5,6,7-tetrahydro-2H-pyrazolo[3,4-b]pyridine hydrochloride | oil | 396 (396) |
| 12c | 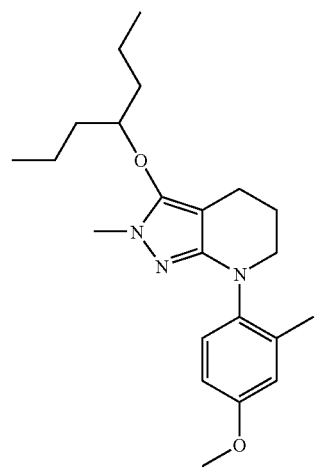 | 7-(4-Methoxy-2-methylphenyl)-2-methyl-3-(1-propylbutoxy)-4,5,6,7-tetrahydro-2H-pyrazolo[3,4-b]pyridine | oil | 372 (372) |
| 12d | 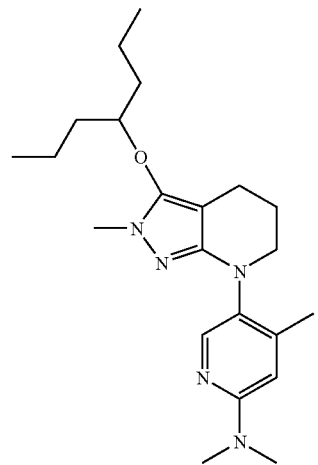 | Dimethyl-{4-methyl-5-[2-methyl-3-(1-propylbutoxy)-2,4,5,6-tetrahydro-pyrazolo[3,4-b]pyridin-7-yl]-pyridin-2-yl}-amine | oil | 386 (386) |

Example 13a

2-Methyl-3-(2-trifluoromethylphenyl)-7-(2,4,6-trimethylphenyl)-4,5,6,7-tetrahydro-2H-pyrazolo[3,4-b]pyridine

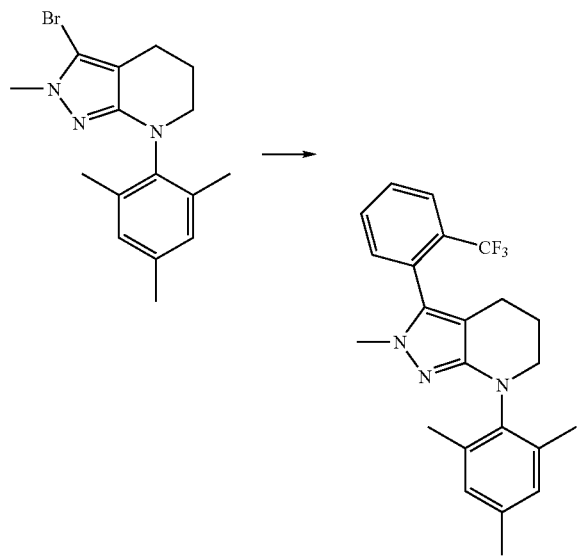

A mixture of 200 mg of 3-bromo-2-methyl-7-(2,4,6-trimethylphenyl)-4,5,6,7-tetrahydro-2H-pyrazolo[3,4-b]pyridine, 124 mg of 2-trifluoromethylphenylboronic acid, and 14 mg of tetrakistriphenylphosphine palladium (0) in 2 mL of dioxane was treated with a solution of 210 mg of sodium carbonate in 2 mL of water. The mixture was placed under an atmosphere of argon and heated to 100° C. for 20 h. The mixture was cooled to room temperature, diluted with 20 mL of ethyl acetate, washed with 20 mL of 1 M HCl and 20mL of brine, dried over magnesium sulfate, and evaporated to dryness. The residue was purified by flash silica gel column chromatography using 7% acetone/hexane as solvent yielding 87 mg of 2-methyl-3-(2-trifluoromethylphenyl)-7-(2,4,6-trimethylphenyl)-4,5,6,7-tetrahydro-2H-pyrazolo[3,4-b]pyridine, mp 59–63° C.

Example 13b 3-(2,6-Dimethoxyphenyl)-2-methyl-7-(2,4,6-trimethylphenyl)-4,5,6,7-tetrahydro-2H-pyrazolo[3,4-b]pyridine Example 13b was prepared according to the procedure described in Example 13a, except that 2-trifluoromethylphenylboronic acid was replaced by 2,6-bismethoxyphenylboronic acid.

TABLE 8

Compounds prepared in Examples 13a–13b.

| Example | Structure | Name | mp (° C.) | MH+ observed (predicted) |
|---|---|---|---|---|
| 13a | 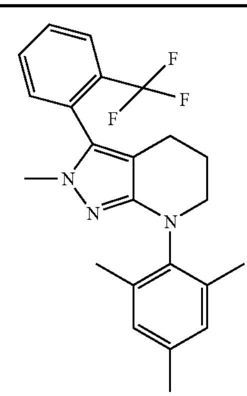 | 2-Methyl-3-(2-trifluoromethylphenyl)-7-(2,4,6-trimethylphenyl)-4,5,6,7-tetrahydro-2H-pyrazolo[3,4-b]pyridine | 59–63 | 400 (400) |
| 13b | 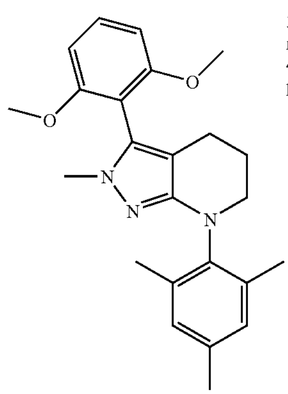 | 3-(2,6-Dimethoxyphenyl)-2-methyl-7-(2,4,6-trimethylphenyl)-4,5,6,7-tetrahydro-2H-pyrazolo[3,4-b]pyridine | 169.9–172.8 | 392 (392) |

Example 14

Contemplated Compounds

In addition to the compounds exemplified herein, the compounds shown in Table 9 are contemplated to fall within the scope of the invention. In addition, the compounds shown in Table 9 illustrate certain species of compounds that are generically described herein.

TABLE 9

| Contemplated compounds |
| --- |

TABLE 9-continued

| Contemplated compounds |
| --- |

TABLE 9-continued
Contemplated compounds
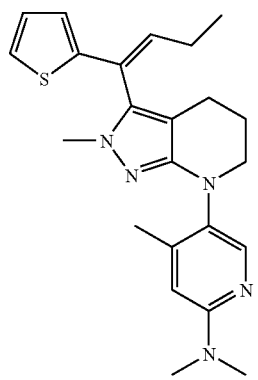
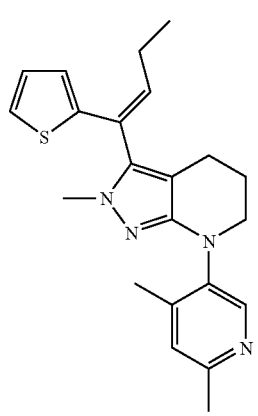
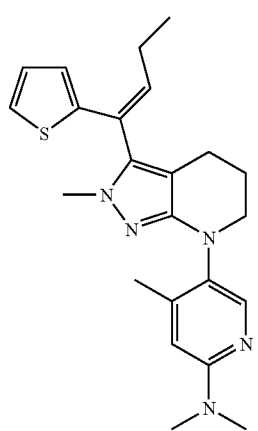
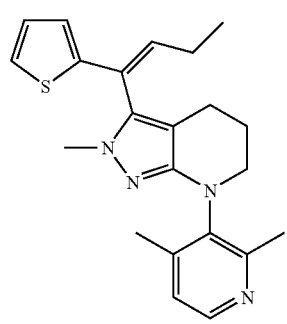
TABLE 9-continued
Contemplated compounds
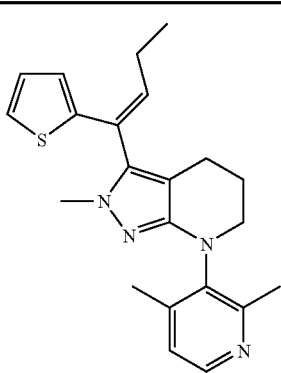
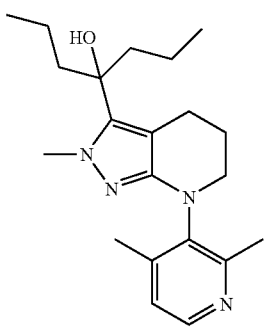
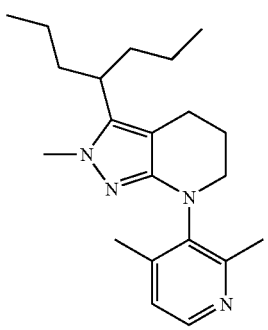
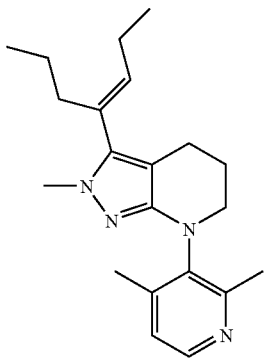

TABLE 9-continued
Contemplated compounds
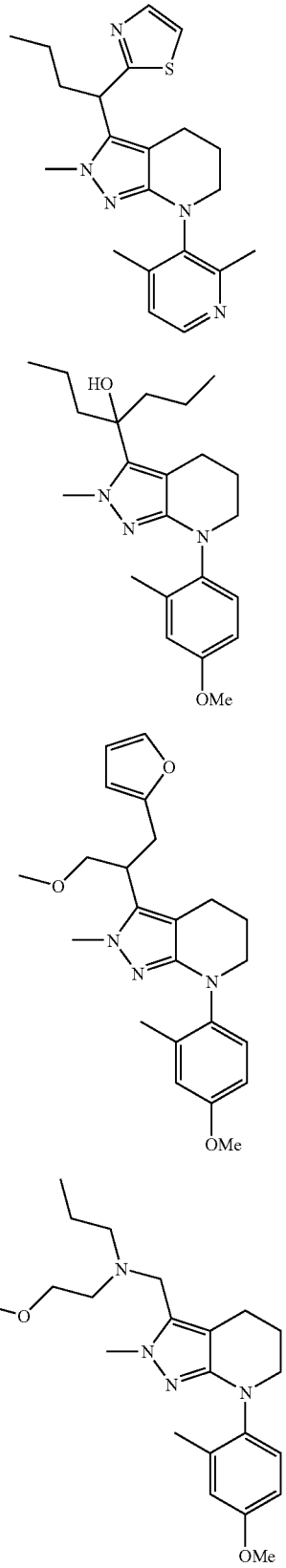
TABLE 9-continued
Contemplated compounds
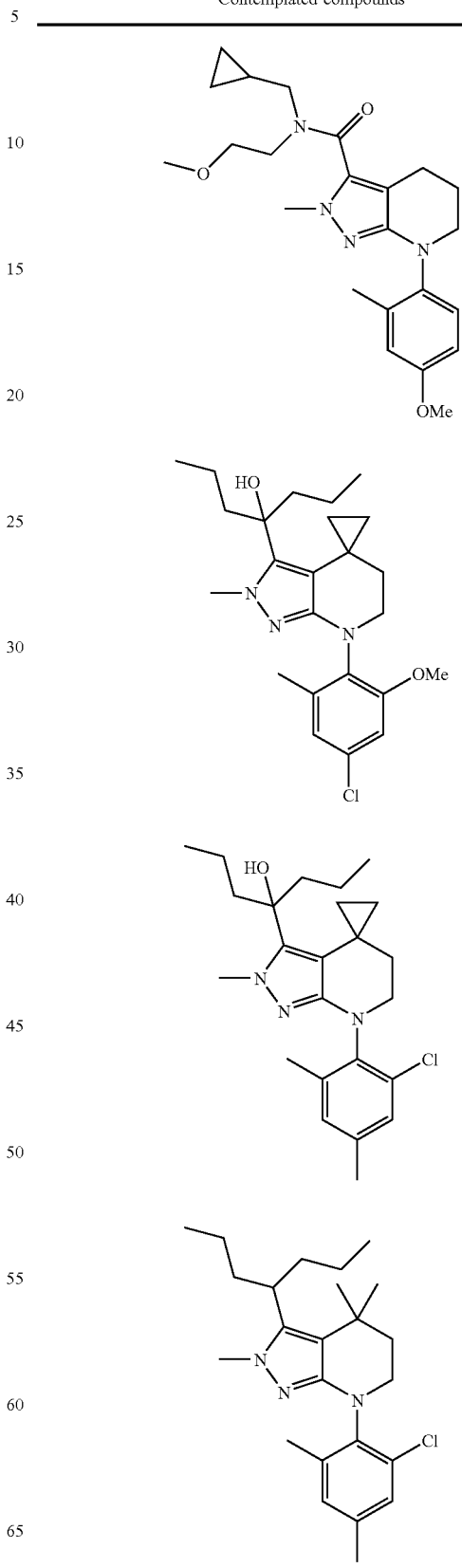

TABLE 9-continued
Contemplated compounds
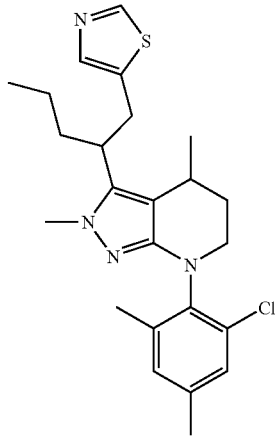
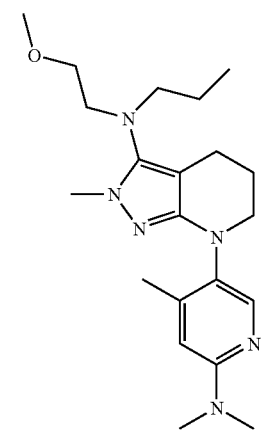
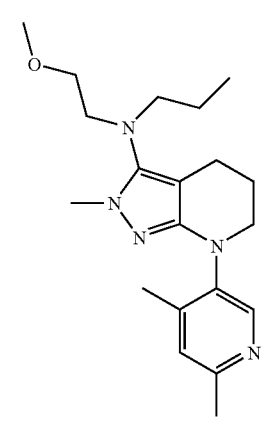
TABLE 9-continued
Contemplated compounds
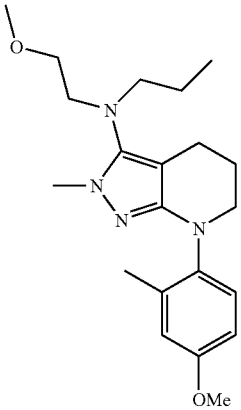
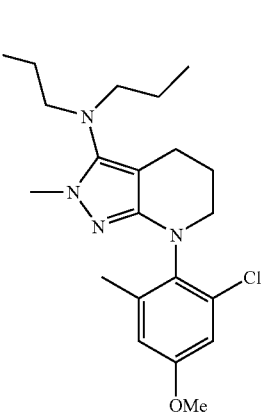
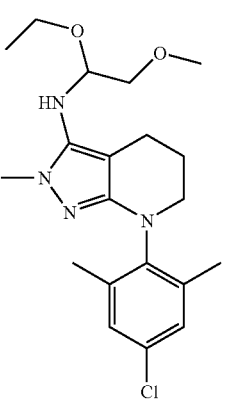
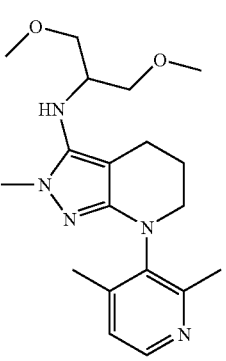

TABLE 9-continued
Contemplated compounds
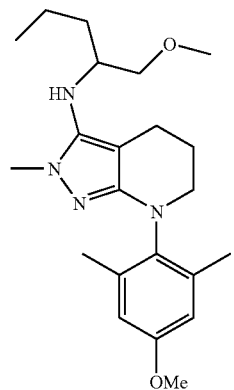
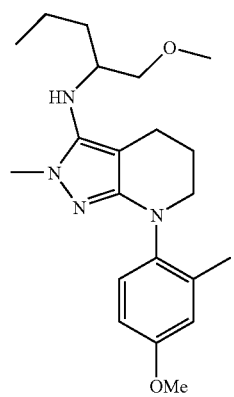
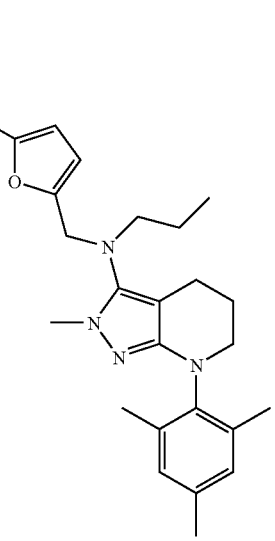
TABLE 9-continued
Contemplated compounds
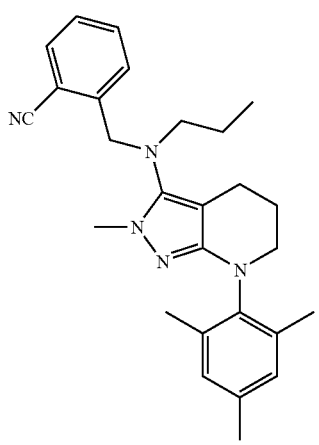
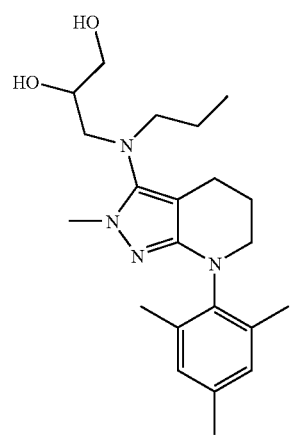
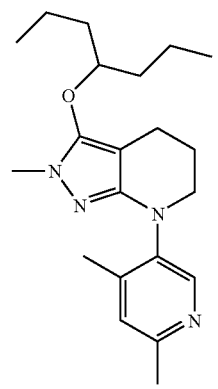

TABLE 9-continued
Contemplated compounds
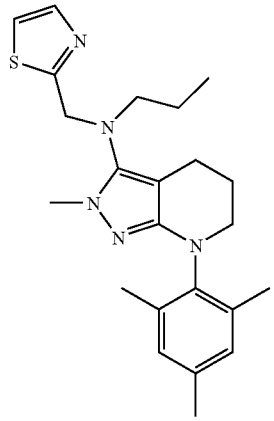
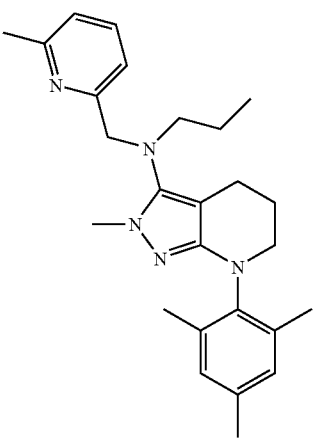
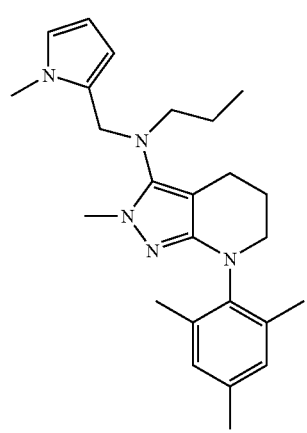
TABLE 9-continued
Contemplated compounds
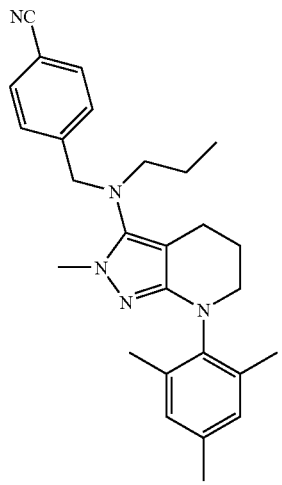
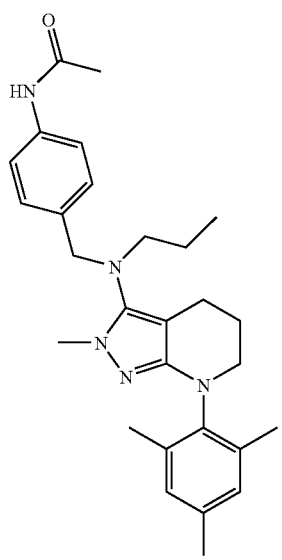
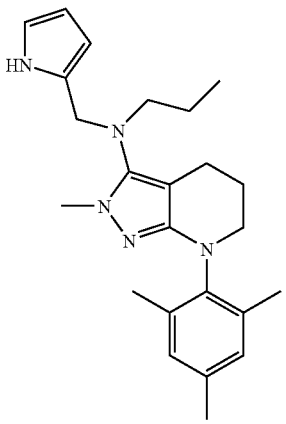

TABLE 9-continued
Contemplated compounds
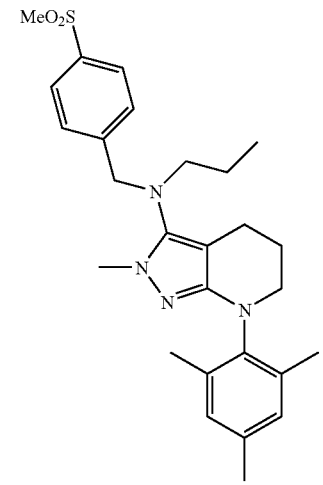
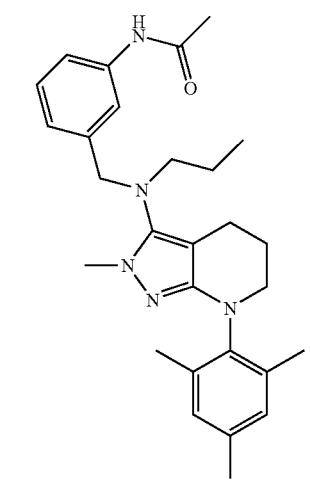
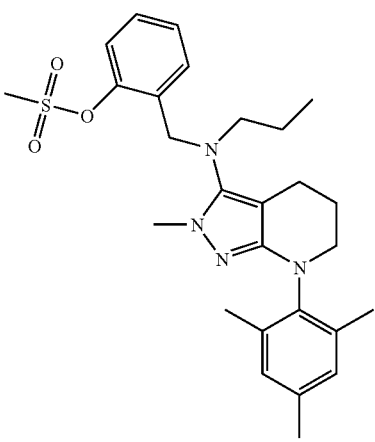
TABLE 9-continued
Contemplated compounds
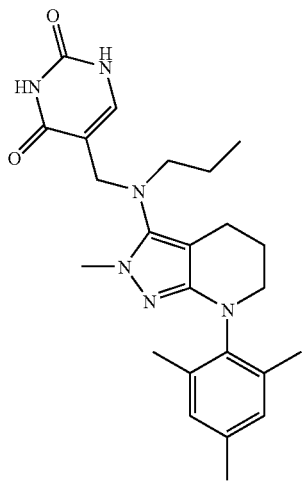
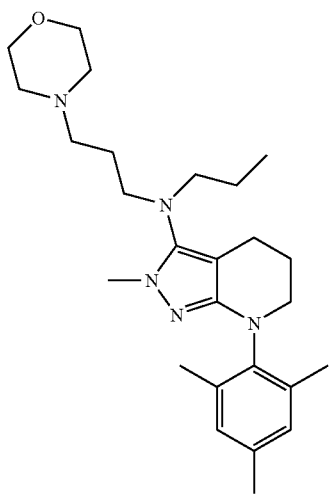
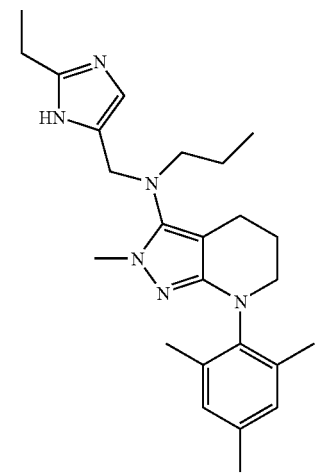

Example 15

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and, granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (IV)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 16

Intracellular cAMP Stimulation Assay

Human Y-79 retinoblastoma cells are grown in RPMI 1640 medium with 15% FBS. Measures of cAMP accumulation are performed by using NEN Adenylyl Cyclase Flash-Plate kit (SMP004). The cells are separated from culture medium, washed twice with PBS (150×g, 8 min), resuspended (2E+6 cells/ml) in Stimulation Buffer (provided in the kit), and then added to 96-well FlashPlates, (50,000 cells per well). Various concentrations of test compounds are incubated with the cells for 20 min prior to the addition of hCRF (30 nM). The total assay volume is 100 µl. The assay is terminated after 20 min after addition of the hCRF by addition of Detection Buffer and [$^{125}$I]cAMP. After 2 hr at room temperature the mixtures are aspirated and the bound radioactivity is measured with a Packard TopCount. The potency (IC$_{50}$ values) of test compounds in inhibiting the hCRF-stimulated accumulation of cAMP is determined by nonlinear regression analyses with interactive curve-fitting procedures.

Example 17

CRF Receptor Binding Assay

Human IMR-32 neuroblastoma cells are grown to 80% confluence in MEM medium containing 10% heat-inactivated FBS, 1 mM Sodium Pyruvate, and 0.1 mM nonessential amino acids. Celll membranes are prepared according the method of Dieterich and DeSouza (1996). The cells (~5E+9) are resuspended in 10 volumes of wash buffer (5 mM Tris HCl, 10 mM MgCl$_2$, 2 mM EGTA, pH 7.4 at RT), homogenized with a Polytron, and then centrifuged at 45,000 G for 20 min at 4° C. The membrane pellets are washed twice with wash buffer (45,000 G for 20 min at 4° C.) and then resuspended (50 mM Tris HCl, 10 mM MgCl$_2$, 2 mM EGTA, pH 7.4 at RT). Protein concentration is determined using Pierce reagents and BSA as standard. Aliquots of 1–1.5 ml are stored at −80° C. until binding assay.

The competition binding assay is performed in a final volume of 250 μl, which contains assay buffer (50 mM Tris-HCl, 10 mM MgCl$_2$, 2 mM EGTA, 0.2% BSA, 0.1 mM bacitracin and 100 kIU/ml aprotinin pH 7.2 at R.T.), 0.05 nM [$^{125}$I]Tyr$^0$-ovine CRF (Du Pont New England Nuclear), 50 μg of membrane protein, and test compound at various concentrations. Non-specific binding is determined with 1 μM hCRF. Binding reactions are terminated after 2 hr incubation at 25° C. by filtering through 96-w GF/C filter plate using a Packard Harvester (Filtermate 196). The 96-w filter plate is pre-treated with 0.3% polyethyleneimine and pre-washed with washing buffer (50 mM Tris-HCl, 10 mM MgCl$_2$, 2 mM EGTA, 0.2% BSA, pH 7.2 at 4° C.). Unbound radioactivity is removed by four rapid washes (0.8 ml/well) with wash buffer. The radioactivity is quantified using a Packard TopCount. Data are analyzed using non-linear iterative curve fitting to obtain IC$_{50}$ and Hill slope values. PKi values are derived from pIC$_{50}$ values (−log of IC$_{50}$).

The compounds of the present invention were active in the receptor binding and functional assay. The IC$_{50}$ of of representative examples in the CRF functional assay are shown in Table 10.

TABLE 10

CRF1 receptor binding affinity of compounds of Formula I.

| Example | hCRF1 (pIC$_{50}$) |
|---|---|
| 1 | 5.97 |
| 5c | 4.95 |
| 6e | 6.63 |
| 7b | 7.06 |
| 9c | 6.08 |
| 11 | 4.92 |
| 12b | 7.56 |
| 13a | 6.11 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, or process step or steps, to the objective spirit and scope of the present invention. All such modifications are intended to be within the scope of the claims appended hereto.

What is claimed is:

1. A compound of Formula I or Formula II:

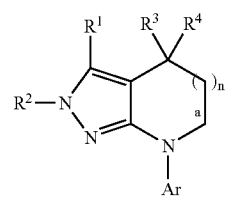

Formula I or

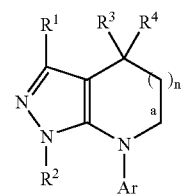

Formula II wherein:

R$^1$ is —NR$^a$R$^b$;

R$^2$ is hydrogen, C$_{1-6}$alkyl, C$_{3-6}$cycloalkyl, C$_{3-6}$cycloalkylalkyl, C$_{1-6}$alkylcarbonyl, C$_{1-6}$alkylsulfonyl, aryl, or arylalkyl, wherein said aryl or arylalkyl is optionally substituted with one or more substituents independently selected from C$_{1-6}$alkyl, haloalkyl, C$_{1-6}$alkoxy, and halogen;

R$^3$ and R$^4$ are each independently selected from hydrogen and C$_{1-6}$alkyl, or R$^3$ and R$^4$ are taken together with the carbon to which they are attached to form a C$_{3-6}$cycloalkyl ring;

Ar is aryl optionally substituted with one or more substituents independently selected from the group consisting of C$_{1-6}$alkyl, C$_{1-6}$alkoxy, C$_{1-6}$alkylthio, C$_{1-6}$alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, C$_{1-6}$alkyl, and C$_{1-6}$alkylcarbonyl;

R$^a$ is C$_{1-6}$alkyl, C$_{1-6}$alkoxyalkyl, C$_{1-6}$alkylthioalkyl; and R$^b$ is heteroarylalkyl;

n is 1;

a is a single bond;

or individual isomers, racemic or non-racemic mixtures of isomers, or pharmaceutically acceptable salts thereof.

2. The compound of claim 1, wherein the compound is of Formula I:

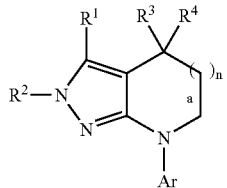

Formula I and $R^1$ is —$NR^aR^b$.

3. The compound of claim 2, wherein Ar is a di- or tri-substituted phenyl, and the substituents are each independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-6}$alkyl, and $C_{1-6}$alkylcarbonyl.

4. The compound of claim 3, wherein $R^3$ and $R^4$ are each independently selected from hydrogen and methyl.

5. The compound of claim 4, wherein Ar is a 2,4-disubstituted or 2,4,6-trisubstituted phenyl.

6. The compound of claim 5, wherein Ar is a 2,4-disubstituted or 2,4,6-trisubstituted phenyl, and the substituents are each independently selected from the group consisting of $C_{1-6}$alkyl, $C_{1-6}$alkoxy, $C_{1-6}$alkylthio, halogen, haloalkyl, cyano, alkylamino, dialkylamino, and nitro.

7. The compound of claim 6, wherein $R^2$ is hydrogen, $C_{1-6}$alkyl, or $C_{1-6}$alkylcarbonyl.

8. The compound of claim 7, wherein $R^3$ and $R^4$ are each independently selected from hydrogen and methyl.

9. The compound of claim 8, wherein $R^2$ is $C_{1-6}$alkyl; $R^3$ and $R^4$ are hydrogen; and Ar is a 2,4-disubstituted or 2,4,6-trisubstituted phenyl, and the substituents are independently selected from the group consisting of $C_{1-6}$alkyl, $C_{1-6}$alkoxy, halogen, haloalkyl, cyano, and —$NR^{a''}R^{b''}$, where $R^{a''}$ and $R^{b''}$ are each independently selected from the group consisting of hydrogen and $C_{1-6}$alkyl.

10. A pharmaceutical composition comprising a therapeutically effective amount of at least one compound of claim 1 in admixture with at least one pharmaceutically acceptable carrier.

11. The method of treating a disease state selected from the group consisting of phobias, stress-related illnesses, mood disorders, eating disorders, generalized anxiety disorders, stress-induced gastrointestinal dysfunctions, neurodegenerative diseases, and neuropsychiatric disorders comprising administering to a mammal in need thereof a therapeutically effective amount of a compound of claim 1.

* * * * *